US012774490B2

(12) United States Patent
Blainey et al.

(10) Patent No.: US 12,774,490 B2
(45) Date of Patent: Oct. 27, 2026

(54) CONSTRUCT FOR CONTINUOUS MONITORING OF LIVE CELLS

(71) Applicants: THE BROAD INSTITUTE, INC., Cambridge, MA (US); MASSACHUSETTS INSTITUTE OF TECHNOLOGY, Cambridge, MA (US)

(72) Inventors: Paul Blainey, Cambridge, MA (US); Jacob Borrajo, Cambridge, MA (US); Mohamad Najia, Cambridge, MA (US); Hong Anh Anna Le, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 1338 days.

(21) Appl. No.: 17/599,722

(22) PCT Filed: Mar. 29, 2020

(86) PCT No.: PCT/US2020/025603
§ 371 (c)(1),
(2) Date: Sep. 29, 2021

(87) PCT Pub. No.: WO2020/205681
PCT Pub. Date: Oct. 8, 2020

(65) Prior Publication Data

US 2022/0195514 A1 Jun. 23, 2022

Related U.S. Application Data

(60) Provisional application No. 62/826,763, filed on Mar. 29, 2019.

(51) Int. Cl.
*C12Q 1/6869* (2018.01)
*C07K 14/005* (2006.01)
(Continued)

(52) U.S. Cl.
CPC .......... *C12Q 1/6869* (2013.01); *C07K 14/005* (2013.01); *C07K 14/395* (2013.01);
(Continued)

(58) Field of Classification Search
None
See application file for complete search history.

(56) References Cited

U.S. PATENT DOCUMENTS 5,869,326 A 2/1999 Hofmann
2005/0119171 A1* 6/2005 Bejanin .................. C07K 14/47 514/1.9

(Continued)

FOREIGN PATENT DOCUMENTS

WO 97/49450 A1 12/1997
WO 98/52609 A1 11/1998
(Continued)

OTHER PUBLICATIONS

Luo et al. (Hypoxia preconditioning promotes bone marrow mesenchymal stem cells survival by inducing HIF-1Î± in injured neuronal cells derived exosomes culture system, Cell Disease and Death, published Jan. 2019) (Year: 2019).*
(Continued)

*Primary Examiner* — Heather Calamita
*Assistant Examiner* — Elizabeth Rose Lafave
(74) *Attorney, Agent, or Firm* — GTC Law Group PC & Affiliates

(57) ABSTRACT

The present invention provides for methods to obtain transcriptome-wide multiple information-rich samples from living cells while minimally disrupting the cell. The subject matter disclosed herein is generally related to nucleic acid constructs for continuous monitoring of live cells. Specifically, the subject matter disclosed herein is directed to nucleic acid constructs that encode a fusion protein and a
(Continued)

construct RNA sequence that induce live cells to self-report cellular contents while maintaining cell viability. The present invention may be used to monitor gene expression in single cells while maintaining cell viability.

19 Claims, 42 Drawing Sheets

Specification includes a Sequence Listing.

(51) Int. Cl.

| | |
|---|---|
| ***C07K 14/395*** | (2006.01) |
| ***C12N 7/00*** | (2006.01) |
| ***C12N 15/62*** | (2006.01) |
| ***C12N 15/86*** | (2006.01) |
| ***C12Q 1/6806*** | (2018.01) |
| ***C12Q 1/6876*** | (2018.01) |
| ***C12Q 1/6897*** | (2018.01) |
| ***G01N 33/50*** | (2006.01) |

(52) U.S. Cl.

CPC ............... *C12N 7/00* (2013.01); *C12N 15/62* (2013.01); *C12N 15/86* (2013.01); *C12Q 1/6806* (2013.01); *C12Q 1/6876* (2013.01); *G01N 33/5023* (2013.01); *C12N 2740/15022* (2013.01); *C12N 2740/15043* (2013.01); *C12N 2740/16022* (2013.01); *C12N 2740/16023* (2013.01); *C12N 2740/16042* (2013.01); *C12N 2740/16043* (2013.01); *C12N 2830/002* (2013.01); *C12Q 1/6897* (2013.01); *C12Q 2535/122* (2013.01); *C12Q 2563/179* (2013.01); *C12Q 2600/158* (2013.01)

(56) References Cited

U.S. PATENT DOCUMENTS

| | | | |
|---|---|---|---|
| 2014/0004146 | A1 | 1/2014 | Zhou |
| 2016/0194625 | A1 | 7/2016 | Hoge |
| 2016/0253584 | A1 | 9/2016 | Fodor et al. |
| 2018/0079786 | A1 | 3/2018 | Blainey |

FOREIGN PATENT DOCUMENTS

| | | | |
|---|---|---|---|
| WO | 2004/015075 | A2 | 2/2004 |
| WO | 2011/008730 | A2 | 1/2011 |
| WO | 2013174999 | A1 | 11/2013 |
| WO | 2014/047556 | A1 | 3/2014 |
| WO | 2014/047561 | A1 | 3/2014 |
| WO | 2014/093622 | A2 | 6/2014 |
| WO | 2014/110509 | A1 | 7/2014 |
| WO | 2014/143158 | A1 | 9/2014 |
| WO | 2014/204725 | A1 | 12/2014 |
| WO | 2018057812 | A2 | 3/2018 |
| WO | 2019/005884 | A1 | 1/2019 |
| WO | 2019/060746 | A1 | 3/2019 |
| WO | 2020205681 | A1 | 10/2020 |

OTHER PUBLICATIONS

Rulli et al. Selective and Nonselective Packaging of Cellular RNAs in Retrovirus Particles. Journal of Virology, The American Society of Microbiology. Jun. 1, 2007.

Sun et al. A New RNA Vaccine Platform Based on MS2 Virus-Like Particles Produced in. Biochemical and Biophysical Research Communications. Mar. 21, 2011.

Partial Supplementary European Search Report in corresponding EP application No. 17853940.9 dated Jun. 2, 2020.

Kiyama et al. In Vitro Transcription of a Poly(dA) {middledot}Poly(dT)-Containing Sequence is Inhibited by Interaction between the Template and Its Transcripts, Nucleic Acids Research. Nov. 1, 1996.

Extended European Search Report in corresponding EP application No. 17853940.9 dated Sep. 30, 2020.

Examination Report in corresponding EP application No. 17853940.9 dated May 24, 2024.

Jouvenet et al. Imaging of the Interaction of HIV-1 Genomes and Gag During Assembly of Individual Viral Particles PNAS, 2009.

Zhang et al. Analysis of the Assembly Function of the Human Immunodeficiency Virus Type 1 Gag Protein Nucleocapsid Domain. Journal of Virology. 1998.

Massachusetts Institute of Technology, "International Preliminary Report on Patentability issued in International Patent Application No. PCT/US2020/025603 filed Mar. 29, 2020", mailed Oct. 14, 2021, 7 pages.

Brockmann, et al., "Structural Basis for Polyadenosine-RNA Binding by Nab2 Zn Fingers and Its Function in mRNA Nuclear Export", Structure, vol. 20, No. 6, May 2012, 1007-1018.

Deshpande, et al., "Current Trends in the Use of Liposomes for Tumor Targeting", Nanomedicine (Lond), vol. 8, No. 9, Sep. 2013, 32 pages.

Kuhlmann, et al., "Structural Basis for the Molecular Recognition of Polyadenosine RNA by Nab2 Zn Fingers", Nucleic Acids Research, vol. 42, No. 1, 2014, 672-680.

Liu, et al., "Engineering Cell Signaling Using Tunable CRISPR-Cpf1-based Transcription Factors", Nature Communications, vol. 8, No. 2095, Dec. 13, 2017, 8 pages.

Lorenzer, et al., "Going Beyond the Liver: Progress and Challenges of Targeted Delivery of siRNA Therapeutics", Journal of Controlled Release, vol. 203, Apr. 2015, 1-15.

Ran, et al., "Double Nicking by RNA-Guided CRISPR Cas9 for Enhanced Genome Editing Specificity", Cell, vol. 154, No. 6, Sep. 12, 2013, 1380-1389.

Safaee, et al., "Interdomain Allostery Promotes Assembly of the Poly(A) mRNA Complex with PABP and eIF4G", Molecular Cell, vol. 48, Issue 3, Nov. 9, 2012, p. 375-386.

"International Search Report and Written Opinion issued in International Patent Application No. PCT/US2020/025603 filed Mar. 29, 2020", mailed Jul. 13, 2020, 14 pages.

Office Action in correspondence EP application No. 20720883.6 dated Feb. 2, 2024.

* cited by examiner

| reporting unit scale | typical number of cells in reporting unit | sample collection time to accumulate 10 detected counts of a given mRNA, protein, or lipid species* | | |
|---|---|---|---|---|
| | | example RNA species present at 1000 copies per cell (assume total of 200,000 mRNA/cell) | example protein species present at 0.05% in VLP sample | example lipid species present at 0.05% in VLP sample |
| Single Cell | 1 | hours | ~ | ~ |
| Tissue | 50,000 | seconds | seconds | seconds |
| Organ | 10,000,000 | very short | very short | very short |
| Organism | 1 x $10^{13}$ | very short | very short | very short |
| Total molecules sampled per cell per hour | | 3,000 | 100,000 | 1,000,000 |
| estimated % of cell's production | | 10% | <1% | <5% |
| estimated analytical detection efficiency | | 10% | 0.1% | 0.1% |

* equivelant to assay time resolution for quantification with coefficient of variation ~30%

FIG. 10

SEQUENCE LISTING

<160> NUMBER OF SEQ ID NOS: 16

<210> SEQ ID NO 1
<211> LENGTH: 1590
<212> TYPE: DNA
<213> ORGANISM: Artificial Sequence
<220> FEATURE:
<223> OTHER INFORMATION: Synthetic

<400> SEQUENCE: 1

```
atgggccaga ctgttaccac tcccttaagt ttgaccttag gtcactggaa agatgtcgag      60
cggatcgctc acaaccagtc ggtagatgtc aagaagagac gttgggttac cttctgctct     120
gcagaatggc caacctttaa cgtcggatgg ccgcgagacg gcacctttaa ccgagacctc     180
atcacccagg ttaagatcaa ggtcttttca cctggcccgc atggacaccc agaccaggtc     240
ccctacatcg tgacctggga agccttggct tttgaccccc ctccctgggt caagcccttt     300
gtacacccta agcctccgcc tcctcttcct ccatccgccc cgtctctccc ccttgaacct     360
cctcgttcga ccccgcctcg atcctccctt tatccagccc tcactccttc tctaggcgcc     420
aaacctaaac ctcaagttct ttctgacagt ggggggccgc tcatcgacct acttacagaa     480
gaccccccgc cttataggga cccaagacca ccccccttccg acagggacgg aaatggtgga    540
gaagcgaccc ctgcgggaga ggcaccggac ccctccccaa tggcatctcg cctacgtggg     600
agacgggagc cccctgtggc cgactccact acctcgcagg cattcccccct ccgcgcagga    660
ggaaacggac agcttcaata ctggccgttc tcctcttctg acctttacaa ctggaaaaat     720
aataaccctt ctttttctga agatccaggt aaactgacag ctctgatcga gtctgttctc     780
atcacccatc agcccacctg ggacgactgt cagcagctgt tggggactct gctgaccgga     840
gaagaaaaac aacgggtgct cttagaggct agaaaggcgg tgcggggcga tgatgggcgc     900
cccactcaac tgcccaatga agtcgatgcc gcttttcccc tcgagcgccc agactgggat     960
tacaccaccc aggcaggtag gaaccaccta gtccactatc gccagttgct cctagcgggt    1020
ctccaaaacg cgggcagaag ccccaccaat ttggccaagg taaaaggaat aacacaaggg    1080
cccaatgagt ctccctcggc cttcctagag agacttaagg aagcctatcg caggtacact    1140
ccttatgacc ctgaggaccc agggcaagaa actaatgtgt ctatgtcttt catttggcag    1200
tctgccccag acattgggag aaagttagag aggttagaag atttaaaaaa caagacgctt    1260
ggagatttgg ttagagaggc agaaaagatc tttaataaac gagaaacccc ggaagaaaga    1320
gaggaacgta tcaggagaga aacagaggaa aaagaagaac gccgtaggac agaggatgag    1380
cagaaagaga aagaaagaga tcgtaggaga catagagaga tgagcaagct attggccact    1440
gtcgttagtg gacagaaaca ggatagacag ggaggagaac gaaggaggtc ccaactcgat    1500
cgcgaccagt gtgcctactg caaagaaaag gggcactggg ctaaagattg tcccaagaaa    1560
ccacgaggac ctcggggacc aagaccgcag                                     1590
```

<210> SEQ ID NO 2
<211> LENGTH: 1935
<212> TYPE: DNA
<213> ORGANISM: Artificial Sequence
<220> FEATURE:
<223> OTHER INFORMATION: Synthetic

<400> SEQUENCE: 2

```
atgaacgctg cggccagcag ctaccccatg gcctccctgt acgtgggcga cctgcattcg      60
gacgtcaccg aggccatgct gtacgaaaag ttcagccccg cggggcctgt gctgtccatc     120
```

cgggtctgcc gcgatatgat cacccgccgc tccctgggct atgcctacgt caacttccag 180
cagccggccg acgctgagcg ggctttggac accatgaact ttgatgtgat taagggaaag 240
ccaatccgca tcatgtggtc tcagagggat ccctctttga gaaaatctgg tgtgggaaac 300
gtcttcatca agaacctgga caaatctata gataacaagg cactttatga tacttttct 360 gcttttggaa acatactgtc ctgcaaggtg gtgtgtgatg agaacggctc taagggttat 420
gcctttgtcc acttcgagac ccaagaggct gccgacaagg ccatcgagaa gatgaatggc 480
atgctcctca atgaccgcaa agtatttgtg ggcagattca agtctcgcaa agagcgggaa 540
gctgagcttg gagccaaagc caaggaattc accaatgttt atatcaaaaa ctttggggaa 600
gaggtggatg atgagagtct gaaagagcta ttcagtcagt ttggtaagac cctaagtgtc 660
aaggtgatga gagatcccaa tgggaaatcc aaaggctttg gctttgtgag ttacgaaaaa 720
cacgaggatg ccaataaggc tgtggaagag atgaatggaa aagaaataag tggtaaaatc 780
atatttgtag gccgtgcaca aaagaaagta gaacggcagg cagagttaaa acggaaattt 840
gaacagttga aacaggagag aattagtcga tatcaggggg tgaatctcta cattaagaac 900
ttggatgaca ctattgatga tgagaaatta aggaaagaat tttctccttt tggatcaatt 960
accagtgcta aggtaatgct ggaggatgga agaagcaaag ggtttggctt cgtctgcttc 1020
tcatctcctg aagaagcaac caaagcagtc actgagatga atggacgcat tgtgggctcc 1080
aagccactat atgttgccct ggcccagagg aaggaagaga gaaaggctca cctgaccaac 1140
cagtatatgc aacgagtggc tggaatgaga gcacttcctg ccaatgccat cttaaatcag 1200
ttccagcctg cagcgggtgg ctactttgtg ccagcagtcc cacaggctca gggaaggcct 1260
ccatattata cacctaacca gttagcacag atgaggccta atccacgctg gcagcaaggt 1320
gggagacctc aaggcttcca aggaatgcca agtgctatac gccagtctgg gcctcgtcca 1380
actcttcgcc atctggctcc aactgggtct gagtgcccgg accgcttggc tatggacttt 1440
ggtggggctg gtgccgccca gcaagggctg actgacagct gccagtctgg aggcgttccc 1500
acagctgtgc agaacttagc gccacgcgct gctgttgctg ctgctgctcc ccgggctgtt 1560 gcccccctaca aatacgcctc cagtgtccgc agccctcatc ctgccataca gcctctgcag 1620
gcaccccagc ctgcggtcca tgtgcagggg caggagccac tgactgcctc catgctggct 1680
gcagcacccc cccaggaaca gaagcagatg ctgggagaac gcttgttccc actcatccaa 1740
acaatgcatt caaatctggc tgggaagatc acgggaatgc tgctggagat agacaactct 1800
gagctgctgc acatgttaga gtcccccgag tctctccgct ccaaggtgga tgaagctgta 1860
gcagttctac aggctcatca tgccaagaaa gaagctgccc agaaggtggg cgctgttgct 1920
gctgctacct cttag 1935

<210> SEQ ID NO 3
<211> LENGTH: 387
<212> TYPE: DNA
<213> ORGANISM: Artificial Sequence
<220> FEATURE:
<223> OTHER INFORMATION: Synthetic

<400> SEQUENCE: 3
gcttcaaact ttactcagtt cgtgctcgtg gacaatggtg ggacagggga tgtgacagtg 60
gctccttcta atttcgctaa tggggtggca gagtggatca gctccaactc acggagccag 120
gcctacaagg tgacatgcag cgtcaggcag tctagtgccc agaagagaaa gtataccatc 180 aggtggagg tccccaaagt ggctacccag acagtgggcg gagtcgaact gcctgtcgcc 240
gcttggaggt cctacctgaa catggagctc actatcccaa ttttcgctac caattctgac 300
tgtgaactca tcgtgaaggc aatgcagggg ctcctcaaag acggtaatcc tatcccttcc 360
gccatcgccg ctaactcagg tatctac 387

<210> SEQ ID NO 4
<211> LENGTH: 4137
<212> TYPE: DNA
<213> ORGANISM: Artificial Sequence
<220> FEATURE:
<223> OTHER INFORMATION: Synthetic

<400> SEQUENCE: 4
atgagcccca agaagaagag aaaggtggag gccagcgaca agaagtacag catcggcctg 60
gccatcggca ccaactctgt gggctgggcc gtgatcaccg acgagtacaa ggtgcccagc 120
aagaaattca aggtgctggg caacaccgac cggcacagca tcaagaagaa cctgatcgga 180
gccctgctgt tcgacagcgg cgaaacagcc gaggccaccc ggctgaagag aaccgccaga 240
agaagataca ccagacggaa gaaccggatc tgctatctgc aagagatctt cagcaacgag 300
atggccaagg tggacgacag cttcttccac agactggaag agtccttcct ggtggaagag 360
gataagaagc acgagcggca ccccatcttc ggcaacatcg tggacgaggt ggcctaccac 420
gagaagtacc ccaccatcta ccacctgaga aagaaactgg tggacagcac cgacaaggcc 480
gacctgcggc tgatctatct ggccctggcc cacatgatca agttccgggg ccacttcctg 540
atcgagggcg acctgaaccc cgacaacagc gacgtggaca agctgttcat ccagctggtg 600
cagacctaca accagctgtt cgaggaaaac cccatcaacg ccagcggcgt ggacgccaag 660
gccatcctgt ctgccagact gagcaagagc agacggctgg aaaatctgat cgcccagctg 720
cccggcgaga agaagaatgg cctgttcggc aacctgattg ccctgagcct gggcctgacc 780
cccaacttca agagcaactt cgacctggcc gaggatgcca aactgcagct gagcaaggac 840
acctacgacg acgacctgga caacctgctg gcccagatcg gcgaccagta cgccgacctg 900
tttctggccg ccaagaacct gtccgacgcc atcctgctga gcgacatcct gagagtgaac 960
accgagatca ccaaggcccc cctgagcgcc tctatgatca agagatacga cgagcaccac 1020
caggacctga ccctgctgaa agctctcgtg cggcagcagc tgcctgagaa gtacaaagag 1080
attttcttcg accagagcaa gaacggctac gccggctaca ttgacggcgg agccagccag 1140
gaagagttct acaagttcat caagcccatc ctggaaaaga tggacggcac cgaggaactg 1200
ctcgtgaagc tgaacagaga ggacctgctg cggaagcagc ggaccttcga caacggcagc 1260
atcccccacc agatccacct gggagagctg cacgccattc tgcggcggca ggaagatttt 1320
tacccattcc tgaaggacaa ccgggaaaag atcgagaaga tcctgacctt ccgcatcccc 1380
tactacgtgg gccctctggc caggggaaac agcagattcg cctggatgac cagaaagagc 1440
gaggaaacca tcaccccctg gaacttcgag gaagtggtgg acaagggcgc ttccgcccag 1500
agcttcatcg agcggatgac caacttcgat aagaacctgc ccaacgagaa ggtgctgccc 1560
aagcacagcc tgctgtacga gtacttcacc gtgtataacg agctgaccaa agtgaaatac 1620
gtgaccgagg gaatgagaaa gcccgccttc ctgagcggcg agcagaaaaa ggccatcgtg 1680
gacctgctgt tcaagaccaa ccggaaagtg accgtgaagc agctgaaaga ggactacttc 1740
aagaaaatcg agtgcttcga ctccgtggaa atctccggcg tggaagatcg gttcaacgcc 1800
tccctgggca cataccacga tctgctgaaa attatcaagg acaaggactt cctggacaat 1860
gaggaaaacg aggacattct ggaagatatc gtgctgaccc tgacactgtt tgaggacaga 1920
gagatgatcg aggaacggct gaaaacctat gcccacctgt tcgacgacaa agtgatgaag 1980
cagctgaagc ggcggagata caccggctgg ggcaggctga gccggaagct gatcaacggc 2040
atccgggaca agcagtccgg caagacaatc ctggatttcc tgaagtccga cggcttcgcc 2100
aacagaaact tcatgcagct gatccacgac gacagcctga cctttaaaga ggacatccag 2160
aaagcccagg tgtccggcca gggcgatagc ctgcacgagc acattgccaa tctggccggc 2220
agccccgcca ttaagaaggg catcctgcag acagtgaagg tggtggacga gctcgtgaaa 2280
gtgatgggcc ggcacaagcc cgagaacatc gtgatcgaaa tggccagaga gaaccagacc 2340
acccagaagg gacagaagaa cagccgcgag agaatgaagc ggatcgaaga gggcatcaaa 2400
gagctgggca gccagatcct gaaagaacac cccgtggaaa acacccagct gcagaacgag 2460
aagctgtacc tgtactacct gcagaatggg cgggatatgt acgtggacca ggaactggac 2520
atcaaccggc tgtccgacta cgatgtggac gctatcgtgc ctcagagctt tctgaaggac 2580
gactccatcg acaacaaggt gctgaccaga agcgacaaga accggggcaa gagcgacaac 2640
gtgccctccg aagaggtcgt gaagaagatg aagaactact ggcggcagct gctgaacgcc 2700
aagctgatta cccagagaaa gttcgacaat ctgaccaagg ccgagagagg cggcctgagc 2760
gaactggata aggccggctt catcaagaga cagctggtgg aaacccggca gatcacaaag 2820
cacgtggcac agatcctgga ctcccggatg aacactaagt acgacgagaa tgacaagctg 2880
atccgggaag tgaaagtgat caccctgaag tccaagctgg tgtccgattt ccggaaggat 2940
ttccagtttt acaaagtgcg cgagatcaac aactaccacc acgcccacga cgcctacctg 3000
aacgccgtcg tgggaaccgc cctgatcaaa aagtacccta agctggaaag cgagttcgtg 3060
tacggcgact acaaggtgta cgacgtgcgg aagatgatcg ccaagagcga gcaggaaatc 3120
ggcaaggcta ccgccaagta cttcttctac agcaacatca tgaacttttt caagaccgag 3180
attaccctgg ccaacggcga gatccggaag cggcctctga tcgagacaaa cggcgaaacc 3240
ggggagatcg tgtgggataa gggccgggat tttgccaccg tgcggaaagt gctgagcatg 3300
ccccaagtga atatcgtgaa aaagaccgag gtgcagacag gcggcttcag caaagagtct 3360
atcctgccca agaggaacag cgataagctg atcgccagaa agaaggactg ggaccctaag 3420
aagtacggcg gcttcgacag ccccaccgtg gcctattctg tgctggtggt ggccaaagtg 3480
gaaaagggca agtccaagaa actgaagagt gtgaaagagc tgctggggat caccatcatg 3540
gaaagaagca gcttcgagaa gaatcccatc gactttctgg aagccaaggg ctacaaagaa 3600
gtgaaaaagg acctgatcat caagctgcct aagtactccc tgttcgagct ggaaaacggc 3660
cggaagagaa tgctggcctc tgccggcgaa ctgcagaagg gaaacgaact ggccctgccc 3720
tccaaatatg tgaacttcct gtacctggcc agccactatg agaagctgaa gggctccccc 3780
gaggataatg agcagaaaca gctgtttgtg gaacagcaca agcactacct ggacgagatc 3840
atcgagcaga tcagcgagtt ctccaagaga gtgatcctgg ccgacgctaa tctggacaaa 3900
gtgctgtccg cctacaacaa gcaccgggat aagcccatca gagagcaggc cgagaatatc 3960
atccacctgt ttaccctgac caatctggga gcccctgccg ccttcaagta ctttgacacc 4020
accatcgacc ggaagaggta caccagcacc aaagaggtgc tggacgccac cctgatccac 4080
cagagcatca ccggcctgta cgagacacgg atcgacctgt ctcagctggg aggcgac 4137

<210> SEQ ID NO 5

<211> LENGTH: 66
<212> TYPE: DNA
<213> ORGANISM: Artificial Sequence
<220> FEATURE:
<223> OTHER INFORMATION: Synthetic

<400> SEQUENCE: 5
ggatccggcg caacaaactt ctctctgctg aaacaagccg gagatgtcga agagaatcct 60
ggaccg 66

<210> SEQ ID NO 6
<211> LENGTH: 711
<212> TYPE: DNA
<213> ORGANISM: Artificial Sequence
<220> FEATURE:
<223> OTHER INFORMATION: Synthetic

<400> SEQUENCE: 6
agcaagggcg aggagctgtt caccggggtg gtgcccatcc tggtcgagct ggacggcgac 60
gtaaacggcc acaagttcag cgtgtccggc gagggcgagg gcgatgccac ctacggcaag 120
ctgaccctga agttcatctg caccaccggc aagctgcccg tgccctggcc caccctcgtg 180
accaccttcg gctacggcct gcagtgcttc gcccgctacc ccgaccacat gaagcagcac 240
gacttcttca agtccgccat gcccgaaggc tacgtccagg agcgcaccat cttcttcaag 300
gacgacggca actacaagac ccgcgccgag gtgaagttcg agggcgacac cctggtgaac 360
cgcatcgagc tgaagggcat cgacttcaag gaggacggca acatcctggg gcacaagctg 420
gagtacaact acaacagcca caacgtctat atcatggccg acaagcagaa gaacggcatc 480
aaggtgaact tcaagatccg ccacaacatc gaggacggca gcgtgcagct cgccgaccac 540
taccagcaga acacccccat cggcgacggc cccgtgctgc tgcccgacaa ccactacctg 600
agctaccagt ccgccctgag caaagacccc aacgagaagc gcgatcacat ggtcctgctg 660
gagttcgtga ccgccgccgg gatcactctc ggcatggacg agctgtacaa g 711

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
ggatcaggat caggatcagg a 21

<210> SEQ ID NO 8
<211> LENGTH: 204
<212> TYPE: DNA
<213> ORGANISM: Artificial Sequence
<220> FEATURE:
<223> OTHER INFORMATION: Synthetic

<400> SEQUENCE: 8
cgactgtgcc ttctagttgc cagccatctg ttgtttgccc ctcccccgtg ccttccttga 60
ccctggaagg tgccactccc actgtccttt cctaataaaa tgaggaaatt gcatcgcatt 120
gtctgagtag gtgtcattct attctggggg gtggggtggg gcaggacagc aagggggagg 180
attgggaaga caatagcagg catg 204

<210> SEQ ID NO 9
<211> LENGTH: 20

<212> TYPE: DNA
<213> ORGANISM: Artificial Sequence
<220> FEATURE:
<223> OTHER INFORMATION: Synthetic

<400> SEQUENCE: 9
ctgcaggtcg actctagaaa 20

<210> SEQ ID NO 10
<211> LENGTH: 19
<212> TYPE: DNA
<213> ORGANISM: Artificial Sequence
<220> FEATURE:
<223> OTHER INFORMATION: Synthetic

<400> SEQUENCE: 10
acatgaggat cacccatgt 19

<210> SEQ ID NO 11
<211> LENGTH: 25
<212> TYPE: DNA
<213> ORGANISM: Artificial Sequence
<220> FEATURE:
<223> OTHER INFORMATION: Synthetic

<400> SEQUENCE: 11
aagcagtggt atcaacgcag agtac 25

<210> SEQ ID NO 12
<211> LENGTH: 24
<212> TYPE: DNA
<213> ORGANISM: Artificial Sequence
<220> FEATURE:
<223> OTHER INFORMATION: Synthetic

<400> SEQUENCE: 12
ttgttgttgt tgttgttgtt tttt 24

<210> SEQ ID NO 13
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: n is a, c, g, or t

<400> SEQUENCE: 13
nnnnnnnnnn gacttggggg gaagcaggtg tatcaacgca gact 44

<210> SEQ ID NO 14
<211> LENGTH: 4
<212> TYPE: DNA
<213> ORGANISM: Artificial Sequence
<220> FEATURE:
<223> OTHER INFORMATION: Synthetic

<400> SEQUENCE: 14 ccch 4

<210> SEQ ID NO 15
<211> LENGTH: 12
<212> TYPE: DNA
<213> ORGANISM: Artificial Sequence
<220> FEATURE:

-continued

```
<223> OTHER INFORMATION: Synthetic

<400> SEQUENCE: 15

acttgtttaa gt                                                     12


<210> SEQ ID NO 16
<211> LENGTH: 16
<212> TYPE: DNA
<213> ORGANISM: Artificial Sequence
<220> FEATURE:
<223> OTHER INFORMATION: Synthetic

<400> SEQUENCE: 16

ggcaccgagt cggtgc                                                 16
```

CONSTRUCT FOR CONTINUOUS MONITORING OF LIVE CELLS

CROSS-REFERENCE TO RELATED APPLICATIONS

This application claims the benefit of International Patent Application No. PCT/US2020/025603, filed Mar. 29, 2020, which claims the benefit of U.S. Provisional Application No. 62/826,763 filed Mar. 29, 2019. The entire contents of the above-identified applications are hereby fully incorporated herein by reference.

STATEMENT REGARDING FEDERALLY SPONSORED RESEARCH

This invention was made with government support under Grant No. HL141005 awarded by National Institutes of Health. The government has certain rights in the invention.

REFERENCE TO AN ELECTRONIC SEQUENCE LISTING

The contents of the electronic sequence listing (“23430165_SequenceListing_ST25.txt”; Size 14,832 bytes and it was created on Jan. 13, 2026) are herein incorporated by reference in their entirety.

TECHNICAL FIELD

The subject matter disclosed herein is generally related to nucleic acid constructs for continuous monitoring of live cells. Specifically, the subject matter disclosed herein is directed to nucleic acid constructs that encode a fusion protein and a construct RNA sequence that induce live cells to self-report cellular contents while maintaining cell viability.

BACKGROUND

Single-cell gene expression (SCGE) profiling is an important analytical technique for the study of mammalian cells. The ability to obtain highly resolved molecular phenotypes directly from individual cells is transforming the way in which cell states are defined, cell circuitry is understood, and how cellular responses to environmental cues are studied. There is tremendous interest in moving beyond static snapshots of SCGE in cell suspensions to understand how SCGE profiles change over time. Technology that reports the internal state and functional history of cells within tissues would enable novel insight into dynamic biological processes. Current SCGE profiling technology addresses static heterogeneity (e.g. a snapshot of differences among single cells). However, dynamic signaling processes (Cai L, Nature 2008; Yosef N, Cell 2011; Yosef N, Nature 2013) and transitions in cell type and function over time are crucial to cellular biology and organism-level function. Enabling the comprehensive study of dynamic processes at the single-cell level is of intense interest, but tools for non-destructive in situ analysis are currently lacking. New methods are needed to obtain multiple information-rich samples at different time points from the same cell while minimally disrupting the cell. Retrieving RNA information from living systems grants insight into biological state and response. However, there are no non-destructive methods to continuously retrieve and monitor transcriptome-wide RNA information from the same living samples.

SUMMARY

In one aspect, the embodiments described herein are directed to nucleic acid constructs that encode a fusion protein and a construct RNA sequence. The fusion protein may comprise a secretion-inducing domain and a construct RNA capture domain that encodes less than about 400 amino acids, or about 20 to about 300 amino acids, or less than about 200 amino acids. When expressed in live cells the secretion domain induces the cell to export samples of cellular content that can be isolated and analyzed while maintaining cell viability. In certain example embodiments, the secretion domain facilitates the formation of an export compartment capable of packaging cellular contents and exporting those cellular contents from the cell.

The construct RNA capture domain of the fusion protein is one member of a binding pair that binds a corresponding RNA retrieval element on the expressed construct RNA sequence. The construct RNA sequence comprises a construct RNA retrieval element and a cellular RNA capture element. The construct RNA sequence may further comprise a barcode. The construct RNA retrieval element is recognized and bound by the construct RNA capture domain of the fusion protein. The cellular RNA capture domain hybridizes to cellular RNA. Binding of the construct RNA sequence/cellular RNA complex by the construct RNA capture element of the fusion protein results in export of the construct RNA sequence/cellular RNA complex in association with the secretion-inducing domain of the fusion protein. Thus, capture of cellular RNA by the construct RNA sequence enables export of the captured cellular RNA in association with the secretion-inducing domain of the fusion protein. In certain example embodiments, the secretion-inducing domain is a viral capsid or coat protein. In certain example embodiments, the secretion-inducing domain comprises a Gag protein or a functional fragment thereof.

In certain example embodiments, the construct RNA capture domain of the fusion protein. The nucleic acid construct of any one of the preceding claims wherein the construct RNA sequence encodes one or more CCCH ZnF. The nucleic acid may comprise a construct RNA sequence capture domain encoding a Poly(A) Binding Protein (PABP), Nab2 protein, or a fragment or variant thereof. In certain embodiments, the construct RNA sequence capture domain encodes a PABP capture domain optionally from human PABPC4, or a fragment or variant thereof. In embodiments, the Nab2 protein is from *S. cerevisiae* or *C. thermophilum*, and can comprise a construct RNA sequence encoding *S. cerevisiae* Nab2 ZnF 5-7 or *C. thermophilum* Nab2 ZnF 3-5. In an aspect, the Nab2 protein comprises a polynucleotide comprising about 59 amino acids of *S. cerevisiae* or a polynucleotide encoding about 56 amino acids of *C. thermophilum*

In certain embodiments, the construct RNA sequence is RRM1+RRM2 from human PABPC4. In embodiments, the construct RNA sequence comprises an RNP1 sequence motif, an RNP2 sequence motif, or a combination thereof, from an RNA Recognition Motif domain.

In certain example embodiments, the RNA construct may further comprise a barcode, and a poly U sequence or a sequence comprising a (UUG) n motif for capture of cellular RNA. The barcode comprises a randomized sequence unique to the construct and therefore to the cell or cell population the construct is delivered to. Thus, in certain example embodiments, all cellular RNA captured by the RNA construct and exported from the cell via the fusion protein will have the same barcode thereby identifying all cellular RNA exported from the same cell.

The nucleic acid constructs described herein may further comprise an inducible promoter to control expression of the fusion protein, and/or construct RNA sequence. In certain example embodiments, the promoter may be a tissue or cell-specific promoter. The nucleic acid constructs described herein may further comprise a steric linker. The steric linker may be located on a N-terminus of the secretion-inducing protein or between the secretion-inducing domain and the construct RNA capture domain and may control the rate of secretion, the size of export compartments formed by the secretion-inducing protein, or both. The nucleic acid constructs described herein may further encode a fusion protein that includes an affinity tag for subsequent isolation and enrichment of the fusion protein and/or export compartments formed by the fusion protein. Further, the nucleic acids constructs may encode a detectable self-reporting molecule that can be used to confirm successful delivery and expression of the nucleic acid constructs described herein. In certain example embodiments, the detectable self-reporting molecule may be a cleavable self-reporting molecule that can be cleaved from the RNA construct after expression.

In another aspect, the embodiments disclosed herein comprise methods for continuous monitoring of live cells comprising delivering into a cell a nucleic acid construct described herein. The nucleic acid construct is expressed, for example, via an inducible promoter. Cellular RNA, such as mRNA or microRNA, is captured by hybridization to the cellular RNA capture element of the construct RNA sequence. The captured cellular RNA is then exported from the cell by binding of the construct RNA capture domain of the fusion protein to the retrieval element of the construct RNA sequence such that the construct RNA sequence- and bound cellular RNA—are exported from the cell in association with secretion inducing domain of the cellular protein. The exported fusion protein/construct RNA sequence/cellular RNA complex may then be isolated.

In certain example embodiments, the method further comprises generating a RNA-DNA duplex by reverse transcribing the captured cellular RNA using the construct RNA sequence as a primer for reverse transcription. A DNA-DNA duplex is then generated by converting the construct RNA sequence to a corresponding DNA sequence with second strand synthesis using a DNA primer. The DNA-DNA duplex is then used to generate a sequencing library for sequencing using, for example, a NGS sequencing platform. Sequencing of the DNA-DNA duplex library identifies the transcript and—via the barcode information—the cell of origin for each transcript thereby enabling continuous single cell gene expression analysis.

In certain example embodiments, a nucleic acid construct for barcoding cellular components, such as expressed RNAs, comprises a barcode and a cellular RNA capture element. In certain example embodiments, the cellular RNA capture element is a poly(U) or (UUG). motif. In certain example embodiments, the nucleic acid construct may further comprise a filter sequence (SEQ ID NO: 13) that helps identify the barcode sequence in downstream sequencing reads. In certain example embodiments, the nucleic acid construct may comprise an adapter sequence that provides a complementary binding site for a reverse transcription or amplification primer. In certain other example embodiments, the nucleic acid construct may further comprise a sequencing primer binding site that is complementary to one or more sequencing primers used in downstream sequencing reactions. The nucleic acid constructs described in this paragraph may be used as the construct RNA sequence in relation to the self-reporting export compartment embodiments discussed above.

In another aspect, a method for labeling molecular components of cells according to cell or origin comprises expressing any of the above disclosed nucleic acid constructs in one or more cells, wherein the expressed nucleic acid construct comprises a barcode that is unique to an individual cell or cell lineage, capturing cellular RNA expressed in the one or more cells by binding of the cellular RNA via the cellular RNA capture element of the expressed construct sequence and incorporating the barcode of the expressed nucleic acid construct to the captured cellular RNA to generate barcoded cellular RNA. Barcoded RNA refers to directly barcoded RNAs as well as single and double stranded copies made from the original cellular RNA such as those shown in FIGS. 12-15. The barcode may be attached by ligation of the nucleic acid construct to the cellular RNA by RNA-RNA ligation, by priming first and/or second strand synthesis of the captured cellular RNA using the expressed nucleic acid construct. Barcoded RNA may be further amplified, for example, by RNA-dependent RNA synthesis, PCR, or linear DNA amplification.

In another aspect, the embodiments disclosed herein comprise vectors comprising the nucleic acid constructs described herein. In certain example embodiments, the vectors are viral vectors. In certain other example embodiments, the vectors are non-viral vectors.

In another aspect, embodiments disclosed herein include kits comprising the nucleic acid constructs and/or vectors described herein.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 10—is a table showing projected achievable time resolution of gene expression using the constructs described herein.

FIG. 16B Pol III driven RNA barcodes transcripts contain a 5' rev response element and are co-expressed with Rev viral proteins for nuclear export. RNA barcode transcripts are engineered with MS2 hairpins for binding to the MS2 coat protein (MCP) domain within gag-MCP fusion proteins. Barcodes are expressed within wild-type gag expressing cells (to serve as a measure of background export) and within gag-MCP expressing cells for directed export within gag-MCP VLPs. Barcodes either contain a 3' poly(U) tail for hybridizing to polyadenylated RNAs or a scrambled 3' tail as a hybridization control. FIG. 16C Gag-MCP VLPs successfully package and export endogenous mRNA, as measured by GAPDH RT-qPCR.

(FIG. 2611) RNA-seq on supernatants purified for immunoprecipitation input. (FIG. 261) RNA-seq on supernatants purified via flag immunoprecipitation. (FIG. 26M-FIG. 26O) RNA-seq sample representation.

(FIG. 27B) RNA-seq on purified supernatants for various stably transduced 293T cell lines, compared to wild-type 293T cells. (FIG. 27C) RNA-seq on purified supernatants for various stably transduced HT1080 cell lines, compared to wild-type HT1080 cells. (FIG. 27D) RNA-seq replicate concordance of purified supernatant from wild-type 293T cells. (FIG. 27E) RNA-seq replicate concordance of purified supernatant from Gag+293T cells. (FIG. 27F) RNA-seq replicate concordance of purified supernatant from Gag-RRM+293T cells. (FIG. 27G-FIG. 271) RNA-seq sample representation. (FIG. 27J) RNA localization importance in predicting supernatant abundance using a gradient boosted tree model. (FIG. 27K) Principal components analysis on different cell lines with different constructs, showing cell line separation for Gag+ and Gag-RRM+ cell lines.

DETAILED DESCRIPTION OF THE EXAMPLE EMBODIMENTS

General Definitions

Figure 1:
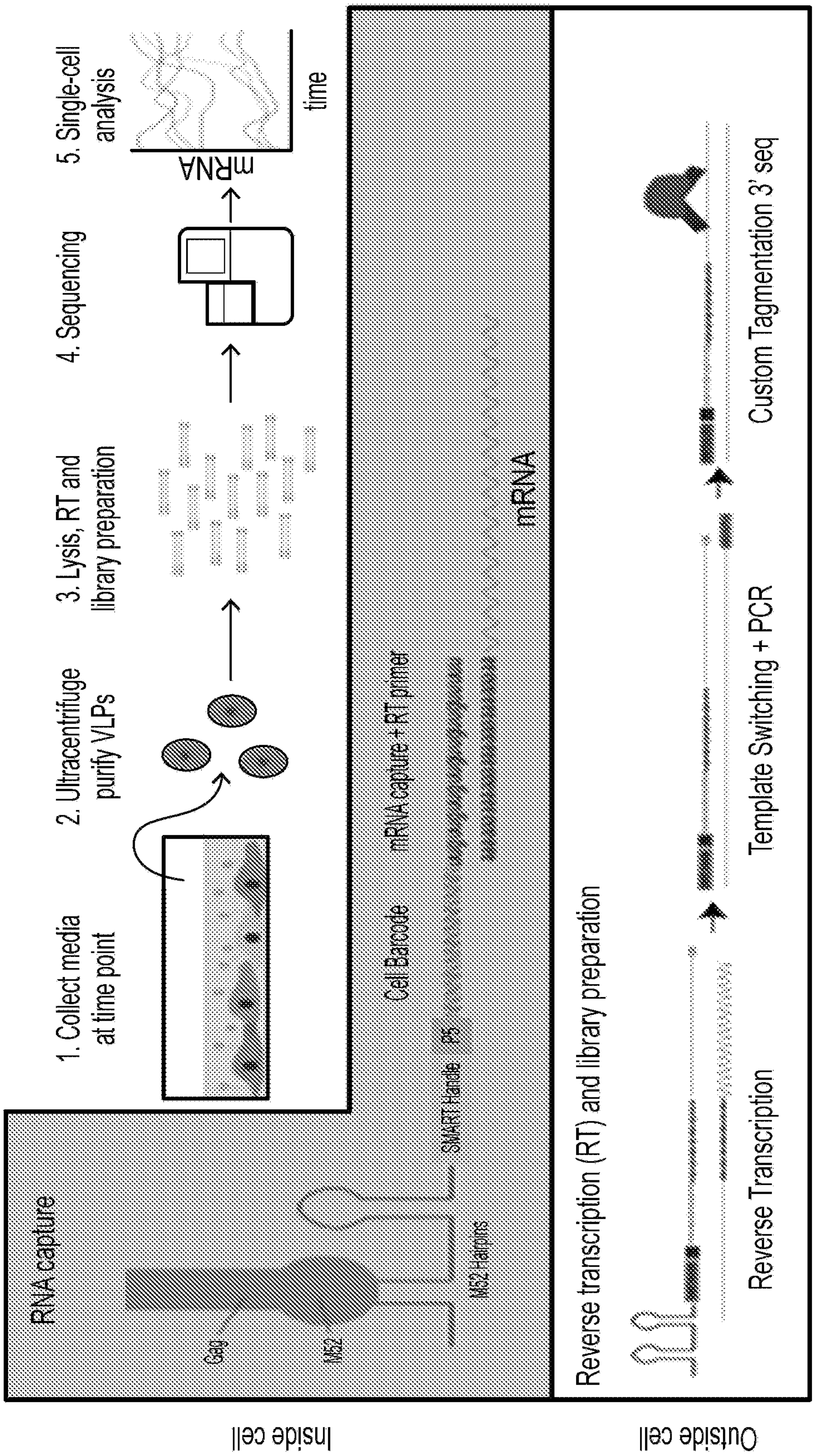
FIG. 1—is a schematic depicting a method for continuous single cell gene expression analysis of live cells, in accordance with certain example embodiments.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms “a”, “an”, and “the” include both singular and plural referents unless the context clearly dictates otherwise.

The term “optional” or “optionally” means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms “about” or “approximately” as used herein when referring to a measurable value such as a parameter, an amount, a temporal duration, and the like, are meant to encompass variations of and from the specified value, such as variations of +1-10% or less, +7-5% or less, +/−1°/0 or less, and +7-0.1% or less of and from the specified value, insofar such variations are appropriate to perform in the disclosed invention. It is to be understood that the value to which the modifier “about” or “approximately” refers is itself also specifically, and preferably, disclosed.

Reference throughout this specification to “one embodiment”, “an embodiment,” “an example embodiment,” means that a particular feature, structure or characteristic described in connection with the embodiment is included in at least one embodiment of the present invention. Thus, appearances of the phrases “in one embodiment,” “in an embodiment,” or “an example embodiment” in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference. Reference is made to U.S. Provisional Application No. 62,397,867 filed on Sep. 21, 2016, and International Patent Publication WO2018/057812.

Overview

Embodiments disclosed herein provide nucleic acid constructs and methods of use thereof that induce a live cell to self-report sub-samples of cellular content. The construct provided herein surprisingly allows for improved RNA exports with smaller RNA capture domains encoded in the nucleic acid constructs. The sampling can be general or can be targeted to a particular class of molecules or to specific types of molecules. The constructs facilitate generation of a read-out for high-throughput screens by combining engineered export with simple bulk sample and sample processing. Live cell sampling enables time course measurements and expands, for example, the applicability of transcriptional profiles obtained by single cell gene expression analysis. The constructs may further comprise steric linkers, inducible promoters, detectable self-reporting molecules, and affinity elements as discussed in further detail below. When introduced into live cells the constructs disclosed herein enable live cell sampling of cellular contents while maintaining cell viability. Cellular contents may include nuclear as well as cytosolic contents. In addition, the nucleic acid constructs and methods further comprise the use of nucleic acid barcodes that tag each transcript molecule with a cell-identifying barcode, adding single-cell transcriptomic analysis to the self-reporting approach disclosed herein. In certain example embodiments, the nucleic acid constructs comprise a nucleic acid sequence encoding a fusion protein and a construct RNA sequence. The fusion protein comprises a secretion-inducing domain and a construct RNA capture domain. A secretion-inducing domain may comprise a polypeptide that when expressed induces a cell to export cellular contents in association with the secretion-inducing domain. As used herein, and in the context of proteins encoded by the nucleic acid constructs described herein, a “protein” may refer to the full-length sequence of the protein or only that portion of the protein that is necessary for the function for which the full-length protein is otherwise expressed.

Fusion Protein

The nucleic acid constructs comprise sequences encoding a fusion protein. The fusion proteins disclosed herein comprise a secretion-inducing domain and a construct RNA capture domain. The secretion inducing domain is included such that when expressed induces the export of cellular contents in association with the domain. The construct RNA capture domain may be a protein or peptide that recognizes and binds a retrieval element of the construct RNA sequence after expression of the construct RNA sequence in the cell.

Secretion Inducing Domain

In certain example embodiments, the secretion-inducing domain, or protein, may comprise a polypeptide that when expressed induces a cell to export cellular contents in association with the secretion-inducing domain. In an aspect, the polypeptide is an export compartment protein.

An export compartment protein may be any protein that self-assembles upon expression in a cell into an export compartment. In certain example embodiments, an export compartment is a spherical macromolecular assembly comprising a protein inner layer and an outer lipid containing membrane, with at least the export-compartment protein forming the inner protein layer. In certain example embodiments, the export compartment protein may only form a partial export compartment while retaining the ability to associate with and export the targeted cellular contents. In certain example embodiments, the export compartment protein is a viral export compartment protein that forms virus-like particles. Regarding embodiments that use viral export compartment proteins, the terms export compartment and virus-like particle (VLP) may be used interchangeably. Example viral export compartment proteins may include viral capsid proteins. In certain example embodiments, the viral capsid protein is a viral Gag protein. In certain example embodiments, the viral Gag protein is a lentivirus Gag protein. In certain example embodiments, the export compartment protein is encoded by a nucleic acid sequence of SEQ ID NO: 1.

Construct RNA Capture Domain

The construct RNA capture domain may be a protein or peptide that recognizes and binds a retrieval element of the construct RNA sequence after expression of the construct RNA sequence in the cell. The construct RNA capture domain of the fusion protein may comprise any protein or peptide that recognizes and selectively binds a target sequence or structural feature of the expressed construct RNA sequence, or a fragment or variant thereof. In embodiments, the construct RNA capture domain is less than about 600 amino acids, less than about 500 amino acids, less than about 400 amino acids, less than about 300 amino acids, less than about 200 amino acids, or less than about 100 amino acids.

The proteins referred to herein also encompasses a functional variant of the protein or a homologue or an orthologue thereof. A "functional variant" of a protein as used herein refers to a variant of such protein which retains at least partial activity of that protein. Functional variants may include mutants (which may be insertion, deletion, or replacement mutants), including polymorphs, etc., including as discussed herein.

In embodiments, the RNA capture domain can comprise one or more CCCH Zn fingers (SEQ ID NO: 14). In embodiments, the RNA capture domain comprises tandem CCCH zinc fingers (SEQ ID NO: 14), which may comprise 2, 3, 4, 5, 6, 7, up to 10 Zn fingers in tandem. In certain embodiments, the zinc fingers may interact with one another as exemplified in NGF1-A-binding protein 2 (Nab2), or may by structurally independent or comprise a head-to-tail arrangement as in TIS11d or MBNL1, respectively.

The construct RNA capture domain may comprise a NGF1-A-binding protein 2 (Nab 2) protein, which may comprise CCCH zinc fingers (SEQ ID NO: 14), or a fragment or variant thereof. In embodiments, the construct RNA capture domain comprises a Nab2 protein from *S. cerevisiae* or *C. thermophilus*, or a fragment or variant thereof.

The Nab2 protein, fragment or variant thereof, may comprise ZnFs 5-7 (ZnF5-7) of *S. cerevisiae*. In embodiments, the Nab2 protein comprises at least 50%, 60%, 70%, 80%, 90%, 95%, 96° A), 97%, 98%, 99%, or complete identity with amino acid residues 409-483 of the Nab2 protein of *S. cerevisiae*, or nucleotides 410-480. In embodiments, the Nab2 protein, fragment or variant thereof, comprises nucleotides 414-431, corresponding to ZnF5, nucleotides 436-553, corresponding to ZnF6, and/or nucleotides 457-474 corresponding to ZnF7 of *S. cerevisiae*. See, Brockmann, et al., Structure, 20:6, 6 Jun. 2012, 1007-1018; DOI: 10.1016/j.str.2012.03.011. Fragment and variants comprising amino acid residues homologous to one or more of ZnF5-7 are also envisioned for use herein.

The Nab2 protein, fragment or variant thereof, may comprise Zn fingers 3-5 of *Chaetomium thermophilum*. See, e.g. Kuhlmann et al., Nucleic Acids Res. 2014 Jan. 1: 42 (1): 672-680; DOI: 10.193/nar/gkt876. In embodiments, the Nab2 protein comprises at least 50%, 60%, 70%, 80%, 90%, 95%, 96%, 97%, 98%, 99%, or complete identity with amino acid residues 401-466 of the Nab2 protein of *C. thermophilum*.

In embodiments, the RNA capture domain comprises a variant or fragment of Poly(A) Binding Protein (PABP). In embodiments, the RNA capture domain comprises RNA recognition motifs 1 and 2 (RRM1-2) of PABP. Safaee, 4 Oct. 2012, Mol. Cell, 48:3, 375-386; DOI: 10.1016/j.molcel.2012.09.001, incorporated herein by reference. The RRM1 and RRM2 domains of PABP are highly conserved among RRM domains, that comprise sheets comprised of two sequence motifs (RNP1 and RNP2) of the sheets responsible for RNA binding. Accordingly, in some embodiments, the RNA capture domain comprises one or more RNP1 sequence motif, one or more RNP2 sequence motif, or a combination thereof. In embodiments, the RNA capture domain may comprise p sheets of an RRM domain. RRM domains from PABP of species are contemplated for use herein; in certain embodiments, the PABP peptide, fragment or variant thereof is human PABP, particularly preferred is PAPBC4.

As disclosed herein, fusing the variant or fragment poly (A) binding domains to gag shows an increase in exported RNA, with more RNA information obtained per sample. Accordingly, in embodiments, the RNA capture domain is less than about 600 amino acids, less than about 400 amino acids, or less than about 300 amino acids, and allows an increase in exported RNA, provides more RNA information per sample, or a combination thereof, relative to the use of a larger RNA capture domain, e.g. larger than about 300 amino acids, 400 amino acids, 500 amino acids, or 600 amino acids. Advantageously, and as shown in the examples and disclosure herein, these RNA capture domains do not perturb cells via RNA Seq, while providing advantages of increased exported RNA and/or more RNA information per sample. In an aspect, the construct RNA capture domain is configured to associate, bind or otherwise capture a particular sequence or structural feature of the RNA. In certain example embodiments, the construct RNA capture domain may be a protein or peptide that recognizes and binds RNA secondary structural features, such as but not limited to, hairpins. In certain example embodiments, the construct RNA capture domain comprises a catalytically dead Cas protein (dCas), in particular, a dCas9 protein, and the retrieval element of the construct RNA sequence may comprise a sequence encoding the dCas9-binding hairpin. In certain example embodiments, the Cas protein may be a catalytically dead Cas protein ("dCas") and/or have nickase activity. Methods for generating catalytically dead Cas9 or a nickase Cas9 (WO 2014/204725, Ran et al. Cell. 2013 Sep. 12; 154 (6): 1380-1389), Cas12 (Liu et al. Nature Communications, 8, 2095 (2017), and Cas13 (International Patent Publication Nos. WO 2019/005884 and WO2019/060746) are known in the art and incorporated herein by reference. In certain embodiments, the dCas provide a sequence specific targeting functionality that delivers the functional domain to or proximate a target sequence. Example functional domains that may be fused to, operably coupled to, or otherwise associated with a Cas protein can be or include, but are not limited to a nuclear localization signal (NLS) domain, a nuclear export signal (NES) domain, a translational activation domain, a transcriptional activation domain (e.g. VP64, p65, MyoD1, HSF1, RTA, and SETT/9), a translation initiation domain, a transcriptional repression domain (e.g., a KRAB domain, NuE domain, NcoR domain, and a SID domain such as a SID4X domain), a nuclease domain (e.g., FokI), a histone modification domain (e.g., a histone acetyltransferase), a light inducible/controllable domain, a chemically inducible/controllable domain, a and combinations thereof. Additional dCas9-binding hairpins and design considerations can be found, for example at Kocak, et al., Nat Biotechnol. 2019 June: 37 (6): 657-666; doi: 10.1038/s41587-019-0095-1. The invention further comprehends the Cas protein being codon optimized for expression in a eukaryotic cell. In a preferred embodiment the eukaryotic cell is a mammalian cell, a plant cell or a yeast cell and in a more preferred embodiment the mammalian cell is a human cell. In a further embodiment of the invention, the expression of the gene product is decreased. In some embodiments the CRISPR protein is Cas9. In some embodiments the CRISPR protein is Cas12a. In some embodiments, the Cas12a protein is Acidaminococcus sp. BV3L6, Lachnospiraceae bacterium or *Francisella Novicida* Cas12a, and may include mutated Cas12a derived from these organisms. The protein may be a further Cas9 or Cas12a homolog or ortholog. In some embodiments, the nucleotide sequence encoding the Cas9 or Cas12a protein is codon-optimized for expression in a eukaryotic cell.

In certain other example embodiments, the construct RNA capture domain of the fusion protein may be a viral capsid protein that binds a sequence or structural feature of the corresponding viral genome. For example, the construct RNA capture domain may be a MS2 coat protein and the retrieval element of the construct RNA sequence may comprise a RNA sequence defining a MS2 hairpin. In certain example embodiments, the construct RNA capture domain comprises a protein encoded by SEQ ID NO: 2, SEQ ID NO: 3, or SEQ ID NO: 4, or functional equivalents thereof. In certain example embodiments, the retrieval element of the construct RNA sequence comprises SEQ ID NO: 10.

Construct RNA Sequence

The construct RNA sequence, as described above, can be configured to comprise a sequence that is capable of binding the RNA capture domain of the fusion protein of the nucleic acid constructs described herein, such a sequence is referred to herein as a retrieval element. In an aspect, the construct RNA sequence comprises a secondary structure or other feature that allows for the recognition and binding of the construct RNA sequence by the RNA capture domain. In an example embodiment, the construct RNA sequence is an MS2 hairpin or a guide RNA sequence. The construct RNA sequence comprises a retrieval element and a cellular RNA capture element. The construct RNA may also further comprise a reverse transcription primer binding site and a barcode. The construct RNA retrieval element is recognized and bound by the construct RNA capture domain on the fusion protein such that the construct RNA is exported from the cell in association with the secretion-inducing protein. In certain example embodiments, the secretion-inducing protein is an export compartment protein and the construct RNA is packaged within the export compartment formed by the fusion protein. In certain embodiments, the construct RNA sequence can further comprise barcodes, cellular RNA capture elements, unique molecular identifiers, primer sequences, and other adapter molecules that can be useful upon export of the cellular RNA and subsequent building and/or sequencing of libraries.

Guide RNA

In an aspect, the retrieval element on the construct RNA is a dCas9 guide RNA sequence. The dCas9 guide RNA sequence can be configured with particular secondary structural features such as hairpins that allow for the retrieval by the binding of the dCas protein. In certain example embodiments, the construct RNA capture domain may be a protein or peptide that recognizes and binds RNA secondary structural features, such as but not limited to, hairpins. As used herein, the term "crRNA" or "guide RNA" or "single guide RNA" or "sgRNA" or "one or more nucleic acid components" of a Type V or Type VI CRISPR-Cas locus effector protein comprises any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), CLUSTALW™, CLUSTAL X™, BLAT™, NNOVOALIGN™ (NOVOCRAFT® Technologies, ELAND™ (ILLUMINA®, San Diego, CA), SOAP™, and MAQ™. The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide may be selected to target any target nucleic acid sequence. The target sequence may be DNA. The target sequence may be any RNA sequence. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within a RNA molecule selected from the group consisting of mRNA, pre-mRNA, and rRNA. In some preferred embodiments, the target sequence may be a sequence within a RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106 (1): 23-24; and PA Carr and GM Church, 2009, Nature Biotechnology 27 (12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence.

In general, degree of complementarity is with reference to the optimal alignment of the sca sequence and tracr sequence, along the length of the shorter of the two sequences. Optimal alignment may be determined by any suitable alignment algorithm, and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In general, the CRISPR-Cas, CRISPR-Cas9 or CRISPR system may be as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, in particular a Cas9 gene in the case of CRISPR-Cas9, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. The section of the guide sequence through which complementarity to the target sequence is important for cleavage activity is referred to herein as the seed sequence. A target sequence may comprise any polynucleotide, such as DNA or RNA polynucleotides. In some embodiments, a target sequence is located in the nucleus or cytoplasm of a cell, and may include nucleic acids in or from mitochondrial, organelles, vesicles, liposomes or particles present within the cell. In some embodiments, especially for non-nuclear uses, NLSs are not preferred. In some embodiments, a CRISPR system comprises one or more nuclear exports signals (NESs). In some embodiments, a CRISPR system comprises one or more NLSs and one or more NESs. In some embodiments, direct repeats may be identified in silico by searching for repetitive motifs that fulfill any or all of the following criteria: 1. found in a 2Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), CLUSTALW™, CLUSTAL X™, BLAT™, NNOVOALIGN™ (NOVOCRAFT® Technologies, ELAND™ (ILLUMINA®, San Diego, CA), SOAP™, and MAQ™. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments of CRISPR-Cas systems, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83°4-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In particularly preferred embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e. an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and tracr sequence, the length of each RNA may be optimized to be shortened from their respective native lengths, and each may be independently chemically modified to protect from degradation by cellular RNase or otherwise increase stability.

In some embodiments, the loop of the 5'-handle of the guide is modified. In some embodiments, the loop of the 5'-handle of the guide is modified to have a deletion, an insertion, a split, or chemical modifications. In certain embodiments, the loop comprises 3, 4, or 5 nucleotides. In certain embodiments, the loop comprises the sequence of UCUU, UUUU, UAUU, or UGUU. In some embodiments, the guide molecule forms a stemloop with a separate non-covalently linked sequence, which can be DNA or RNA.

In some embodiments, the tracr and tracr mate sequences can be covalently linked via a linker (e.g., a non-nucleotide loop) that comprises a moiety such as spacers, attachments, bioconjugates, chromophores, reporter groups, dye labeled RNAs, and non-naturally occurring nucleotide analogues. More specifically, suitable spacers for purposes of this invention include, but are not limited to, polyethers (e.g., polyethylene glycols, polyalcohols, polypropylene glycol or mixtures of ethylene and propylene glycols), polyamines group (e.g., spennine, spermidine and polymeric derivatives thereof), polyesters (e.g., poly(ethyl acrylate)), polyphosphodiesters, alkylenes, and combinations thereof. Suitable attachments include any moiety that can be added to the linker to add additional properties to the linker, such as but not limited to, fluorescent labels. Suitable bioconjugates include, but are not limited to, peptides, glycosides, lipids, cholesterol, phospholipids, diacyl glycerols and dialkyl glycerols, fatty acids, hydrocarbons, enzyme substrates, steroids, biotin, digoxigenin, carbohydrates, polysaccharides. Suitable chromophores, reporter groups, and dye-labeled RNAs include, but are not limited to, fluorescent dyes such as fluorescein and rhodamine, chemiluminescent, electrochemiluminescent, and bioluminescent marker compounds. The design of example linkers conjugating two RNA components are also described in WO 2004/015075.

The linker (e.g., a non-nucleotide loop) can be of any length. In some embodiments, the linker has a length equivalent to about 0-16 nucleotides. In some embodiments, the linker has a length equivalent to about 0-8 nucleotides. In some embodiments, the linker has a length equivalent to about 0-4 nucleotides. In some embodiments, the linker has a length equivalent to about 2 nucleotides. Example linker design is also described in WO2011/008730.

A typical Type II Cas9 sgRNA comprises (in 5' to 3' direction): a guide sequence, a poly U tract, a first complimentary stretch (the "repeat"), a loop (tetraloop), a second complimentary stretch (the "anti-repeat" being complimentary to the repeat), a stem, and further stem loops and stems and a poly A (often poly U in RNA) tail (terminator). In preferred embodiments, certain aspects of guide architecture are retained, certain aspect of guide architecture cam be modified, for example by addition, subtraction, or substitution of features, whereas certain other aspects of guide architecture are maintained. Preferred locations for engineered sgRNA modifications, including but not limited to insertions, deletions, and substitutions include guide termini and regions of the sgRNA that are exposed when complexed with CRISPR protein and/or target, for example the tetraloop and/or loop2.

In certain embodiments, guides of the invention comprise specific binding sites (e.g. aptamers) for adapter proteins, which may comprise one or more functional domains (e.g. via fusion protein). When such a guides forms a CRISPR complex (i.e. CRISPR enzyme binding to guide and target) the adapter proteins bind and, the functional domain associated with the adapter protein is positioned in a spatial orientation which is advantageous for the attributed function to be effective.

In an embodiment of the invention, modification of guide architecture comprises replacing bases in stemloop 2. For example, in some embodiments, "actt" ("acuu" in RNA) and "aagt" ("aagu" in RNA) bases in stemloop2 are replaced with "cgcc" and "gcgg". In some embodiments, "actt" and "aagt" bases in stemloop2 are replaced with complimentary GC-rich regions of 4 nucleotides. In some embodiments, the complimentary GC-rich regions of 4 nucleotides are "cgcc" and "gcgg" (both in 5' to 3' direction). In some embodiments, the complimentary GC-rich regions of 4 nucleotides are "gcgg" and "cgcc" (both in 5' to 3' direction). Other combination of C and G in the complimentary GC-rich regions of 4 nucleotides will be apparent including CCCC and GGGG.

In one aspect, the stemloop 2, e.g., "ACTTgtttAAGT" (SEQ ID NO: 15) can be replaced by any "XXXXgtttYYYY", e.g., where XXXX and YYYY represent any complementary sets of nucleotides that together will base pair to each other to create a stem.

In one aspect, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-12 and Y2-12 (wherein X and Y represent any complementary set of nucleotides) may be contemplated. In one aspect, the stem made of the X and Y nucleotides, together with the "gttt," will form a complete hairpin in the overall secondary structure; and, this may be advantageous and the amount of base pairs can be any amount that forms a complete hairpin. In one aspect, any complementary X: Y basepairing sequence (e.g., as to length) is tolerated, so long as the secondary structure of the entire sgRNA is preserved. In one aspect, the stem can be a form of X: Y basepairing that does not disrupt the secondary structure of the whole sgRNA in that it has a DR: tracr duplex, and 3 stemloops. In one aspect, the "gttt" tetraloop that connects ACTT and AAGT (or any alternative stem made of X: Y basepairs) can be any sequence of the same length (e.g., 4 basepair) or longer that does not interrupt the overall secondary structure of the sgRNA. In one aspect, the stemloop can be something that further lengthens stemloop2, e.g. can be MS2 aptamer. In one aspect, the stemloop3 "GGCACCGagtCGGTGC" (SEQ ID NO:16) can likewise take on a "XXXXXXXagtYYYYYYY" form, e.g., wherein X7 and Y7 represent any complementary sets of nucleotides that together will base pair to each other to create a stem. In one aspect, the stem comprises about 7 bp comprising complementary X and Y sequences, although stems of more or fewer basepairs are also contemplated. In one aspect, the stem made of the X and Y nucleotides, together with the "agt", will form a complete hairpin in the overall secondary structure. In one aspect, any complementary X: Y basepairing sequence is tolerated, so long as the secondary structure of the entire sgRNA is preserved. In one aspect, the stem can be a form of X: Y basepairing that doesn't disrupt the secondary structure of the whole sgRNA in that it has a DR: tracr duplex, and 3 stemloops. In one aspect, the "agt" sequence of the stemloop 3 can be extended or be replaced by an aptamer, e.g., a MS2 aptamer or sequence that otherwise generally preserves the architecture of stemloop3. In one aspect for alternative Stemloops 2 and/or 3, each X and Y pair can refer to any basepair. In one aspect, non-Watson Crick basepairing is contemplated, where such pairing otherwise generally preserves the architecture of the stemloop at that position.

In one aspect, the DR: tracrRNA duplex can be replaced with the form: gYYYYag (N) NNNNxxxxNNNN (AAN) uuRRRRu (using standard IUPAC nomenclature for nucleotides), wherein (N) and (AAN) represent part of the bulge in the duplex, and "xxxx" represents a linker sequence. NNNN on the direct repeat can be anything so long as it basepairs with the corresponding NNNN portion of the tracrRNA. In one aspect, the DR: tracrRNA duplex can be connected by a linker of any length (xxxx . . . ), any base composition, as long as it doesn't alter the overall structure.

In one aspect, the sgRNA structural requirement is to have a duplex and 3 stemloops. In most aspects, the actual sequence requirement for many of the particular base requirements are lax, in that the architecture of the DR: tracrRNA duplex should be preserved, but the sequence that creates the architecture, i.e., the stems, loops, bulges, etc., may be altered.

To increase the effectiveness of gRNA, for example gRNA delivered with viral or non-viral technologies, Applicants added secondary structures into the gRNA that enhance its stability and improve gene editing. Separately, to overcome the lack of effective delivery, Applicants modified gRNAs with cell penetrating RNA aptamers; the aptamers bind to cell surface receptors and promote the entry of gRNAs into cells. Notably, the cell-penetrating aptamers can be designed to target specific cell receptors, in order to mediate cell-specific delivery. Applicants also have created guides that are inducible.

Light responsiveness of an inducible system may be achieved via the activation and binding of cryptochrome-2 and CIB1. Blue light stimulation induces an activating conformational change in cryptochrome-2, resulting in recruitment of its binding partner C1B1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 $mW/cm^2$. In a preferred embodiment, a stimulation paradigm of as low as 0.25 sec every 15 sec should result in maximal activation. The chemical or energy sensitive guide may undergo a conformational change upon induction by the binding of a chemical source or by the energy allowing it act as a guide and have the Cas9 CRISPR-Cas system or complex function. The invention can involve applying the chemical source or energy so as to have the guide function and the Cas9 CRISPR-Cas system or complex function; and optionally further determining that the expression of the genomic locus is altered.

There are several different designs of this chemical inducible system: 1. ABI-PYL based system inducible by Absci sic Acid (ABA), 2. FKBP-FRB based system inducible by rapamycin (or related chemicals based on rapamycin), 3. GID1-GM based system inducible by
Gibberellin (GA)

Another system contemplated by the present invention is a chemical inducible system based on change in sub-cellular localization. Applicants also developed a system in which the polypeptide include a DNA binding domain comprising at least five or more Transcription activator-like effector (TALE) monomers and at least one or more half-monomers specifically ordered to target the genomic locus of interest linked to at least one or more effector domains are further linker to a chemical or energy sensitive protein. This protein will lead to a change in the sub-cellular localization of the entire polypeptide (i.e. transportation of the entire polypeptide from cytoplasm into the nucleus of the cells) upon the binding of a chemical or energy transfer to the chemical or energy sensitive protein. This transportation of the entire polypeptide from one sub-cellular compartments or organelles, in which its activity is sequestered due to lack of substrate for the effector domain, into another one in which the substrate is present would allow the entire polypeptide to come in contact with its desired substrate (i.e. genomic DNA in the mammalian nucleus).

A chemical inducible system can be an estrogen receptor (ER) based system inducible by 4-hydroxytamoxifen (4OHT). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave. These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas9 CRISPR-Cas complex or system, and the binding will induce the change of sub-cellular localization of the polypeptide, leading to the entire polypeptide entering the nucleus of cells. Once inside the nucleus, the guide protein and the other components of the Cas9 CRISPR-Cas complex will be active.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 μs and 500 milliseconds, preferably between 1 gs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of GENETRONICS®, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100.mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm$^2$ to about 100 W/cm$^2$. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 KHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm$^2$ (FDA recommendation), although energy densities of up to 750 mW/cm$^2$ have been used. In physiotherapy, ultrasound is typically used as an energy source in a range up to about 3 to 4 W/cm$^2$ (WHO recommendation). In other therapeutic applications, higher intensities of ultrasound may be employed, for example, HIFU at 100 W/cm up to 1 kW/cm$^2$ (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm'. Even more preferably, the exposure to an ultrasound energy source is at a power density of from about 1 to about 15 Wcm$^{-2}$.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05/cm-2 to about 10 Wcm$^{-2}$ with a frequency ranging from about 0.015 to about 10 MHz (see WO 98/52609). However, alternatives are also possible, for example, exposure to an ultrasound energy source at an acoustic power density of above 100 Wcm$^{-2}$, but for reduced periods of time, for example, 1000 Wcm$^{-2}$ for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm$^{-2}$ or 1.25 Wcm$^{-2}$ as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

Photoinducibility provides the potential for spatial precision. Taking advantage of the development of optrode technology, a stimulating fiber optic lead may be placed in a precise brain region. Stimulation region size may then be tuned by light intensity. This may be done in conjunction with the delivery of the Cas9 CRISPR-Cas system or complex of the invention, or, in the case of transgenic Cas9 animals, guide RNA of the invention may be delivered and the optrode technology can allow for the modulation of gene expression in precise brain regions. A transparent Cas9 expressing organism, can have guide RNA of the invention administered to it and then there can be extremely precise laser induced local gene expression changes.

Aspects of the invention encompass a non-naturally occurring or engineered composition that may comprise a guide RNA (gRNA) comprising a guide sequence capable of hybridizing to a target sequence in a genomic locus of interest in a cell and a Cas9 enzyme as defined herein that may comprise at least one or more nuclear localization sequences.

Thus, gRNA, the CRISPR enzyme as defined herein may each individually be comprised in a composition and administered to a host individually or collectively. Alternatively, these components may be provided in a single composition for administration to a host. Administration to a host may be performed via viral vectors known to the skilled person or described herein for delivery to a host (e.g., lentiviral vector, adenoviral vector, AAV vector). As explained herein, use of different selection markers (e.g., for lentiviral sgRNA selection) and concentration of gRNA (e.g., dependent on whether multiple gRNAs are used) may be advantageous for eliciting an improved effect. On the basis of this concept, several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. The compositions may be applied in a wide variety of methods for screening in libraries in cells and functional modeling in vivo (e.g., gene activation of lincRNA and identification of function; gain-of-function modeling; loss-of-function modeling; the use the compositions of the invention to establish cell lines and transgenic animals for optimization and screening purposes).

In another embodiment, the Cas9 is delivered into the cell as a protein. In another and particularly preferred embodiment, the Cas9 is delivered into the cell as a protein or as a nucleotide sequence encoding it. Delivery to the cell as a protein may include delivery of a Ribonucleoprotein (RNP) complex, where the protein is complexed with the multiple guides.

In one aspect the invention provides escorted Cas9 CRISPR-Cas systems or complexes, especially such a system involving an escorted Cas9 CRISPR-Cas system guide. By "escorted" is meant that the Cas9 CRISPR-Cas system or complex or guide is delivered to a selected time or place within a cell, so that activity of the Cas9 CRISPR-Cas system or complex or guide is spatially or temporally controlled. For example, the activity and destination of the Cas9 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted Cas9 CRISPR-Cas systems or complexes have a gRNA with a functional structure designed to improve gRNA structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX™; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, provided herein is a gRNA modified, e.g., by one or more aptamer(s) designed to improve gRNA delivery, including delivery across the cellular membrane, to intracellular compartments, or into the nucleus. Such a structure can include, either in addition to the one or more aptamer(s) or without such one or more aptamer(s), moiety (ies) so as to render the guide deliverable, inducible or responsive to a selected effector. The invention accordingly comprehends an gRNA that responds to normal or pathological physiological conditions, including without limitation pH, hypoxia, 02 concentration, temperature, protein concentration, enzymatic concentration, lipid structure, light exposure, mechanical disruption (e.g. ultrasound waves), magnetic fields, electric fields, or electromagnetic radiation.

The escort aptamer may for example change conformation in response to an interaction with the aptamer ligand or effector in the cell.

The escort aptamer may have specific binding affinity for the aptamer ligand.

The aptamer ligand may be localized in a location or compartment of the cell, for example on or in a membrane of the cell. Binding of the escort aptamer to the aptamer ligand may accordingly direct the egRNA to a location of interest in the cell, such as the interior of the cell by way of binding to an aptamer ligand that is a cell surface ligand. In this way, a variety of spatially restricted locations within the cell may be targeted, such as the cell nucleus or mitochondria.

In some embodiments, the construct RNA capture domain is an RNA-binding protein domain. The RNA-binding protein domain recognizes corresponding distinct RNA sequences, which may be aptamers. For example, the MS2 RNA-binding protein recognizes and binds specifically to the MS2 aptamer (or vice versa). Similarly, an MS2 variant adaptor domain may also be used, such as the N55 mutant, especially the N55K mutant. This is the N55K mutant of the MS2 bacteriophage coat protein (shown to have higher binding affinity than wild type MS2 in Lim, F., M. Spingola, and D. S. Peabody. “Altering the RNA binding specificity of a translational repressor.” Journal of Biological Chemistry 269.12 (1994): 9006-9010).

The construct RNA sequence comprises a retrieval element and a cellular RNA capture element. In certain example embodiments, the cellular RNA capture element hybridizes to cellular RNA such that the bound cellular RNA is packaged inside the export compartment with the construct RNA.

The cellular RNA capture element of the construct RNA sequence binds target RNAs in the cell. The cellular RNA capture element may bind target RNAs in an unbiased manner. For example, the cellular RNA capture element may be a poly-U sequence. In certain example embodiments, the poly-U sequence is approximately 15 to approximately 50 nucleotides long. In certain other example embodiments, the cellular RNA capture element may comprise a (UUG) n motif, wherein “n” may range from approximately 1 to approximately 20. In certain example embodiments, the cellular RNA capture element may comprise a sequence that can hybridize to a specific target RNA species, such as specific mRNA transcript. In certain example embodiments, the cellular RNA capture element comprises SEQ ID NO: 12.

The construct RNA sequence may further include a barcode. A barcode is generated by sequentially attaching two or more detectable oligonucleotide tags to each other. As used herein, a “detectable oligonucleotide tag” is an oligonucleotide that can be detected by sequencing of its nucleotide sequence and/or by hybridization to detectable moieties such as optically labeled probes. The oligonucleotide tags that make up a barcode are typically randomly selected from a diverse set of oligonucleotide tags. For example, an oligonucleotide tag may be selected from a set A, B, C, and D, with each set comprising random sequences of a particular size. An oligonucleotide tag is first selected from set A, then a second oligonucleotide tag is selected from set B and concatenated to the oligonucleotide from set A. The process is repeated for sets C and D such that an oligonucleotide tag from C is concatenated to AB and an oligonucleotide tag from D is concatenated to ABC. The particular sequence selected from each set and the order in which the oligonucleotides are concatenated define a unique barcode. Methods for generating barcodes for use in the constructs disclosed herein are described, for example, in International Patent Application Publication No. WO/2014/047561. In certain example embodiments, the barcodes are approximately 10 to approximately 40 nucleotides long. In certain example embodiments, the barcodes comprise 2, 3, 4, 5, 6, 7, 8, 9, or 10 distinct ordered positions. In certain example embodiments, the barcode of each construct is unique to that construct or sub-set of constructs such that delivery of that construct or sub-set of constructs is unique to that cell or population of cells. For example, a first cell or population of cells may be transduced with a first construct or set of constructs comprising a first barcode, and a second cell or second population of cells may be transduced with a second construct of set of constructs comprising a second barcode, such that sequencing libraries derived from exported cellular RNA from a particular cell or cell population will include the same unique barcode, thereby identifying those cellular RNAs as originating from the same cell or same cell population.

Nucleic acid barcodes can include a short sequence of nucleotides that can be used as an identifier for an associated molecule, location, or condition. In certain embodiments, the nucleic acid identifier further includes one or more unique molecular identifiers and/or barcode receiving adapters. A nucleic acid identifier can have a length of about, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 base pairs (bp) or nucleotides (nt). In certain embodiments, a nucleic acid identifier can be constructed in combinatorial fashion by combining randomly selected indices (for example, about 1, 2, 3, 4, 5, 6, 7, 8, 9, or 10 indexes). Each such index is a short sequence of nucleotides (for example, DNA, RNA, or a combination thereof) having a distinct sequence. An index can have a length of about, for example, 4, 5, 6, 7, 8, 9, 10, 11, 12, 13, 14, 15, 16, 17, 18, 19, 20, 21, 22, 23, 24, or 25 by or nt. Nucleic acid identifiers can be generated, for example, by split-pool synthesis methods, such as those described, for example, in International Patent Publication Nos. WO 2014/047556 and WO 2014/143158, each of which is incorporated by reference herein in its entirety.

One or more nucleic acid identifiers (for example a nucleic acid barcode) can be attached, or “tagged,” to a target molecule. This attachment can be direct (for example, covalent or noncovalent binding of the nucleic acid identifier to the target molecule) or indirect (for example, via an additional molecule). Such indirect attachments may, for example, include a barcode bound to a specific-binding agent, for example, the cellular RNA capture element, that recognizes a target molecule. In certain embodiments, a barcode is attached to protein G and the target molecule is an antibody or antibody fragment. Attachment of a barcode to target molecules (for example, proteins and other biomolecules) can be performed using standard methods well known in the art. For example, barcodes can be linked via cysteine residues (for example, C-terminal cysteine residues). In other examples, barcodes can be chemically introduced into polypeptides (for example, antibodies) via a variety of functional groups on the polypeptide using appropriate group-specific reagents. In certain embodiments, barcode tagging can occur via a barcode receiving adapter associate with (for example, attached to) a target molecule, as described herein. Compositions and methods for concatemerization of multiple barcodes are described, for example, in International Patent Publication No. WO 2014/047561, which is incorporated herein by reference in its entirety.

In some embodiments, a nucleic acid identifier (for example, a nucleic acid barcode) may be attached to sequences that allow for amplification and sequencing (for example, SBS3 and P5 elements for ILLUMINA® sequencing). In certain embodiments, a nucleic acid barcode can further include a hybridization site for a primer (for example, a single-stranded DNA primer) attached to the end of the barcode. For example, an origin-specific barcode may be a nucleic acid including a barcode and a hybridization site for a specific primer.

In certain example embodiments, the nucleic acid constructs only comprise a construct RNA sequence and may be used independently to barcode cellular components with origin-specific barcodes without use of the fusion proteins and self-reporting export as discussed above. These nucleic acid constructs encode a barcode and a cellular RNA capture element as described above. In certain example embodiments, the construct RNA sequence may further comprise a filter sequence (SEQ ID NO: 13). The filter sequence is a defined and searchable nucleic acid sequence set at a fixed distance from all barcodes or other unique molecular identifiers, thus enabling detection of barcodes and unique molecular identifiers in downstream sequencing data as further described below. The construct RNA sequence may also further comprise an adapter sequence. The adapter sequence defines a nucleic acid sequence that is complementary and enables binding of downstream amplification and/or sequencing primers as described further below.

General Construct Elements

Figure 26A:
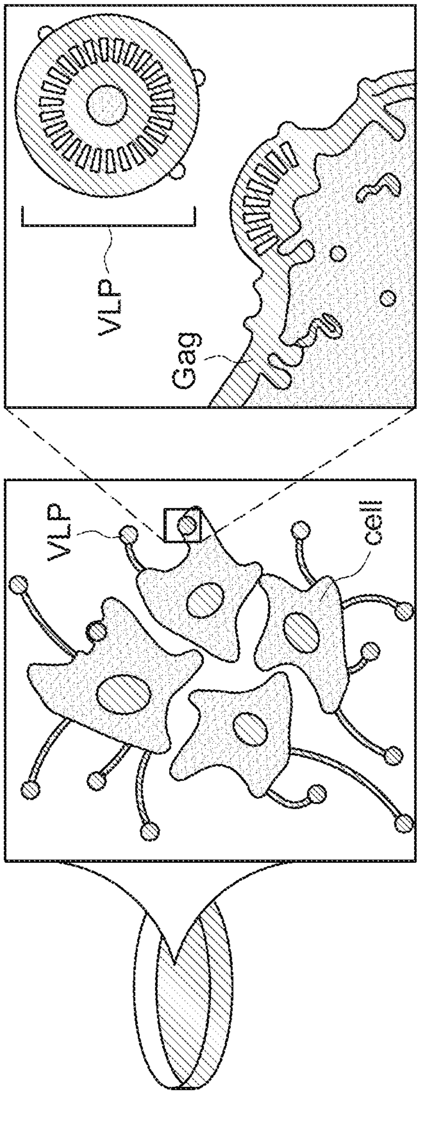
FIG. 26A-26O—(FIG. 26A) Cellular self-reporting leverages virus like particle (VLP) export of RNA. Gag accumulates to assemble VLPs.
Figure 26B:
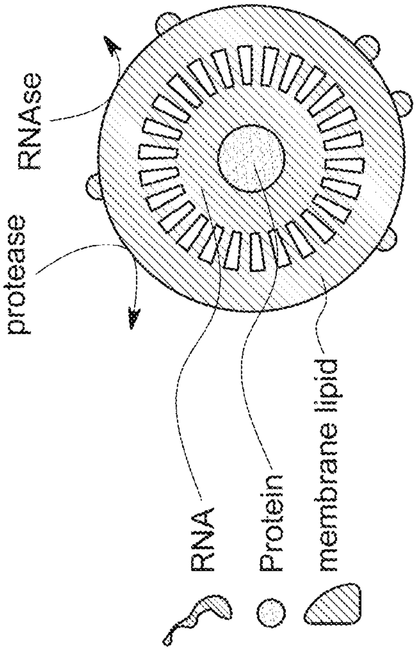
(FIG. 26B) VLPs can package several different types of cargos, including RNA, protein, and metabolites.
Figure 26C:
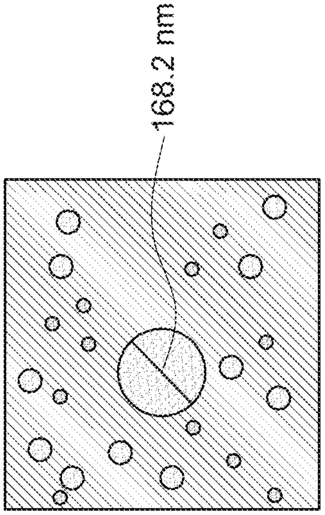
(FIG. 26C) Negative stain electron micrograph showing a VLP.
Figure 26D:
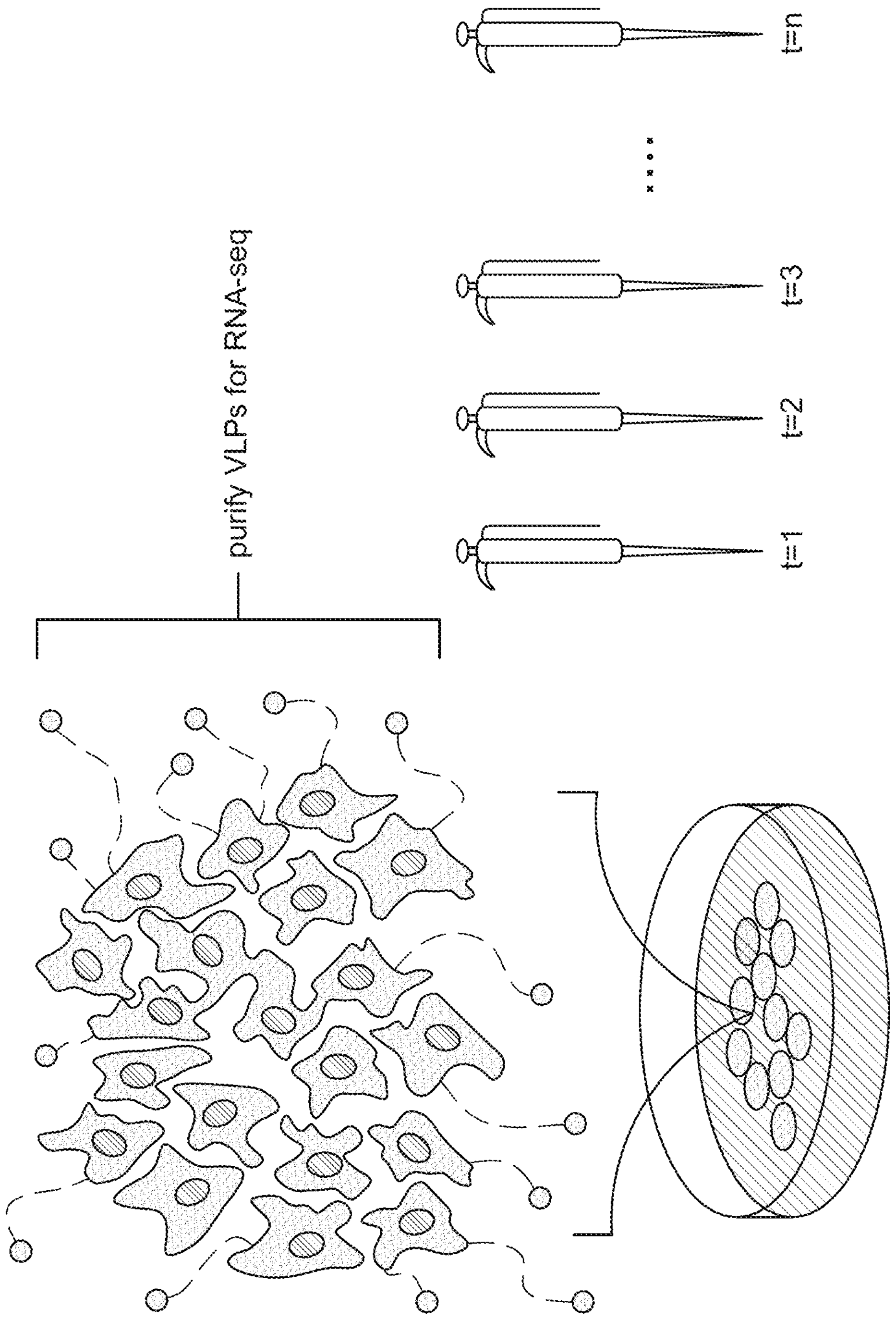
(FIG. 26D) Example of time-point collection using cellular self-reporting.
Figure 26E:
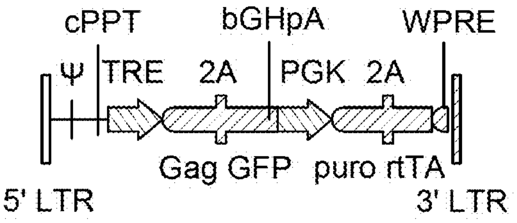
(FIG. 26E) Schematic of LentiGag construct that enables stable doxycycline-inducible RNA export.

In certain example embodiments, all of the constructs disclosed herein may further include an inducible promoter to control expression of the construct elements. Inducible promoters may include any suitable inducible promoter system. As recognized by one of ordinary skill in the art, the suitability of a particular inducible promoter system is dictated by the cellular system in which the constructs will be used. Accordingly, the biotic or abiotic factors that induce the activity of such promoters must be compatible with the cellular system in which the constructs of the present invention will be used. For example, a biotic or abiotic factor that negatively impacts cell viability or significantly alters gene expression of the cell in the context of the biological condition being studied would not be a suitable inducible promoter system. The inducible promoter may be a suitable chemically-regulated promoter or suitable physically-regulated promoter. The chemically-regulated promoter may be a suitable alcohol-regulated promoter, tetracycline-regulated promoter, antibiotic-regulated promoter, steroid-regulated promoter, or a metal-regulated promoter. The physically-regulated promoters may be a temperature-regulated promoter or a light-regulated promoter. In certain example embodiments, the inducible promoter is a. tetracycline-regulated promoter such as pTet-On, pTet-Off, or pTRE-Tight. In certain example embodiments the promoter is a dox-inducible promoter. In certain other example embodiments, the promoter is a cell-specific or tissue-specific promoter. In certain example embodiments, the construct may comprise both a cell-specific or tissue specific promoter and a second promoter such as dox. See FIG. 5. A construct can comprise one or more elements as depicted in FIG. 26E.

Linker

In certain example embodiments, all of the constructs disclosed herein may further comprise a steric linker sequence. The encoded steric linker sequence may be a random peptide sequence of a particular size. The size of the steric linker sequence may control the rate of export, the size of the export compartment or both. For example, a larger linker sequence appended to an export compartment protein may slow the rate at which the export compartment proteins can self-assemble by creating steric hindrance that slows the rate of assembly. Likewise, a larger linker sequence that must be incorporated into the export compartment may increase the size of the export compartment formed. In certain example embodiments, the steric linker is approximately 2 to approximately 12 amino acids in size. In certain example embodiments, the linker sequence is located on the N-terminus of the secretion-inducing protein. In certain other example embodiments, the linker sequence is located on the C-terminus of the secretion-inducing protein.

Affinity Tag

Figure 6:
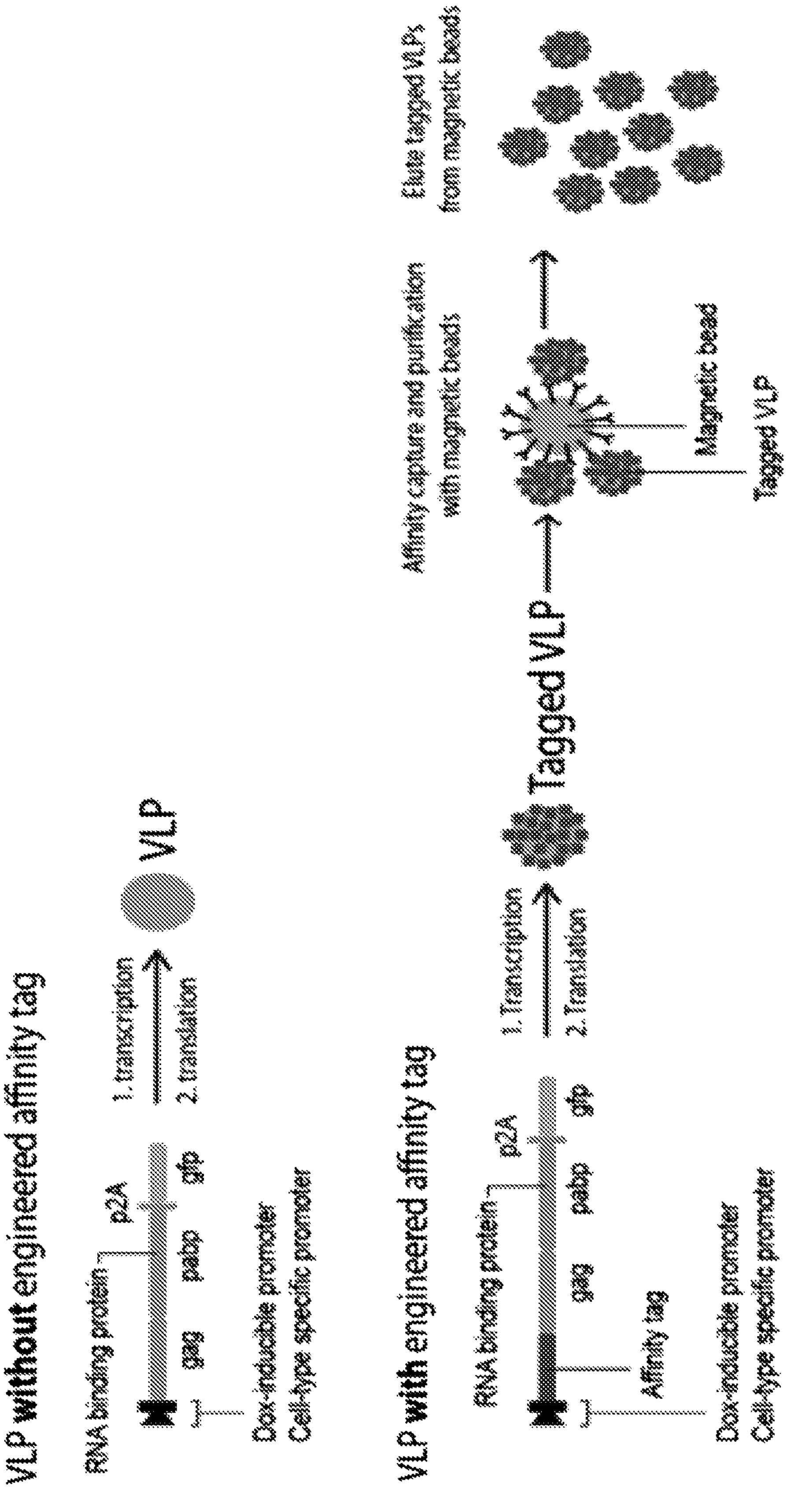
FIG. 6—is a schematic of an example construct further encoding an affinity tag for subsequent isolation and enrichment of expressed VLPs in accordance with certain example embodiments.
Figure 7:
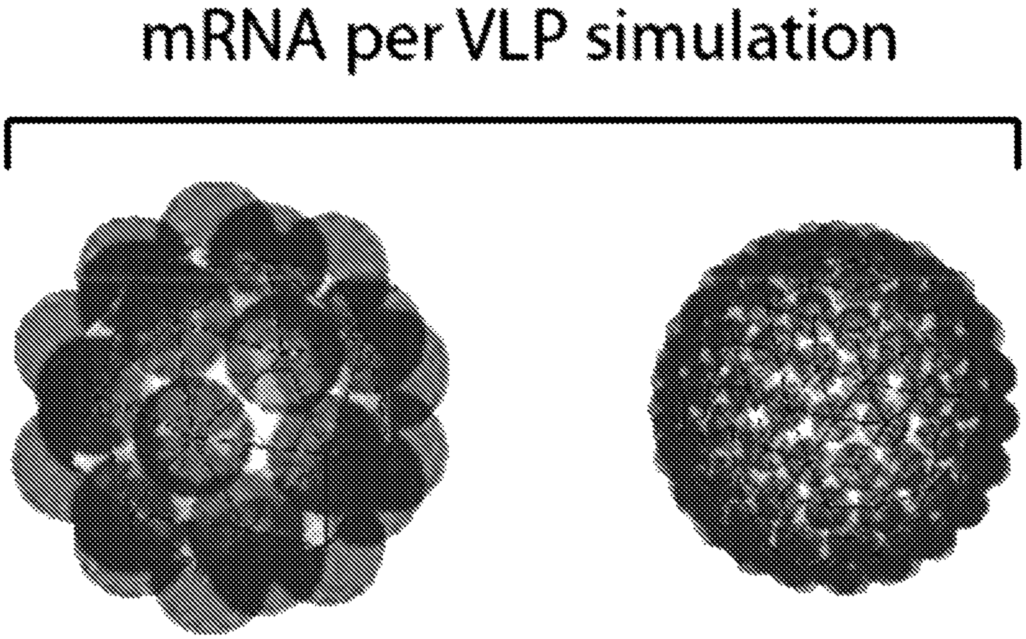
FIG. 7—is a diagram summarizing simulation of export compartment size and the theoretical number of mRNA that could be packaged inside an example export compartment.
Figure 8:
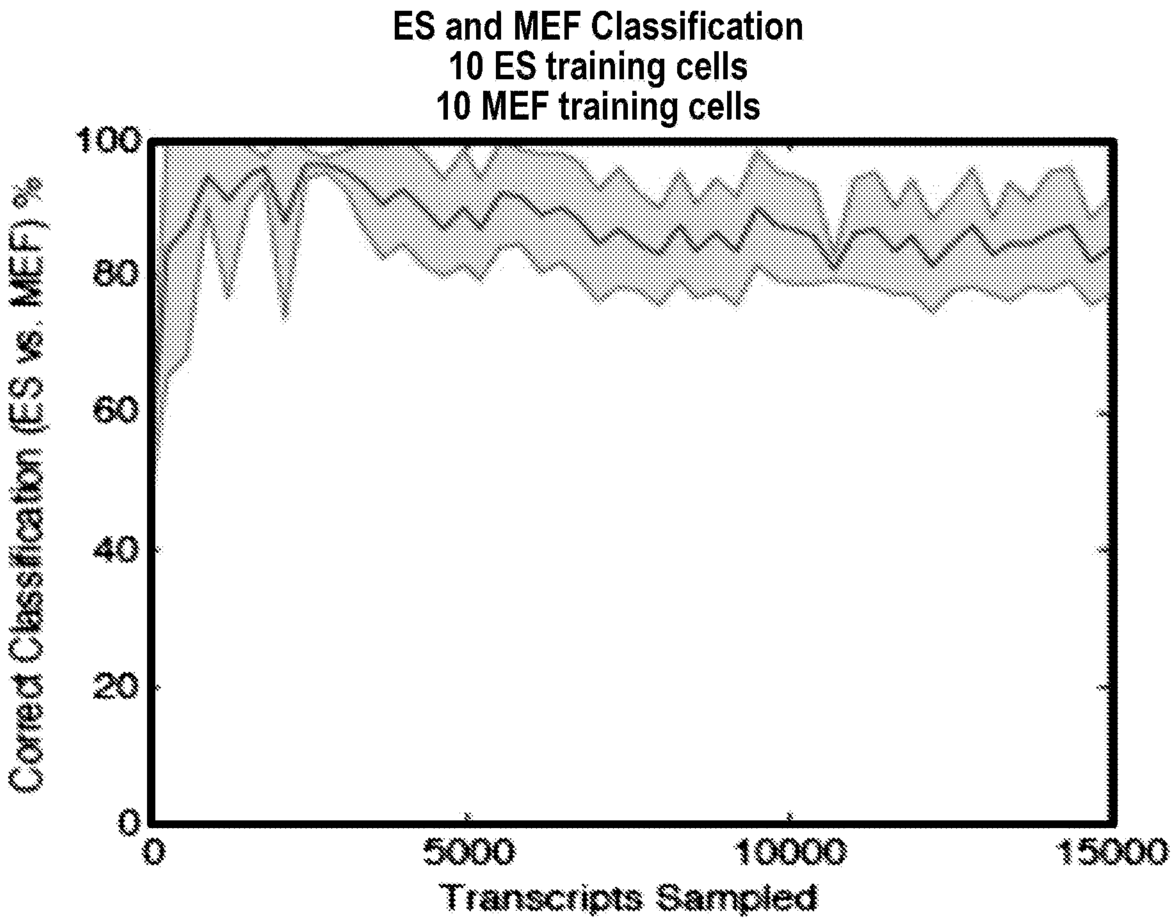
FIG. 8—is a graph showing a simulation based on exclusive reads per cell type that allows for >80% accuracy of prediction with a simple algorithm that uses inner-products and training on 10 cells per cell type.
Figure 9:
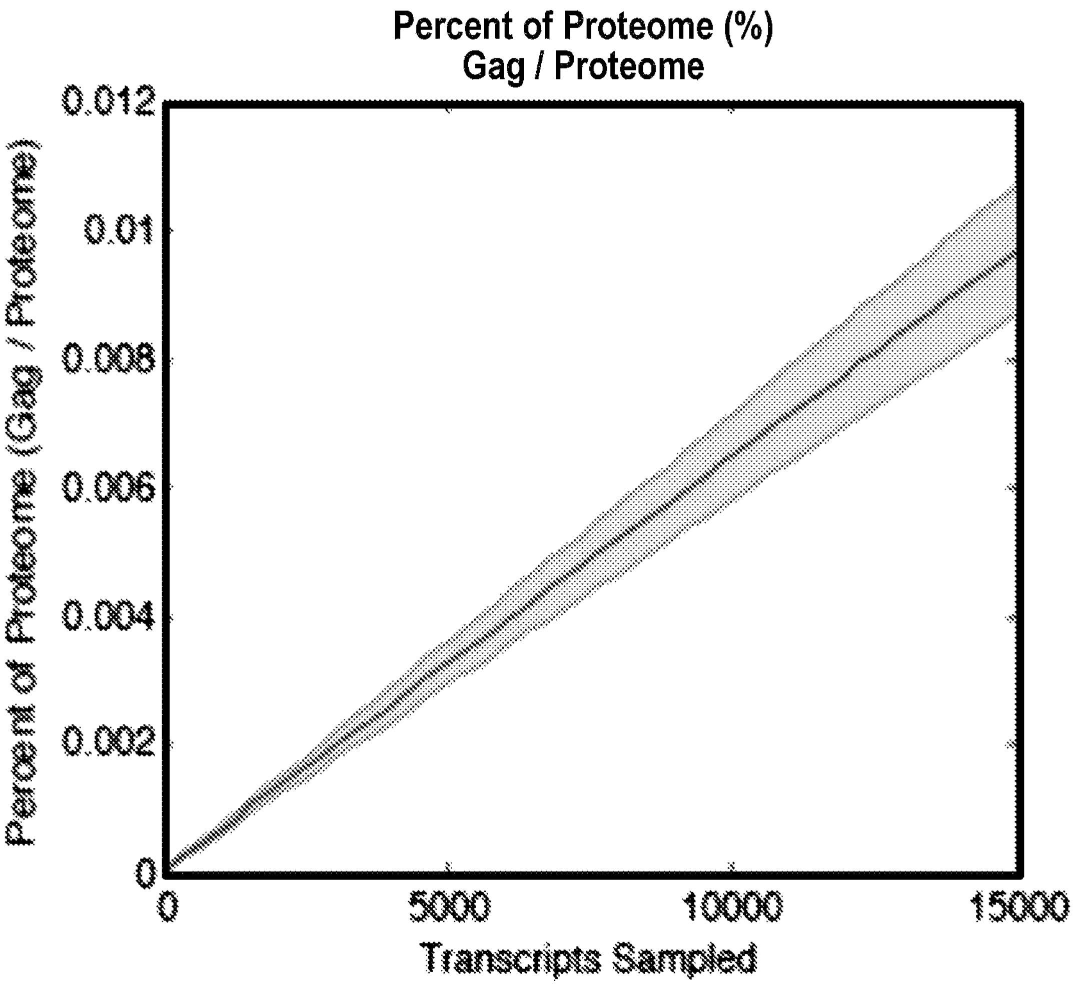
FIG. 9—is a graph showing the percent of the proteome that is composed of Gag proteins per number of transcripts sampled.

In certain example embodiments, the constructs disclosed herein may further encode an affinity tag. An affinity tag may include, but is not limited to, Flag, CBP, GST, HA, HBH, MBP, Myc, polyHis, S-tag, SUMO, TAP, TRX, and V5. Affinity tags may also include engineered transmembrane domains in order to increase the likelihood of surface presentation. The affinity tags may be then used to purify, for example VLPs, formed by the fusion protein using standard affinity purification techniques. See FIG. 6. The affinity tag may be encoded by the construct such that the affinity tag is located on a N-terminus of the secretion-inducing protein.

Figure 3:
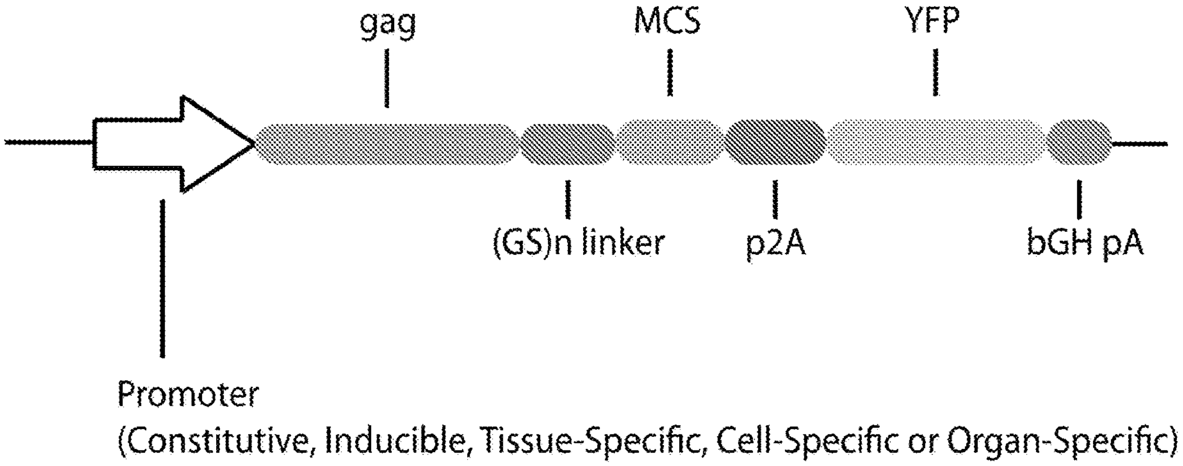
FIG. 3—is a diagram of a construct in accordance with certain example embodiments. The diagram shows a possible DNA construct for making Gag fusion proteins. The glycine-serine (GS) linker (SEQ ID NO: 7) functions as a flexible amino acid linker between the gag protein and the cloned protein of interest. The RNA capture domain of interest is ligated into the construct in the multiple cloning site (MCS) via standard restriction cloning techniques. The p2A linker (SEQ ID NO: 5) serves as a self-cleaving linker, allowing yellow fluorescent protein (YFP) (SEQ ID NO: 6) to be translated from the same transcript without fusion The DNA construct includes a bGH pA terminator (SEQ ID NO: 8). The construct may include a spacer between elements (SEQ ID NO: 9)

In certain example embodiments, the constructs may further encode an antibiotic resistance gene to facilitate chemical selection of cells or cell populations to which the RNA constructs described herein have been delivered and expressed. In certain example embodiments, the constructs disclosed herein may further encode a detectable self-reporting molecule. In certain example embodiments, the construct may further encode a cleavable linker between the detectable self-reporting molecule and the fusion protein of interest. See FIG. 3. In certain example embodiments, the cleavable linker may be a self-cleaving linker such as P2A. In certain example embodiments, the detectable self-reporting molecule is a fluorescently detectable self-reporting molecule such as RFP, YFP, or GFP. Detection of the self-reporting molecule in a cell or cell population may be used to determine successful delivery and expression of the constructs disclosed herein.

In certain example embodiments, the construct RNA sequences may further encode a nuclear export protein the enables nuclear export of Pol III driven transcript without perturbing cellular localization of other endogenous RNA transcripts. In certain other example embodiments, the barcode sequence may be incorporated into the 5' or 3' UTR of a Pol II driven transcript (e.g. GFP), which is naturally exported to the cytoplasm.

Vectors

In another aspect, the embodiments disclosed herein are directed to vectors for delivering the constructs disclosed herein to cells. In certain example embodiments the vector is a viral vector. Delivery methods can be as disclosed in Kaestner, et al.,BMCL, 25:6, 15 Mar. 2015, 1171-1176, doi: 10.1016/j.bmcl.2015.01.018 Suitable viral vectors include, but are not limited to, retroviruses, lentiviruses, adenoviruses and AAV. In certain other example embodiments, the vector is a non-viral vector. Suitable non-viral vectors include, but are not limited to, cyclodextrin, liposomes, nanoparticles, calcium chloride, dendrimers, and polymers including but not limited to DEAE-dextran and polyethylenimine. Further non-viral delivery methods include electroporation, cell squeezing, sonoporation, optical transfection (Ma et al, J. of Biomedical Optics, 16 (2), 028002 (2011), doi: 10.1117/1.3541781, protoplast fusion, impalefection (See, Mann et al., ACS Nano 2008, 2, 1, 69-76; doi: 10.1021/nn700198y), hydrodynamic delivery (See, Huang et al., Front Pharmacol. 2017; 8:591, doi: 10.3389/fphar.2017.00591) and magnetofection (See, e.g. Smolders, et al., J Neurosci Methods. 2018 Jan. 1; 293:169-173. doi: 10.1016/j.jneumeth.2017.09.017). For non-viral vectors, delivery to a microbe may be facilitated by standard transfection technologies such as electric pulsing, electroporation, osmotic shock, and polymeric-based delivery systems.

Non-limiting examples of such delivery means are e.g. particle(s) delivering component(s) of the complex, vector(s) comprising the polynucleotide(s) and nucleic acid constructs discussed herein. In some embodiments, the vector may be a plasmid or a viral vector such as AAV, or lentivirus.

In some embodiments, a host cell is transiently or non-transiently transfected with one or more vectors comprising the polynucleotides encoding one or more components of the nucleic acid constructs, system or complex for use in multiple targeting as defined herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art and exemplified herein elsewhere. Cell lines are available from a variety of sources known to those with skill in the art (see, e.g., the American Type Culture Collection (ATCC) (Manassas, Va.)). In some embodiments, a cell transfected with one or more vectors comprising the components of the system or complex for use in multiple targeting as defined herein is used to establish a new cell line comprising one or more vector-derived sequences. In some embodiments, a cell transiently transfected with the components of a system or complex for use is used to establish a new cell line comprising cells containing the modification but lacking any other exogenous sequence. In some embodiments, cells transiently or non-transiently transfected with one or more vectors comprising the systems described herein are used in assessing one or more test compounds.

Methods of Live Cell Sampling

The constructs and vectors disclosed herein can be used in methods for continuous live cell sampling enabling the ability to monitor molecular profile changes over time. In certain example embodiments, the exported cellular contents may be barcoded with a cell-specific barcode allowing multiple samples to be processed in bulk while retaining the ability to identify the cell or cell population of origin.

In one example embodiment, a method of single cell gene expression profiling comprises delivering a nucleic acid construct encoding a fusion protein and a construct RNA sequence to a cell or population of cells. For embodiments utilizing viral vectors, the cell or cells are transduced with the constructs at a low multiplicity of infection. In certain example embodiments, the cells may be subsequently subjected to chemical selection to ensure that all cells have a stable single-copy of the constructs. For example, the constructs may encode an antibiotic resistance gene and chemical selection is carried out by exposure of the cell or cells to a corresponding antibiotic. Alternatively, for those embodiments employing a detectable self-reporting molecule, such as GFP, the self-reporting molecule may be used to assess successful transfection. Cells expressing the self-reporting molecule may then be selected using known methods in the art, such as flow cytometry.

The fusion protein comprises a secretion-inducing domain and a construct RNA capture domain. The construct RNA sequence comprises a retrieval element and a cellular RNA capture element. The construct RNA sequence may further comprise a barcode. The barcode comprises a nucleic acid sequence unique to the nucleic acid construct delivered to the cell. The cellular RNA capture element binds cellular RNA by hybridizing to the cellular RNA. In certain example embodiments the construct RNA sequence hybridizes to mRNA via a poly-U sequence or sequence comprising a repeating (UUG) n motif. In certain example embodiments, the secretion-inducing domain is an export compartment protein described herein that self-assembles to form an export compartment. In the process of self-assembling to form the export compartment the construct RNA capture domain binds the retrieval element on the construct RNA sequence resulting in the packaging of both the construct RNA sequence and any cellular RNA hybridized to the construct RNA sequence via the construct RNA sequence's cellular retrieval element. The export compartment is then exported from the cell. For example, the export compartment may be released into the cell culture media. The media may then be collected and the sample isolated. For example, the export compartments may be isolated from the cell culture media by ultracentrifugation, or other methods that separate components based on size or density. In certain example embodiments, the fusion protein further comprises an affinity tag as described above, which may be used to isolate and enrich for the export compartments using standard affinity purification techniques known in the art.

Figures 2A, 2B, 2C, 2D, 2E:
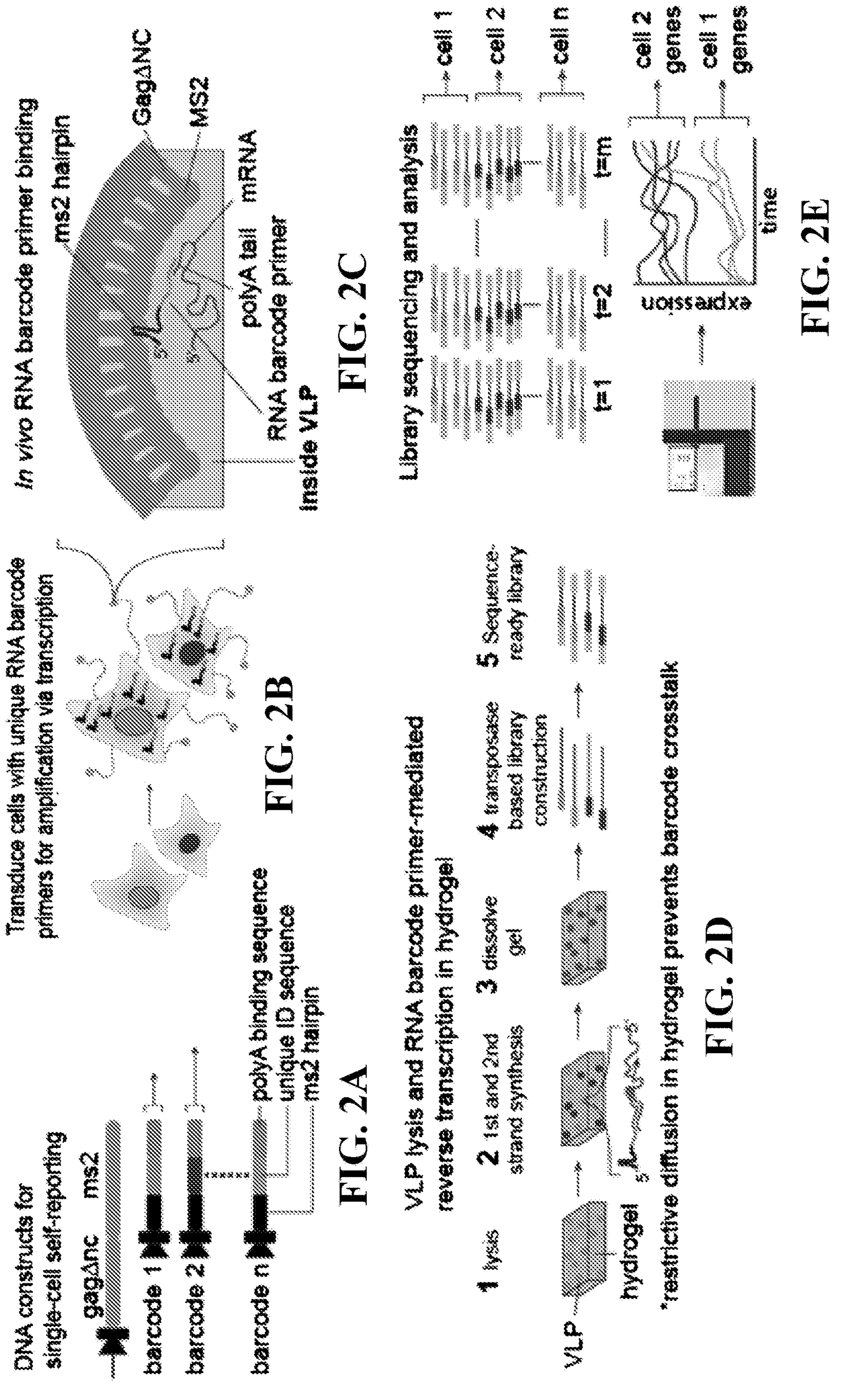
FIG. 2—is a diagram depicting a barcoded self-reporting strategy in accordance with certain example embodiments.

The isolated export compartments may then be lysed and the exported cellular RNAs retrieved. In certain example embodiments, the isolated VLPs are placed into a hydrogel. The VLPs are then lysed and first and second strand synthesis as described above is conducted within the hydrogel. The hydrogel is then dissolved and sequencing library preparation conducted as described above. The restrictive diffusion provided by the hydrogel may be used to prevent potential barcode cross-talk during the RT reaction steps. See FIG. 2.

After RNA collection, RNA sequences may be permanently linked to the cellular barcodes by utilizing the barcoded construct RNA sequence as a primer for reverse transcription thereby incorporating the barcode in the resulting RNA-DNA duplex. Likewise, in certain example embodiments, the poly-A tail of cellular mRNA may be used to reverse transcribe the barcode portion of the construct RNA sequence. In certain example embodiments a primer designed to bind to the barcode sequence, or a portion thereof, may be used to initiate reverse transcription. See FIG. 1. Various example embodiments for incorporation of the barcode sequence into DNA amplicons suitable for sequencing analysis are discussed below.

Figure 11:
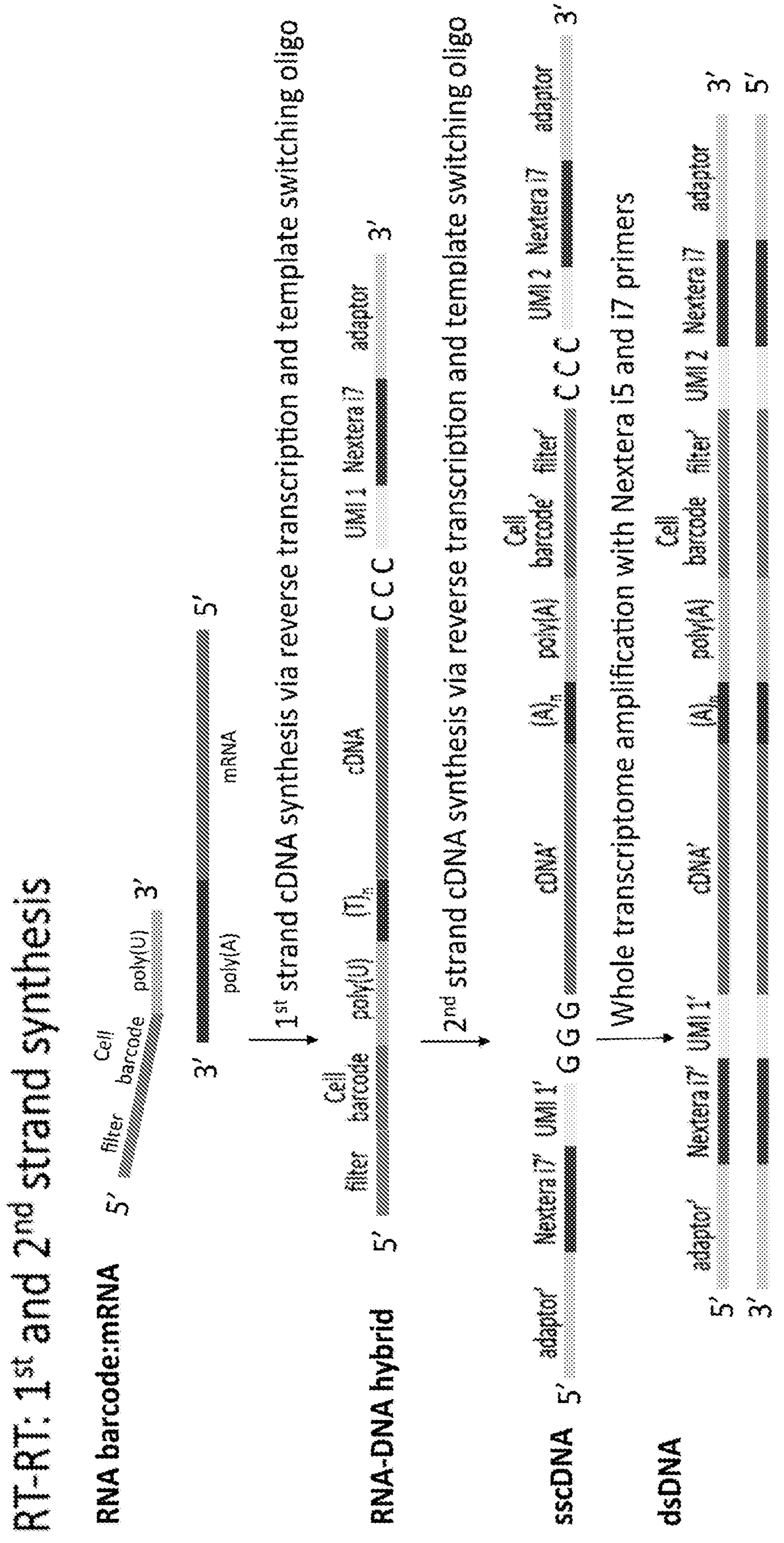
FIG. 11—is a schematic showing one example embodiment for incorporation of barcodes of dsDNA amplicons derived from cellular mRNA isolated from export compartments.

Discussion of the following example embodiment is made with reference to FIG. 11. The RNA construct sequence comprises at least, in a 5' to 3' direction, a retrieval element, a filter, a barcode, and a poly(U) or (UUG), motif for binding to poly-A tails cellular mRNAs. the RNA construct sequence is used to prime first strand cDNA synthesis via reverse transcription of the mRNA template. Template switching may be used to incorporate sequences from a template switching oligonucleotide. For example, a MLV reverse transcriptase- or similar reverse transcriptase—may be used to add non-template nucleotides to the first-strand cDNA when it reaches the 5' end of the mRNA. Template switching oligonucleotides designed to bind to these non-template nucleotides may then be used to facilitate template switching and incorporation of sequences complementary to the template switching oligonucleotide. In certain example embodiments, the template switching oligonucleotide may be used to introduce, in a 5' to 3' direction, a unique molecular identifier (UMI), a first sequencing primer binding site, and an adapter sequence. A UMI is a short nucleotide sequence (e.g. six to eight bp) that uniquely identifies each template switching oligonucleotide. Next a second cDNA strand is synthesized via reverse transcription and use of a second template switching oligonucleotide resulting in the single stranded cDNA (sscDNA). Double-stranded DNA amplicons suitable for sequencing analysis are then generated by amplification of the sscDNA using the sequencing primer binding sequences introduced into the sscDNA.

Figure 12:
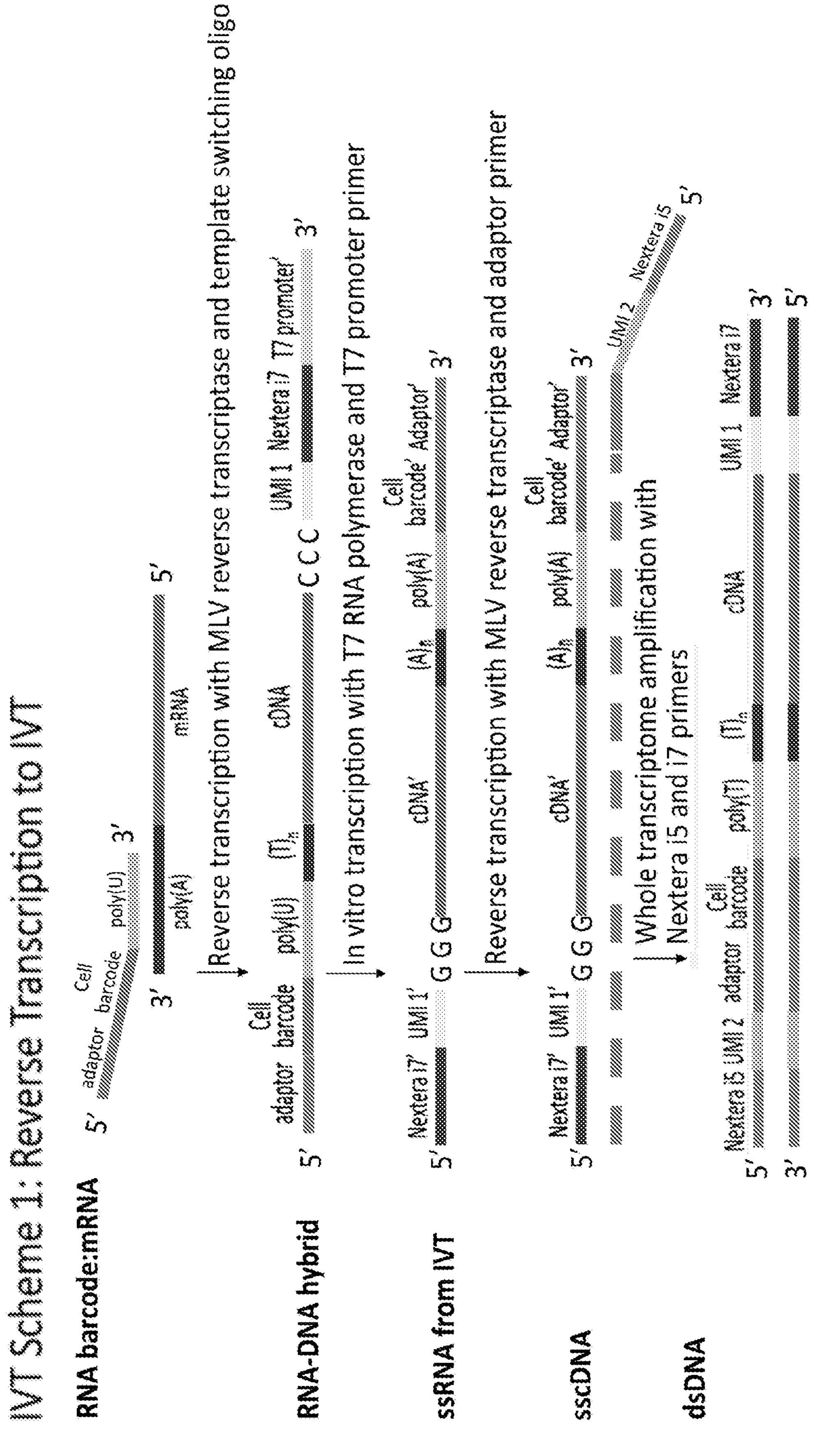
FIG. 12—is a schematic showing one example embodiment for incorporation of barcodes into dsDNA amplicons derived from cellular mRNA isolated from export compartments.

Discussion of the following example embodiment is made with reference to FIG. 12. The construct RNA sequence may comprise, in a 5' to 3' direction, an adapter sequence a barcode and a poly(U) or (UUG), motif. Lysis of export compartments may be completed in hydrogels as described above in [0152]. As in the previous embodiment, the construct RNA sequence is used to first prime a reverse transcription reaction that results in addition of a UNII sequence, sequencing primer binding sequence and the complement of a RNA polymerase promoter (such as a complement of a T7 promoter) and the RNA-DNA hybrid show in FIG. 12. A single stranded RNA copy is then generated from the RNA-DNA hybrid by in vitro transcription with a RNA polymerase and RNA polymerase promoter. A single stranded cNDA (sscDNA) is then generated by reverse transcription primed by an adapter primer that binds its complementary sequence incorporated into the ssRNA. The adapter primer may further comprise a second UNII and a second sequencing primer binding sequence. Double-stranded DNA amplicons suitable for sequencing analysis are then generated by amplification of the dscDNA product using a first and second sequencing primer complementary to the first and second sequencing primer binding sequences.

Figure 13:
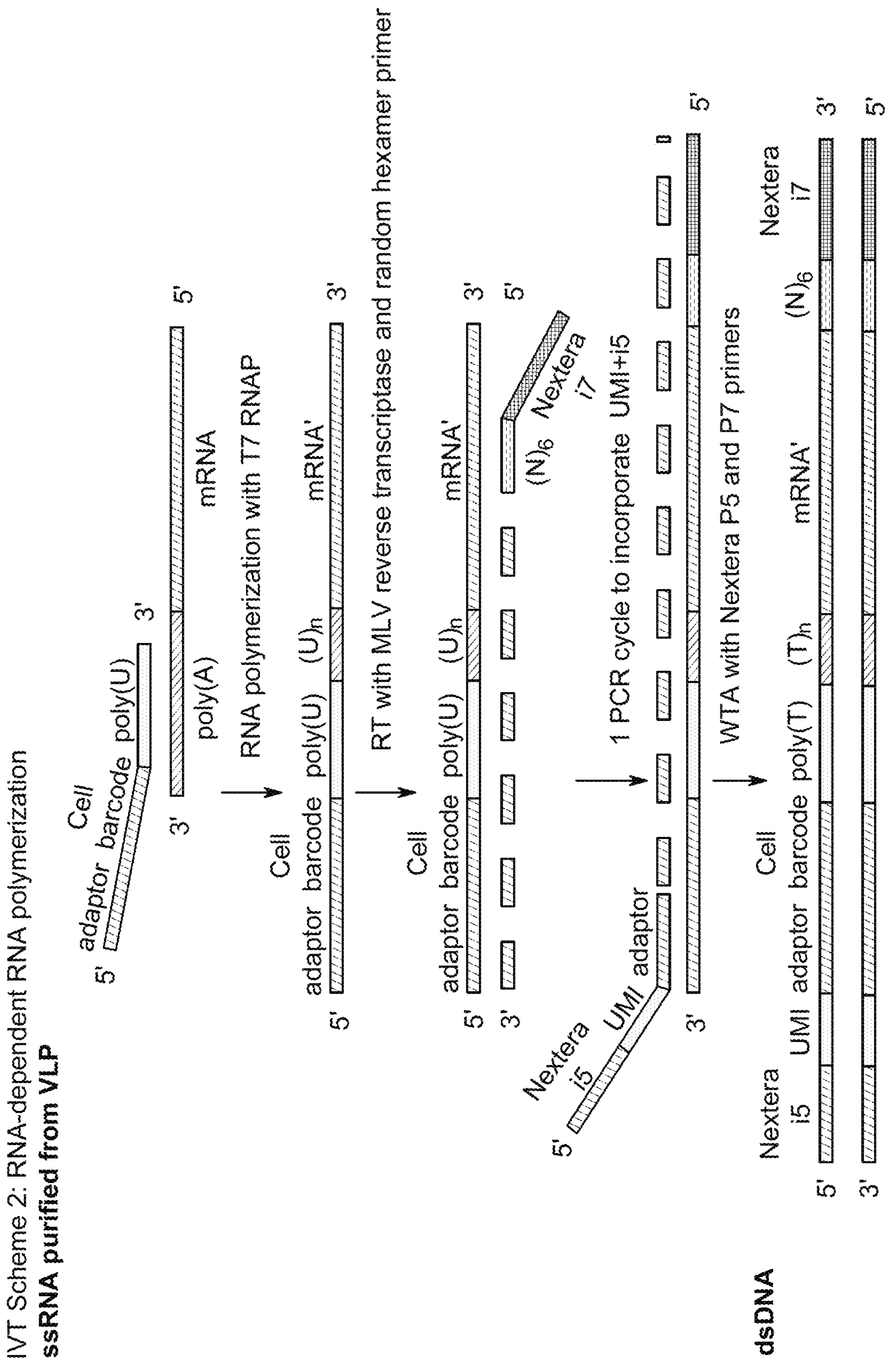
FIG. 13—is a schematic showing one example embodiment for incorporation of barcodes into dsDNA amplicons derived from cellular mRNA isolated from export compartments.

Discussion of the following example embodiment is made with reference to FIG. 13. The same construct RNA sequence architecture described in may be used to prime RNA polymerization using T7 RNAP, or similar RNA polymerase, to generate a RNA complement of the cellular mRNA. A reverse transcription reaction is then conducted using a reverse transcription primer, the reverse transcription primer comprising, in a 5' to 3' direction, a sequencing primer binding sequence and a random hexamer motif. The resulting RNA comprises the original mRNA sequence with the random hexamer and first sequencing primer binding site sequence appended to the 5' end and the cell barcode and adapter sequence appended to the 3' end. A single PCR cycle using as second primer is conducted to generate a DNA: RNA hybrid, the second primer comprising, in a 5' to 3' direction, a second sequencing primer binding site, a UNIL and complementary adapter binding sequence. This reaction incorporates the second sequencing primer binding site and UNII into the DNA: RNA hybrid. The DNA: RNA hybrid is then amplified through whole transcriptome amplification using the first and second sequencing primers. The resulting dsDNA amplicons may then be prepped for sequencing using standard methods known in the art.

Figure 14:
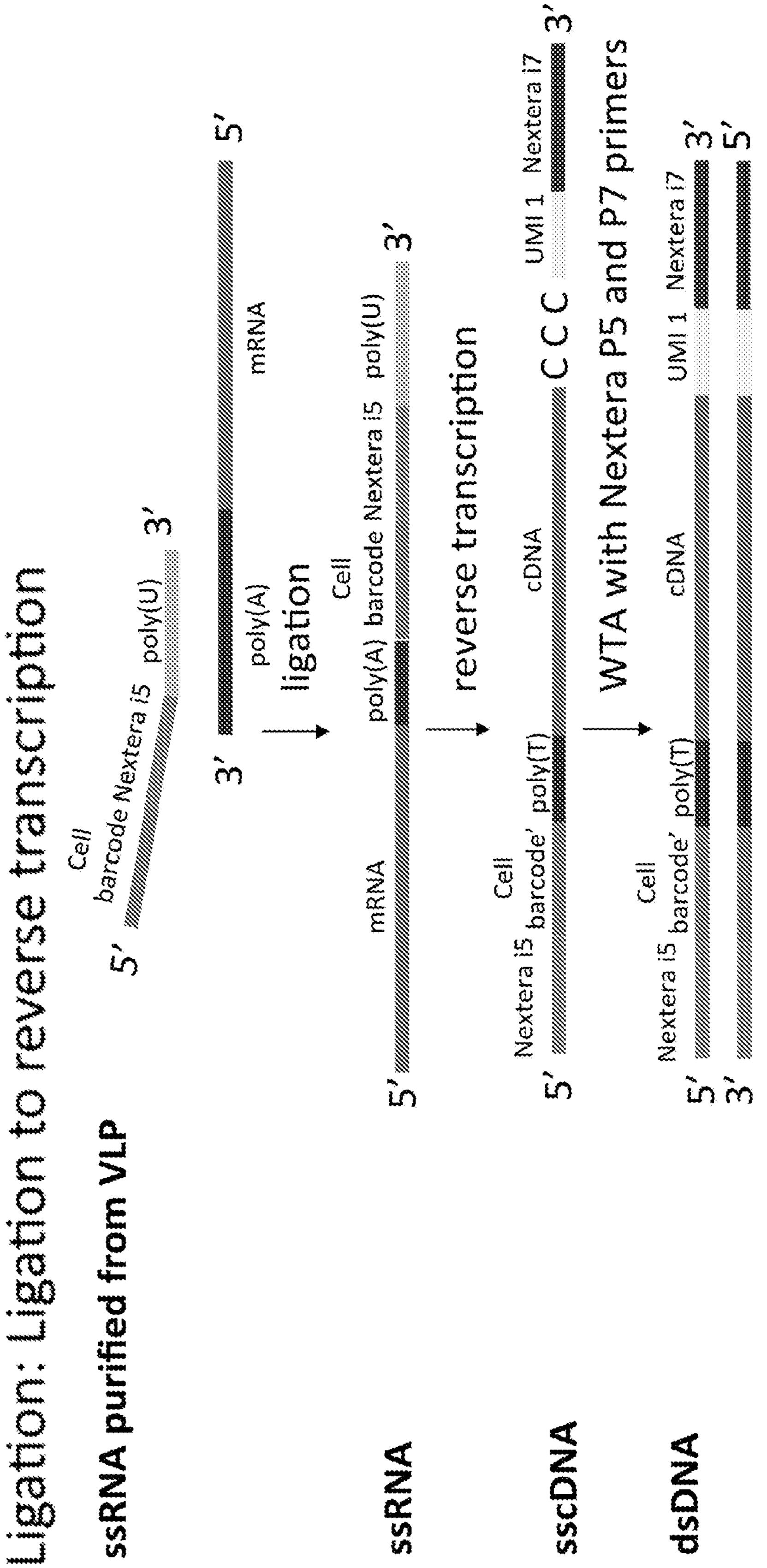
FIG. 14—is a schematic showing one example embodiment for incorporation of barcodes into dsDNA amplicons derived from cellular mRNA isolated from export compartments.
Figure 15A:
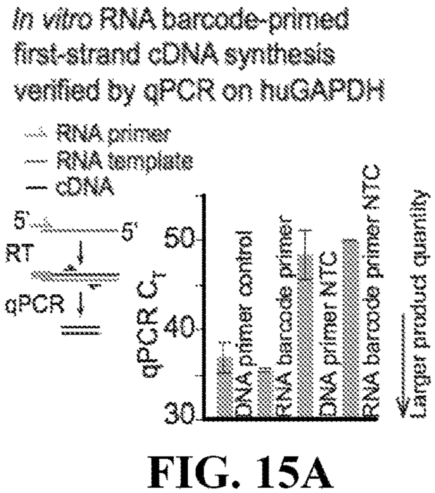
FIG. 15—A) Reverse transcription with RNA primers. B) Reverse transcription in crosstalk-preventing hydrogels with RNA primers. C) Genomic integration of synthetic RNA barcodes in HEK cells by lentiviral transduction. D) Efficient in vitro library construction of RNA barcoded monoclonal RNA template (SEQ ID NO: 13). The filter may include a SMART-SEQ2™ handle (SEQ ID NO: 11).
Figure 15B:
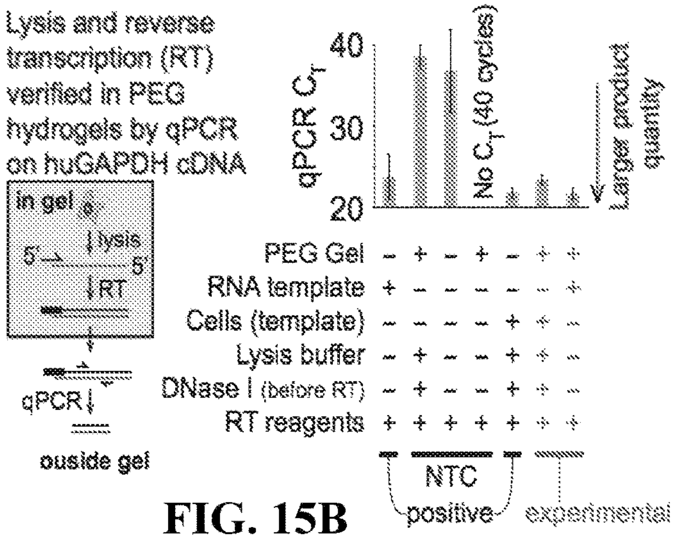
Figure 15C:
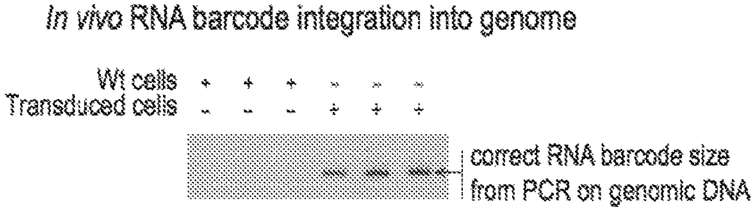
Figure 15D:
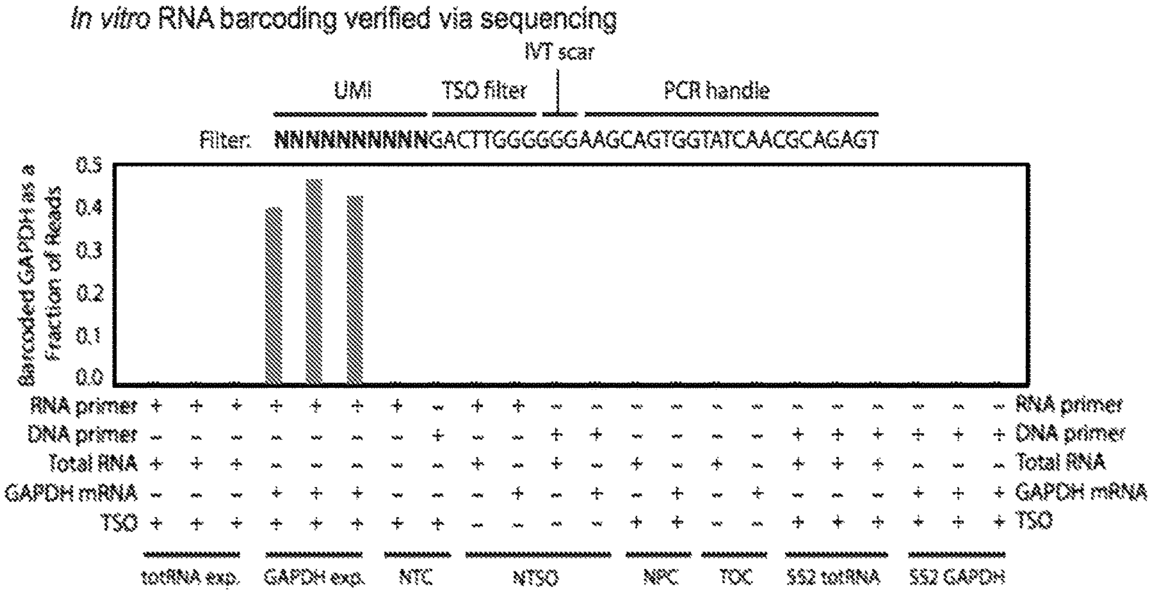

Discussion of the following alternative example embodiments is made with reference to FIG. 14. The construct RNA sequence may comprise, in a 5' to 3' direction, a barcode a first sequencing primer binding site, a poly(U) or (UUG), motif. The construct RNA sequence hybridizes to the poly-A tail of the mRNA via the poly(U) or (UUG), motif. The 5' end of the RNA construct sequence is then ligated to the 3' poly-A tail of the mRNA. In certain example embodiments, the mRNA-construct RNA duplex may be further stabilized prior to ligation by cross-liking the poly-A and poly(U) sequences, for example using a psoralen. After ligation cross-linking is reversed. The ligated single stranded mRNA product then comprises, in a 5' to 3' direction, the cellular mRNA sequence, barcode, first sequencing primer binding site, and poly(U). The mRNA is reverse transcribed into cDNA as previously described resulting in barcoded cDNA. A second reverse transcription reaction is then primers using a primer comprising a complementary sequence to the non-template nucleotides added by the first RT reaction, a UMI, and a second sequencing primer binding site. The resulting dsDNA product is then amplified by whole transcriptome amplification using first and second sequencing primers that hybridize to the first and second sequencing primer binding sites. The resulting dsDNA amplicons may then be prepped for sequencing using standard methods known in the art.

Transcripts with the same unique barcode may then be identified as originating from the same cell or cell population. Isolated export compartments may be collected over multiple time points from the same cells or population of cells. As noted above, the constructs may further include an inducible promoter to control at what time points the expression of the export compartment is turned on and off.

In addition, to using sequenced barcode information to identify the origin of particular transcripts, optical detection of the barcodes may also be used to match single-cell gene expression profiles with microscopy. Combination with microscopy allows the tissue context of the assayed cells to be derived as well as key measures of cell morphology and protein levels. For example, optical detection of the barcodes would allow relationships between transcriptional changes involving many genes and optically observable phenomena to be tracked in coordinated time-lapse measurements at the single-cell level. A set of probes may be derived with each probe cable of specifically hybridizing to a given oligonucleotide tag in the barcode. Each probe for a given oligonucleotide sequence may be labeled with a different optically detectable label. In one example embodiment, the optically detectable label is a fluorophore. In another example embodiment, the optically detectable label is a quantum dot. In another example embodiments, the optically detectable label is an object of a particular size, shape, color, or combination thereof. For each position in the barcode, the corresponding set of probes for each oligonucleotide tag at that position is allowed to hybridize to the cells in situ. The process is repeated for each position in the barcode. Therefore, the observed pattern of optically detectable barcodes will be dictated by the order of oligonucleotide sequences in the barcode. Accordingly, the barcode may be determined by the optical readout obtained with sequential hybridization of probes.

In certain example embodiments, a set of fluorescently labeled probes specific to each oligonucleotide tag segment of the barcode may be sequentially hybridized to the cells in situ, for example, using sequential FISH. Each probe is labeled with a different fluorophore. Therefore, the sequence and order of the oligonucleotide tags in the barcode will dictate the order of colors observed using fluorescence microscopy allowing the barcode sequence to be determined optically.

In one example embodiment, a method of single cell gene expression profiling comprises delivering a nucleic acid construct encoding a fusion protein and a construct RNA sequence to a cell or population of cells. For embodiments utilizing viral vectors, the cell or cells are transduced with the constructs at a low multiplicity of infection. In certain example embodiments, the cells may be subsequently subjected to chemical selection to ensure that all cells have a stable single-copy of the constructs. For example, the constructs may encode an antibiotic resistance gene and chemical selection is carried out by exposure of the cell or cells to a corresponding antibiotic. Alternatively, for those embodiments employing a detectable self-reporting molecule, such as GFP, the self-reporting molecule may be used to assess successful. Cells expressing the self-reporting molecule may then be selected using known methods in the art, such as flow cytometry.

Methods for continuous monitoring of live cells are provided, comprising the steps of delivering into one or more cells one or more nucleic acid constructs as described herein, expressing the nucleic acid construct in the one or more cells; capturing cellular RNA transcripts expressed in the one or more cells by binding the cellular RNA via the cellular RNA capture element of the construct RNA sequence; exporting the cellular RNA from the cell by binding of the fusion protein construct RNA capture element to the retrieval element of the construct RNA such that the cellular RNA is exported from the cell in association with the secretion-inducing domain, wherein the secretion-inducing domain self-assembles to form an export vesicle; and isolating the exported vesicles containing captured cellular RNA transcripts at one or more time points.

In certain example embodiments, the method further comprises generating a RNA-DNA duplex by reverse transcribing the captured cellular RNA using the construct RNA sequence as a primer for reverse transcription. A DNA-DNA duplex is then generated by converting the construct RNA sequence to a corresponding DNA sequence with second strand synthesis using a DNA primer. The DNA-DNA duplex is then used to generate a sequencing library for sequencing using, for example, a NGS sequencing platform. Sequencing of the DNA-DNA duplex library identifies the transcript and—via the barcode information—the cell of origin for each transcript thereby enabling continuous single cell gene expression analysis.

In an aspect, the method can utilize an RNA construct sequence comprising a retrieval element, a filter, a barcode, a motif for binding to poly-A tails of cellular mRNAs. The method may comprise generating a RNA-DNA duplex by reverse transcribing the captured cellular RNA transcript using the construct RNA sequence as a primer for reverse transcription; generating a DNA-DNA duplex by converting the construct RNA sequence to a corresponding DNA sequence with a second strand synthesis using a DNA primer such that the barcode sequence is included in the DNA-DNA duplex; generating a sequencing library from the generated DNA-DNA duplexes; and sequencing the sequencing library to identify the captured cell mRNA transcripts wherein the one or more cells from which the cellular RNA transcripts were isolated are identified from the sequenced barcode. Template switching may be used to incorporate sequences from a template switching oligonucleotide. For example, a MLV reverse transcriptase- or similar reverse transcriptase—may be used to add non-template nucleotides to the first-strand cDNA when it reaches the 5' end of the mRNA. Template switching oligonucleotides designed to bind to these non-template nucleotides may then be used to facilitate template switching and incorporation of sequences complementary to the template switching oligonucleotide. In certain example embodiments, the template switching oligonucleotide may be used to introduce, in a 5' to 3' direction, a unique molecular identifier (UMI), a first sequencing primer binding site, and an adapter sequence.

Methods for labeling molecular components of the cell according to cell of origin can be utilized with the methods and constructs described herein. In an aspect, the construct comprises a barcode, a randomized nucleic acid sequence, and/or a searchable filter sequence (SEQ ID. NO: 13). The filtration sequence, as described herein, can be set a fixed distance from a barcode, when utilized, and can be used to identify the barcode in downstream, sequencing reads. The barcode can be attached to the cellular RNA by further priming second strand synthesis, by use of the nucleic acid construct to prime first strand synthesis of the captured cellular RNA template, or by ligation of the nucleic acid construct to the cellular RNA by RNA-RNA ligation. Amplifying the barcoded cellular RNA can be performed by a variety of methods, including PCR, RNA-dependent RNA synthesis, which can be facilitated by T7 RNAP. Amplification can also comprise linear DNA amplification by T7 polymerase. See, e.g. Shankaranarayanan, et al., Nature Protocols 7, 328-39 (2012).

Figure 30:
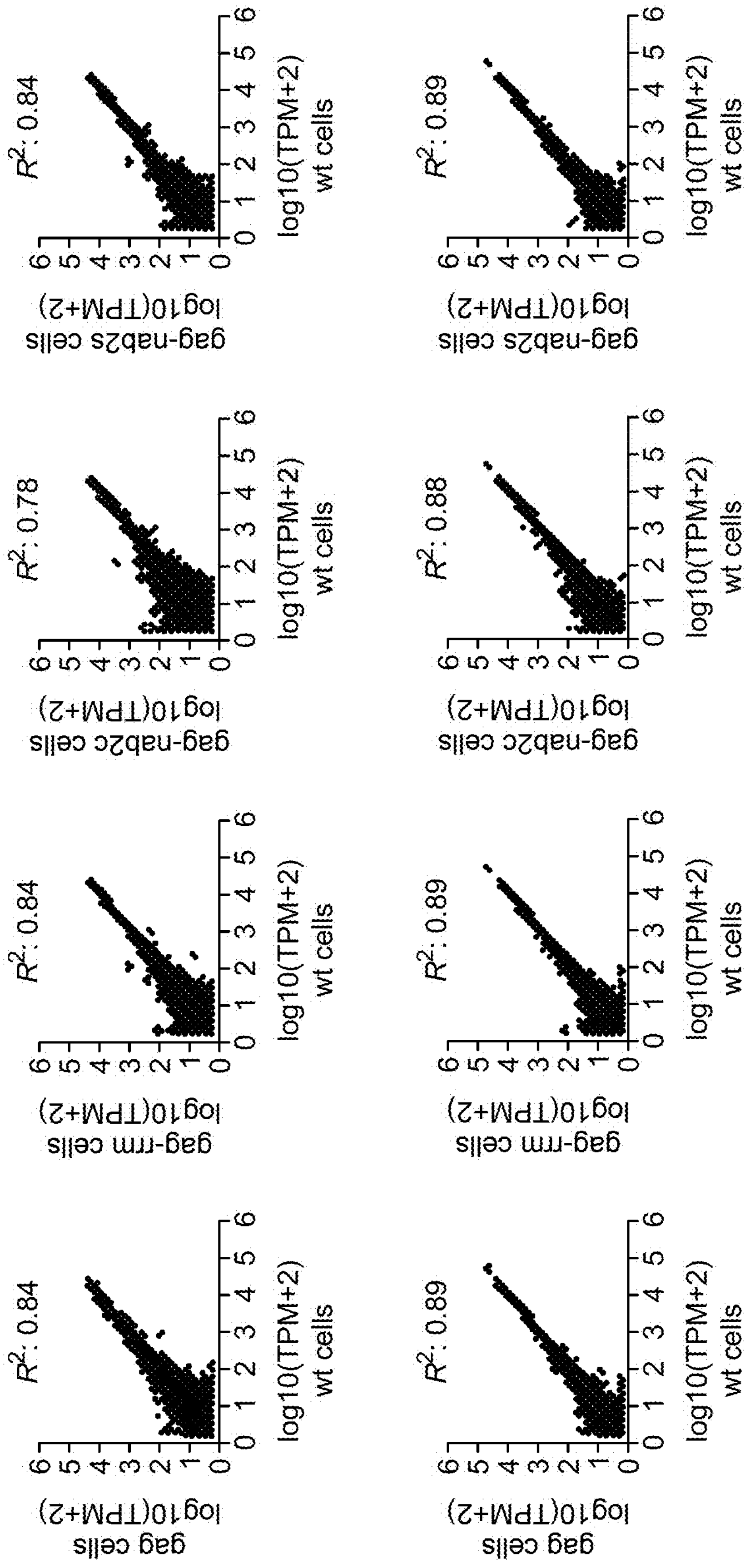
FIG. 30—Minimal transcriptome perturbation. Cellular self-reporting is minimally perturbative when conducting differential gene expression analysis (shown in separate figure).
Figure 31:
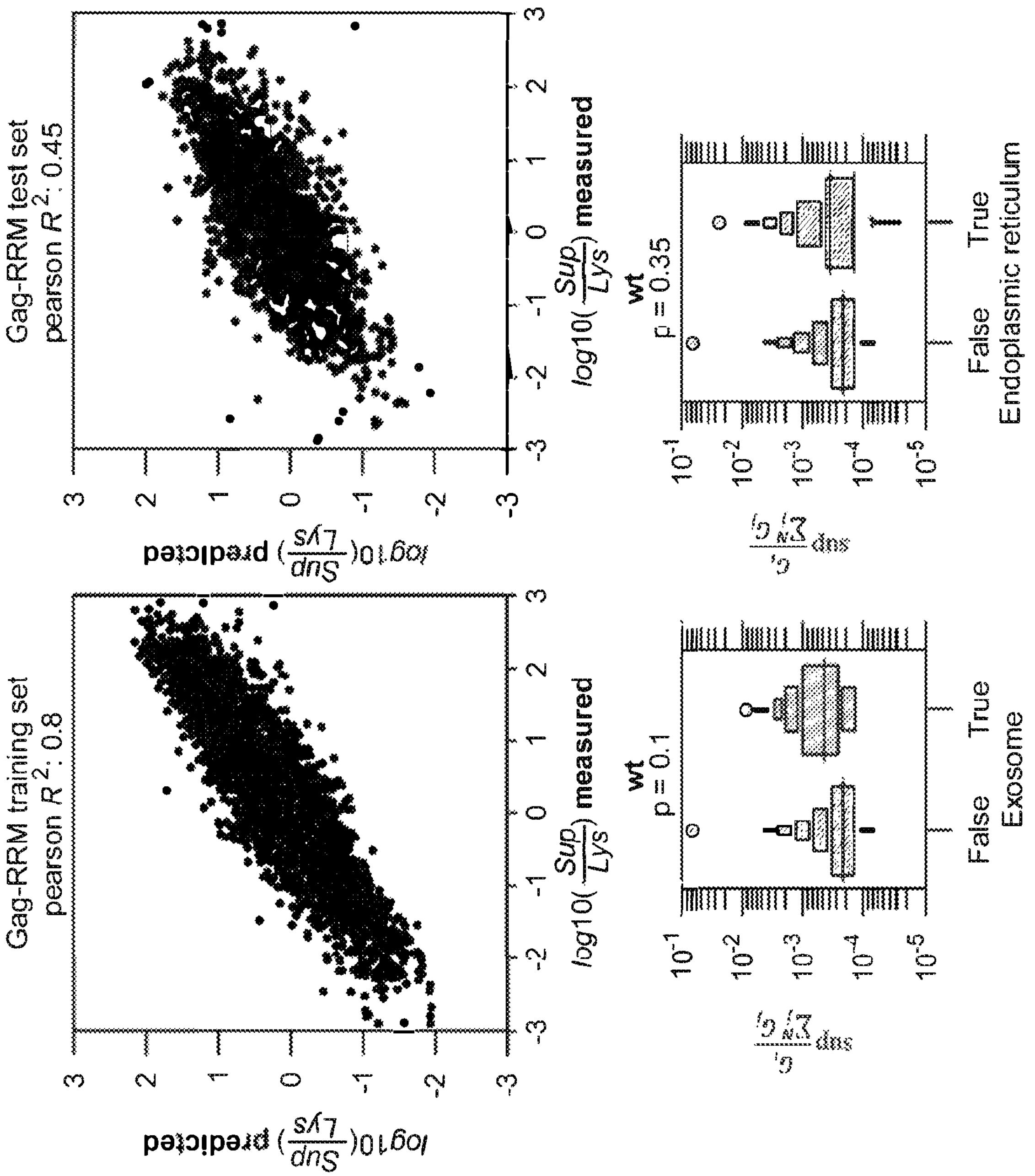
FIG. 31—Predictive model using gradient boosted. VLP exported RNA representation can be predicted using various RNA features, including RNA localization, GC content, length, and 7-mer overlaps between MLV genome and a transcript of interest.

Delivery of the construct can be by the viral or non-viral vectors disclosed herein, with a preferred delivery in lentiviral vectors. In an aspect, the barcodes disclosed herein can be amplified by the cell and used to mark cellular components of the cell according to cell of origin. Quantitative analysis is achievable using the constructs and method disclosed herein. The sequencing of libraries of RNA exported can be quantified as there is minimal transcriptome perturbation when utilizing the methods as disclosed herein with self-reporting cells displaying normal behavior, phenotypes and growth rates, see. e.g. FIG. 30.

In an aspect, methods may comprise predicting representation of exported RNA. Predicting may comprise utilization of various RNA features, including for example RNA localization, GC content, length, and 7-mer overlaps between murine leukemia virus (MLV) genome and a transcript of interest.

Cells

The constructs, systems and methods herein can be used in a variety of cells. In certain embodiments, the cells are eukaryotic cells, in an aspect mammalian cells. As described herein, the methods are performed in vivo or in vitro.

In a particular method, the method measures transcriptomes of the cells of a particular organ or other site within the body in vivo. Exemplary organs include brain, heart, kidney, liver, intestine, thyroid, lungs, uterus, prostate, and pancreas. Additional sites within the body can comprise lymph nodes, salivary glands, intra-articular locations, intraocular, cervix, bladder, esophagus. In an aspect, transcriptome-wide measurements can be made in a cell population or cell (sub) population. As referred to herein, a "subpopulation" of cells preferably refers to a particular subset of cells of a particular cell type which can be distinguished or are uniquely identifiable and set apart from other cells of this cell type. The cell subpopulation may be preferably characterized by the methods as discussed herein. A cell (sub) population as referred to herein may constitute a (sub) population of cells of a particular cell type characterized by a specific cell state. A subcellular population includes one or more of the structures within a cell, subcellular organisms or organelles, including Golgi apparatus, smooth+rough endoplasmic reticulum, nucleus and mitochondria.

In an aspect, it may be desirable to deliver and/or target tumor sites or other targeted locations in an in vivo context. With regard to targeting moieties, mention is made of Deshpande et al, "Current trends in the use of liposomes for tumor targeting," Nanomedicine (Lond).8 (9), doi: 10.2217/nnm.13.118 (2013), and the documents it cites, all of which are incorporated herein by reference. Mention is also made of WO/2016/027264, and the documents it cites, all of which are incorporated herein by reference. And mention is made of Lorenzer et al, "Going beyond the liver: Progress and challenges of targeted delivery of siRNA therapeutics," Journal of Controlled Release, 203:1-15 (2015), and the documents it cites, all of which are incorporated herein by reference.

In one aspect, the method comprises measurement of organisms, such as mice, by utilizing the cellular self-reporting constructs and methods described herein for in vivo delivery. In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example, a mammal. Also, the organism may be an arthropod such as an insect. The organism also may be a plant or a yeast. Further, the organism may be a fungus.

The compositions described herein may be used to introduce into a host cell, such as an eukaryotic cell, in particular a mammalian cell, or a non-human eukaryote, in particular a non-human mammal such as a mouse, in vivo. Delivery of the composition may for example be by way of delivery of a nucleic acid molecule(s) coding for the composition, which nucleic acid molecule(s) is operatively linked to regulatory sequence(s), and expression of the nucleic acid molecule(s) in vivo, for example by way of a lentivirus, an adenovirus, or an AAV.

A culture medium for culturing host cells includes a medium commonly used for tissue culture, such as M199-earle base, Eagle MEM (E-MEM), Dulbecco MEM (DMEM), SC-UCM102, UP-SFM (GB3CO BRL), EX-CELL®302 (NICHIREI®), EX-CELL®293-S (NICHIREI®), TFBM-01 (NICHIREI®), ASF104, among others. Suitable culture media for specific cell types may be found at the American Type Culture Collection (ATCC) or the European Collection of Cell Cultures (ECACC). Culture media may be supplemented with amino acids such as L-glutamine, salts, anti-fungal or anti-bacterial agents such as FUNGIZONE®, penicillin-streptomycin, animal serum, and the like. The cell culture medium may optionally be serum-free.

Kits

Based on the methods disclosed herein, self-reporting libraries and/or cell lines comprising self-reporting constructs may be constructed and provided and present methods applied to provide cost-effective monitoring and/or profiling. Accordingly, a product comprising completed libraries, or a kit for making the libraries according to principles of the present invention are possible. For some applications it may make sense to focus on a subset of cell types or subpopulations for which the kit would be particularly appropriate. Accordingly tailoring the self-reporting constructs for targeting of particular cell types, target molecules, or other feature is envisioned.

In addition, monitoring platforms and self-reporting investigations of transcriptomes could be provided as a service. That is, a customer may provide one or more samples to an entity for constructing self-reporting molecules according to customer objectives and/or sample, applying the steps of the present invention and providing as its result a report of the transcriptome profiles desired and/or libraries tailored for customer need.

The embodiments are further described in the following examples, which do not limit the scope of the invention described in the claims.

EXAMPLES

Example 1—Continuous Monitoring Constructs

Mammalian cells turn over approximately 14% of the transcriptome per hour on average (Yang E, Genome Research 2003), and simulations (described below) show that mRNA can theoretically be exported in VLPs at 100% of the cell's normal synthesis rate. By sampling at 25% of the turnover rate, 3% of the total transcriptome could be sampled per hour, or 500-15,000 transcript molecules per hour. By fine-tuning the transcriptional and translational dynamics of export compartment production, cellular RNA should be sampled at a specified rate of 0.1% to 3% of the normal synthesis rate. Even with estimated sample preparation methods that are approximately 50% efficient, detection of 250-7500 collected transcript molecules per cell per hour can be achieved. This 'integration time' can be varied to resolve the necessary timescales associated a particular question. A tunable trade-off exists between temporal resolution and the degree of perturbation to the cell.

Packing of 28-150 transcripts per VLP inner surface is estimated. This estimate is derived from a range in VLP radius of 80-130 nm and an mRNA radius of gyration of 16.8-20.8 nm (mRNA radius of gyration from Gopal A, RNA 2012). With these numbers in mind, it is possible to calculate that the burden of VLP production necessary to collect 15,000 transcript molecules per hour corresponds to as little as 0.01% of the cell's total protein (total protein per cell count from Siwiak M, PLOS ONE 2013).

Figure 4A:
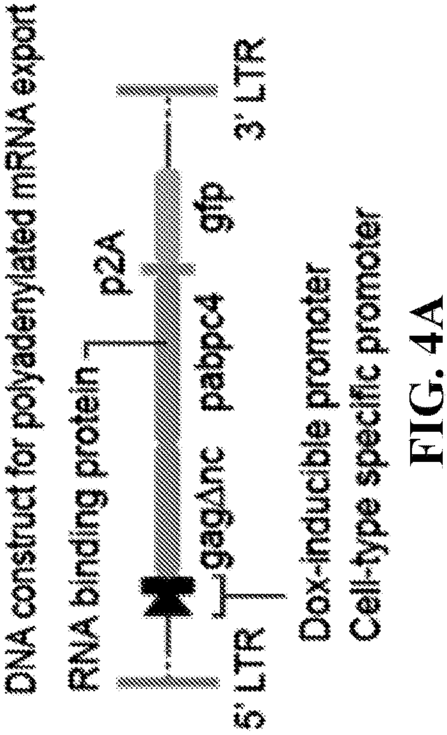
FIG. 4—is a schematic of single cell expression analysis using an example inducible construct further encoding a construct self-reporting molecule that may be used to indicate successful delivery to target cells, in accordance with certain example embodiments.
Figure 4B:
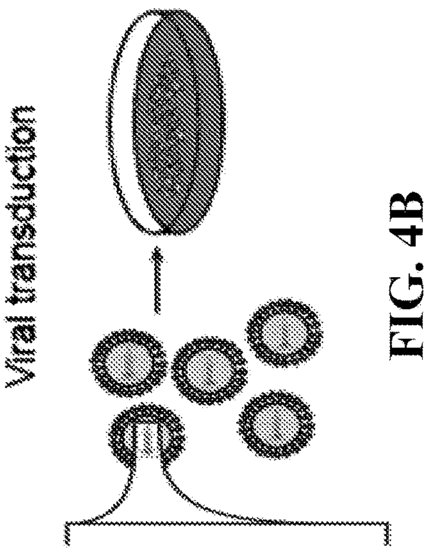
Figure 4C:
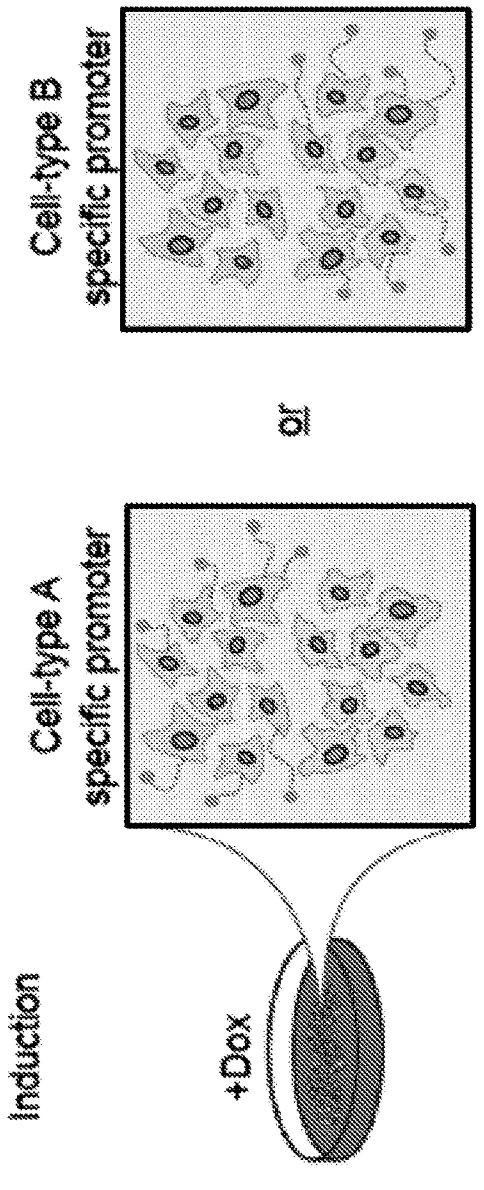
Figure 5A:
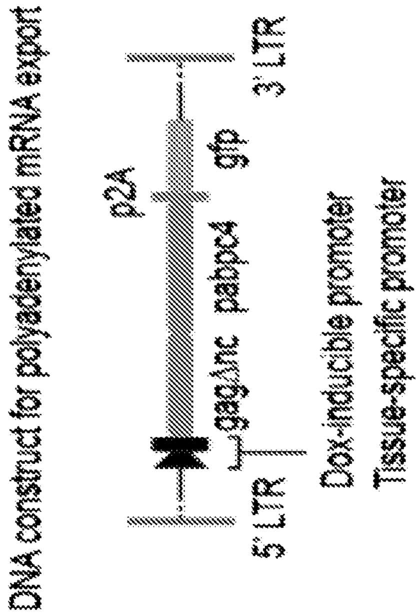
FIG. 5—is a schematic showing an example construct comprising a tissue-specific promoter, a dox-inducible promoter or a combination of the two, a linker, and labile self-reporting molecule and the use of said construct in accordance with certain example embodiments.
Figure 5B:
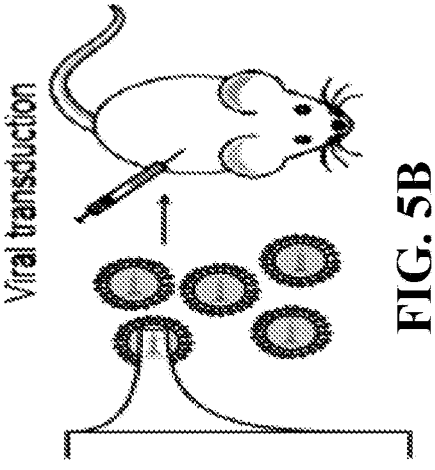
Figure 5C:
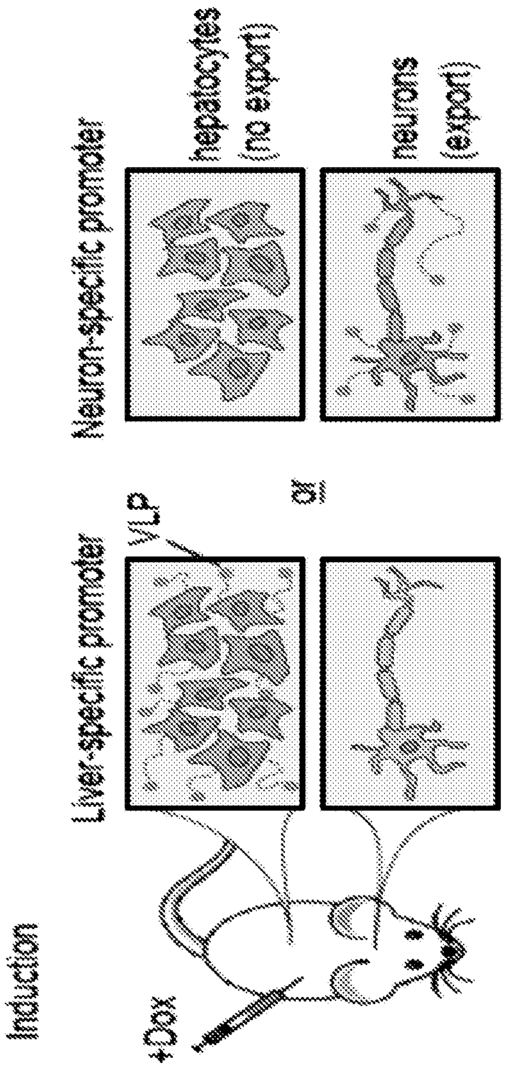
Figure 5D:
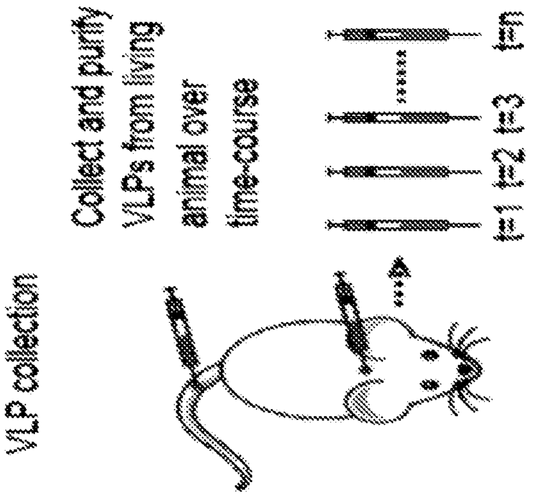

To export mRNA in a minimally-biased manner for genome-wide expression profiling, a Gag-PABP fusion was constructed and export tested from HEK293 cells. The construct is safe and replication-deficient, as it contains neither reverse transcriptase nor integrase. See FIG. 3. Poly(A)—binding protein (PABP), which binds to the poly (A) sitail of mRNA, can be used as an mRNA binding domain for synthetic mRNA export machinery. The PABP domain will recruit mature transcripts from the cytoplasm, while the Gag domain will allow for export of captured mRNA through membrane budding and VLP formation. The overall rate of export can be optimized for the desired sampling frequency and cell type by controlling the Gag-PABP fusion expression level. A rate of VLP export of mRNA can be determined by carrying out highly controlled VLP collection experiments with an inducible Gag-PABP fusion from a known number of cells. RNA from the VLPs can then be extracted and used to prepare RNA-Seq libraries (FIG. 4) with unique molecular identifiers and a spike-in control (ERCC™ from LIFE TECHNOLOGIES®). By comparing the RNA-seq of bulk cell lysate of self-reporting cells to the lysate of normal cells, the transcriptional defect caused by the VLP export system can be detected. Similar analysis of the extracted VLPs compared to bulk controls can be used to estimate mRNA export per cell per unit time and any sampling biases (e.g. against large transcripts). These tests are carried out over a range of different promoter strengths to find the optimal expression rate, for all cells of interest. Next, GFP+self-reporting HEK293 cells are plated in such a way that there is 1 cell per well of a 384 well plate on average. To remain certain that GFP+ cells are self-reporting, GFP and Gag-PABP are delivered in the same vector. This experiment allows the plate to be imaged to determine the number of GFP+self-reporting cells, the media retrieved to collect VLPs. After collection, VLPs are purified by standard virus purification protocols. VLP lysis is carried out using standard lysis techniques, and 11lumina-ready DNA libraries are constructed using SMART-SEQ2™ (Picelli S, Nature Protocols 2014). By indexing the media from each well separately through the SMART-SEQ2™ protocol, the sequencing reads can be traced to the original wells to determine the accuracy of VLPs as reporter systems. This can enable GFP expression as a function of time to be observed, and a correlation between GFP reads and cell fluorescence to be determined. The individual cells are collected at the final time point and collected and prepared for RNA-Seq in the same plate.

Example 2—Barcoded Constructs

Contents from single cells are barcoded by expressing a unique randomized RNA sequence with a MS2 hairpin. By hybridizing these barcodes to export mRNA, a barcode-mRNA hybrid can be created with reverse transcription after collecting VLPs. To test single-cell mRNA barcoding and export strategy, a modified version of the collection methods described above are used. Gag is fused to a MS2 coat protein, which binds the MS2 RNA hairpin with nanomolar binding affinity. By transducing or transfecting cells with a MS2 hairpin containing a cell-specific unique random barcode and a 3' polyU sequence, it is possible to capture and export mRNA in an unbiased fashion, with each transcript stably hybridized to the barcoded MS2 capture probe by the poly(A): poly(U) interaction. After VLP collection transcript sequences are permanently linked to the cellular barcodes by utilizing the barcoded MS2 transcript as a primer for reverse transcription (RT). Such RNA-primed RT has been previously demonstrated and even shown to result in higher fidelity than DNA-primed RT (Oude E, JBS 1999). Further, M-MULVRT enzyme has been shown to use both RNA and ssDNA as a template (Verma, B B A 1977), allowing the RNA-DNA hybrids to be converted completely to DNA after a second strand synthesis step with a DNA primer. See FIG. 1.

The molecular biology steps are tested using in vitro transcribed barcoded MS2 hairpin RNA and purified total RNA. The (UUG), motif in the capture sequence is used to prevent early transcriptional termination from pol111 promoters, as a stretch of 4 or more uracil bases leads to a 90% transcription termination efficiency (Orioli A, NAR 2011). Reverse transcription with a (TTG) DNA primer has been verified as efficient as its poly(T) analogue. The in vitro experiment are read out by RT-qPCR of Gapdh-MS2 fusion cDNA. Next, the same assessment is performed using supernatant from transduced HEK293 cell lysates to demonstrate and optimize endogenous transcript capture by the MS2 barcode transcript. Transcript capture and RNA-primed RT from secreted VLPs from bulk HEK293 cultures are tested and complements the RT-qPCR readout with RNA-Seq of the fusion products (including spike-in controls) to determine export rates and bias compared with total lysate from the same cell population.

Example 3

Single-cell trans-differentiation trajectories can be monitored by delivering unique RNA barcodes along with the Gag export machinery described here. To do this we can transduce HT1080 fibroblasts with unique RNA barcodes as well as Gag export machinery. Further, can same HT1080 fibroblasts can be transduced with a MyoD construct to initiate the trans-differentiation to a myoblast lineage. Bulk population controls and single-cell controls (without export machinery) along the time course can be used to validate the observed cell-states along each trajectory. By collecting supernatant, and building single-cell barcoded libraries with methods described here, temporal RNA information can be tied back to each individual cell of origin. After carrying out dimensionality reduction and other machine learning techniques on the RNAseq data, it is possible to map single-cell trans-differentiation trajectories.

Example 4—Nuclear Export of Barcoded Constructions

Figure 16A:
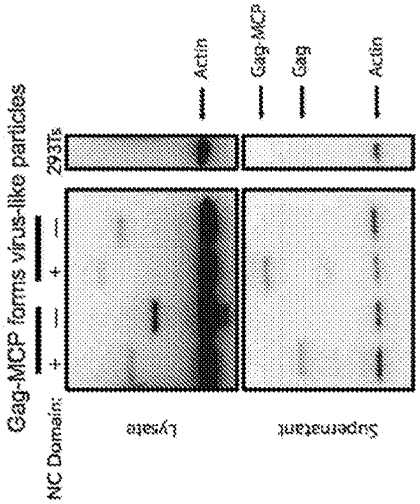
FIG. 16A-16C-FIG. 16A Gag-MCP (Gag-MS2) forms VLPs as demonstrated by an anti-Gag western supernatant.
Figure 16B:
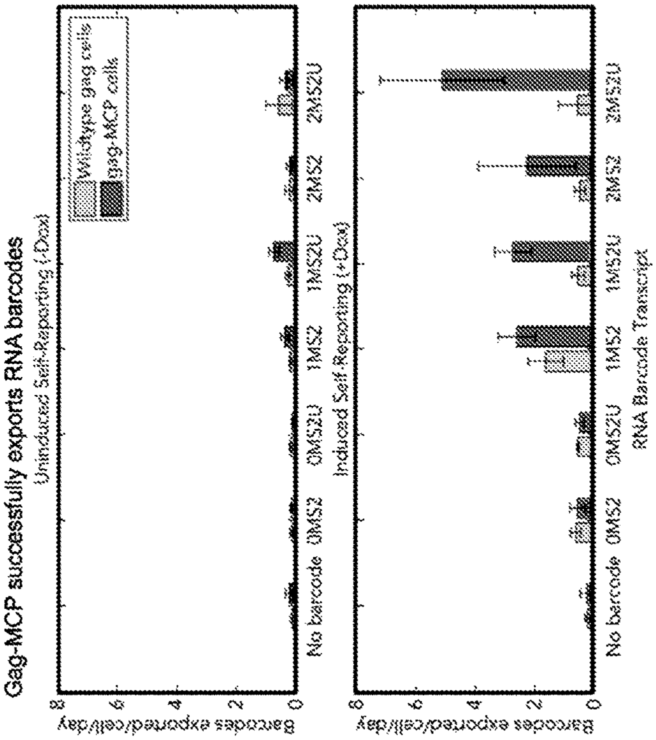
Figure 16C:
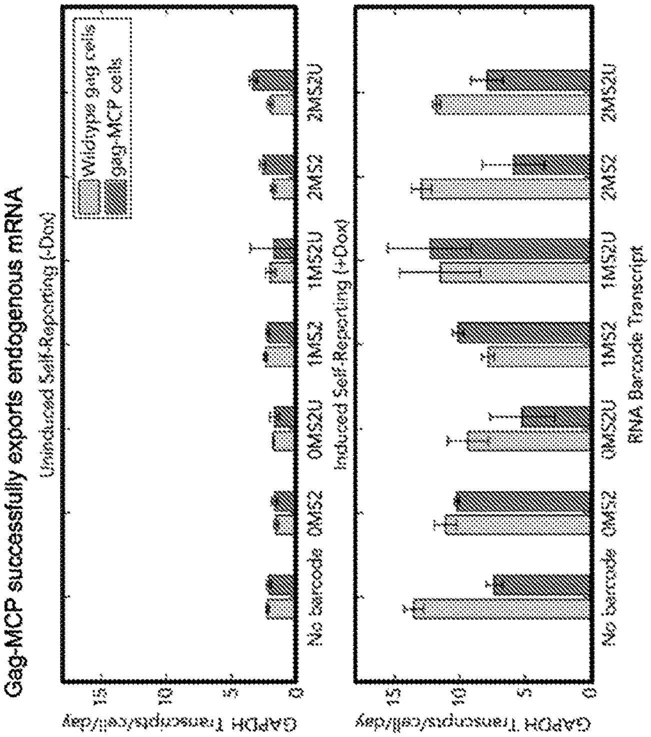
Figure 17A:
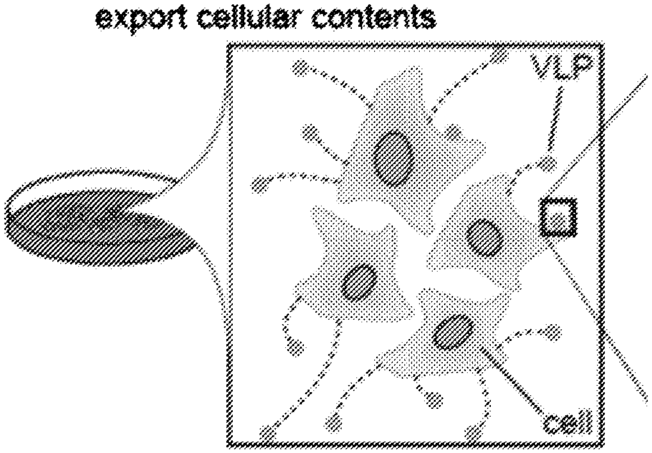
FIG. 17—Overview of self-reporting technology, including methods of measuring gene expression from live cells.
Figure 17B:
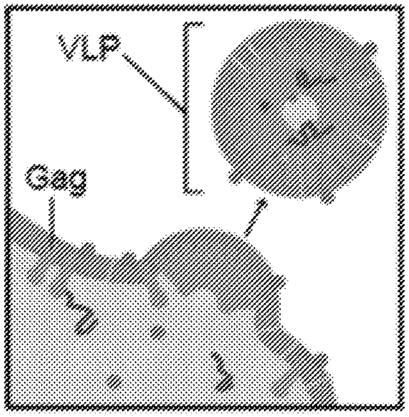
Figure 17C:
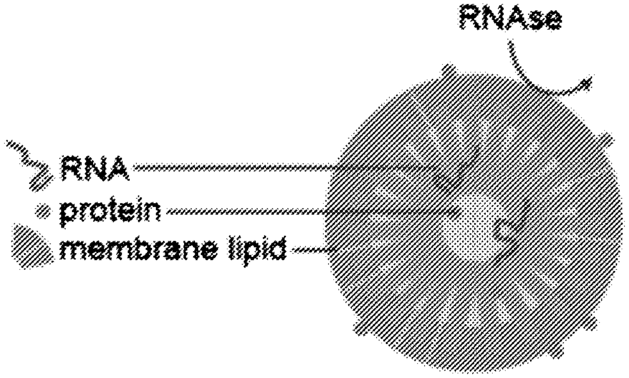
Figure 17D:
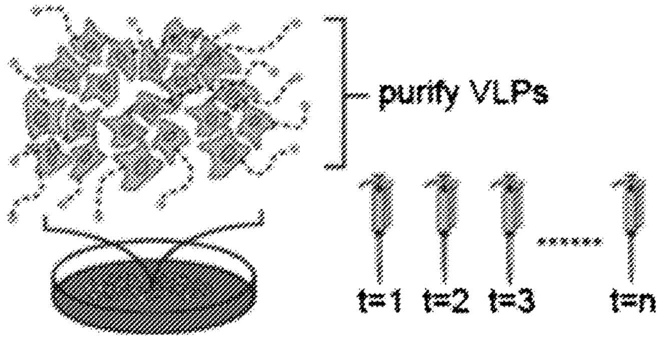
Figure 17E:
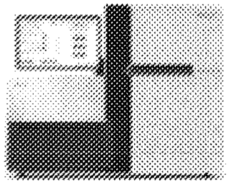
Figure 17F:
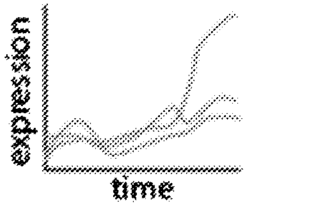
Figure 18:
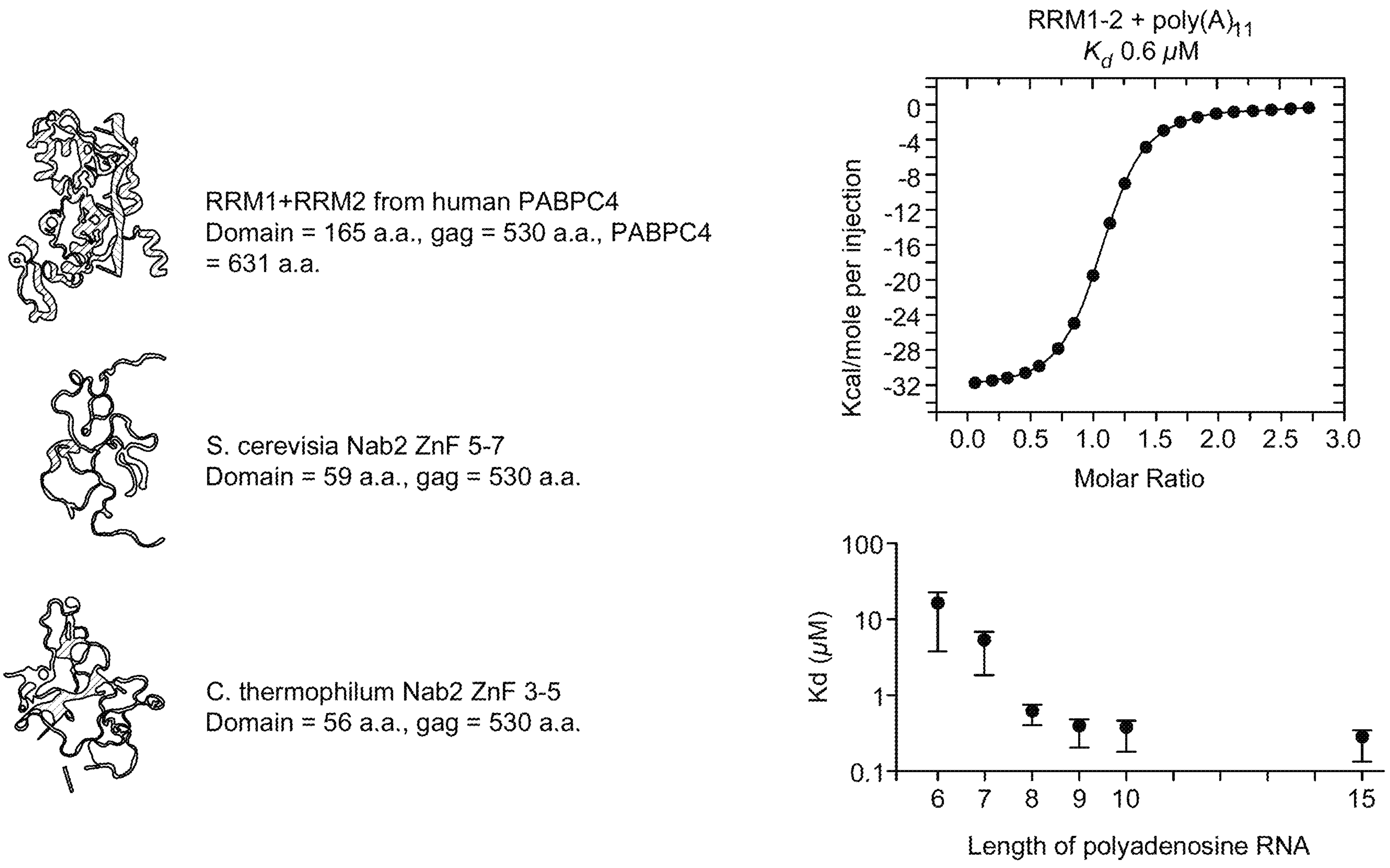
FIG. 18—Overview of exemplary fusion proteins of Gag to small poly(A) binding domains, with poly(a) binding domain structures.

Self-reporting enables a non-destructive assessment of a cell's transcriptional state by packaging representative fractions of a cell's transcriptome into virus-like particles (VLPs), which are subsequently exported from the cell into the culture environment. In population culture of self-reporting cells, genetic encodings may be needed to map the RNA exported with VLPs to the cell of origin. Thus, a synthetic transgene was engineered to encode cell state information (e.g. cell type, cell lineage, genetic perturbation, etc.) into an RNA transcript-termed an RNA barcode—for packaging and export with VLPs. RNA barcodes are designed to be U6 promoter driven, small RNA transcripts that can be stably expressed in cells via viral delivery. Gag viral proteins bind and complex with cytoplasmically expressed RNAs. Thus, nuclear export of the RNA barcode is achieved by including the Rev Response Element (RRE) in the 5' of the transcript and independently co-expressing the HIV-1 Rev viral protein from the same lentiviral vector. Upon expression, Rev protein binds its cognate RRE motif within the RNA barcode transcripts to promote Ran-GTP mediated nuclear export. The RNA barcode transcripts also contain MS2 hairpins that can bind the MS2 coat protein (MCP) domain within gag-MCP fusion proteins to specifically enrich the packaging of RNA barcode transcripts within gag-MCP VLPs. See FIG. 16.

Example 5—Fusing Gag to Small Poly(A)—Binding Domains

Figure 19:
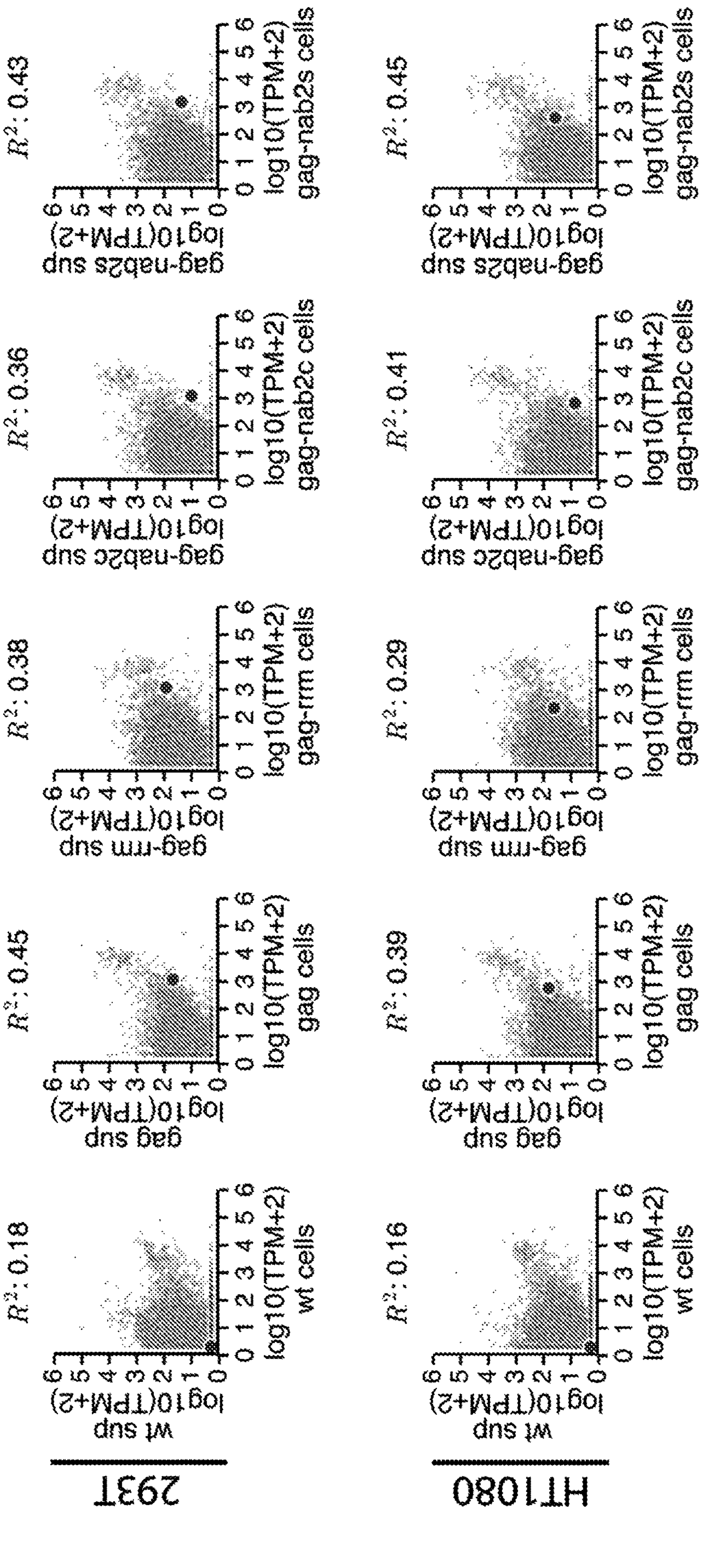
FIG. 19—Graphs showing representation of various VLPs from supernatant of 293T and HT1080 cells.
Figure 20:
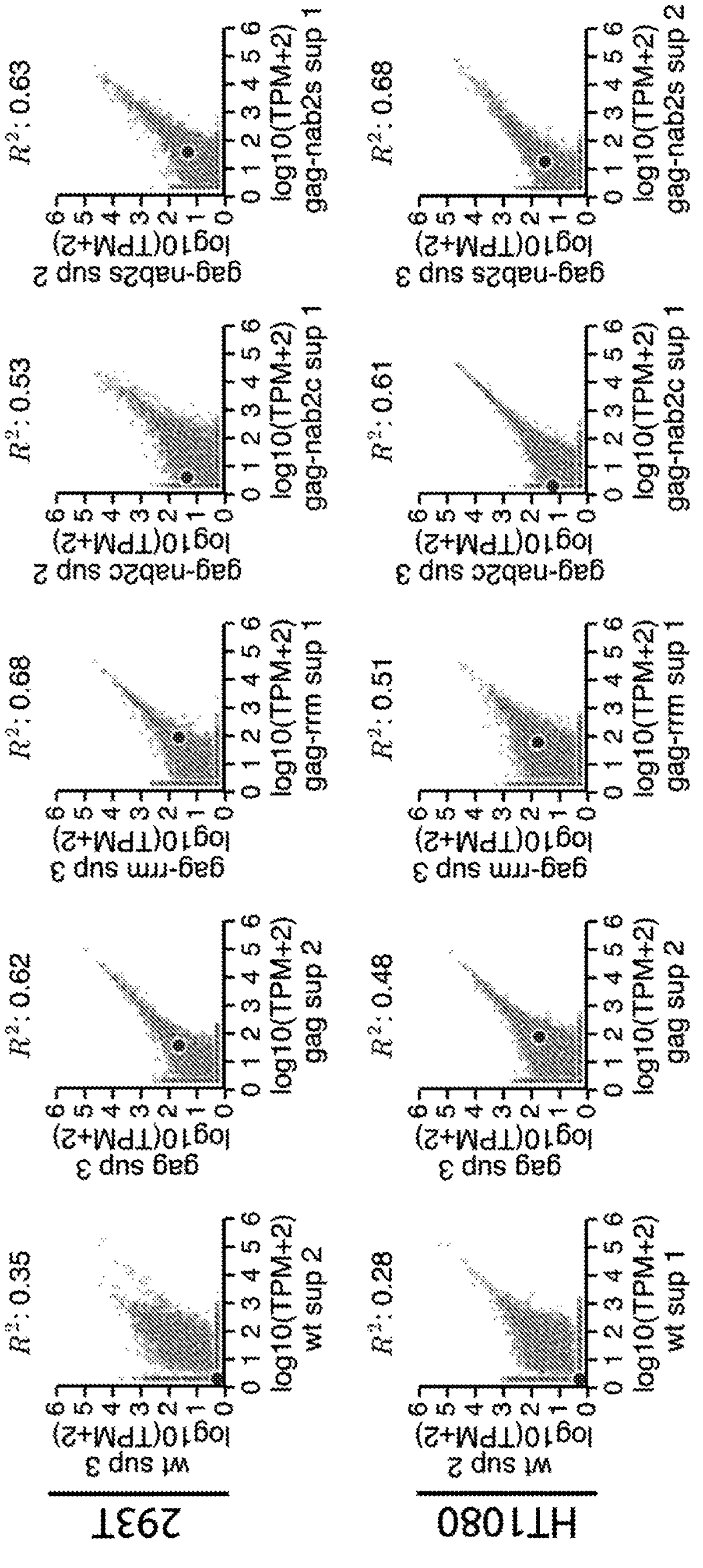
FIG. 20—Graphs showing quantitative VLP export from 293T and HT1080 cells.
Figure 21:
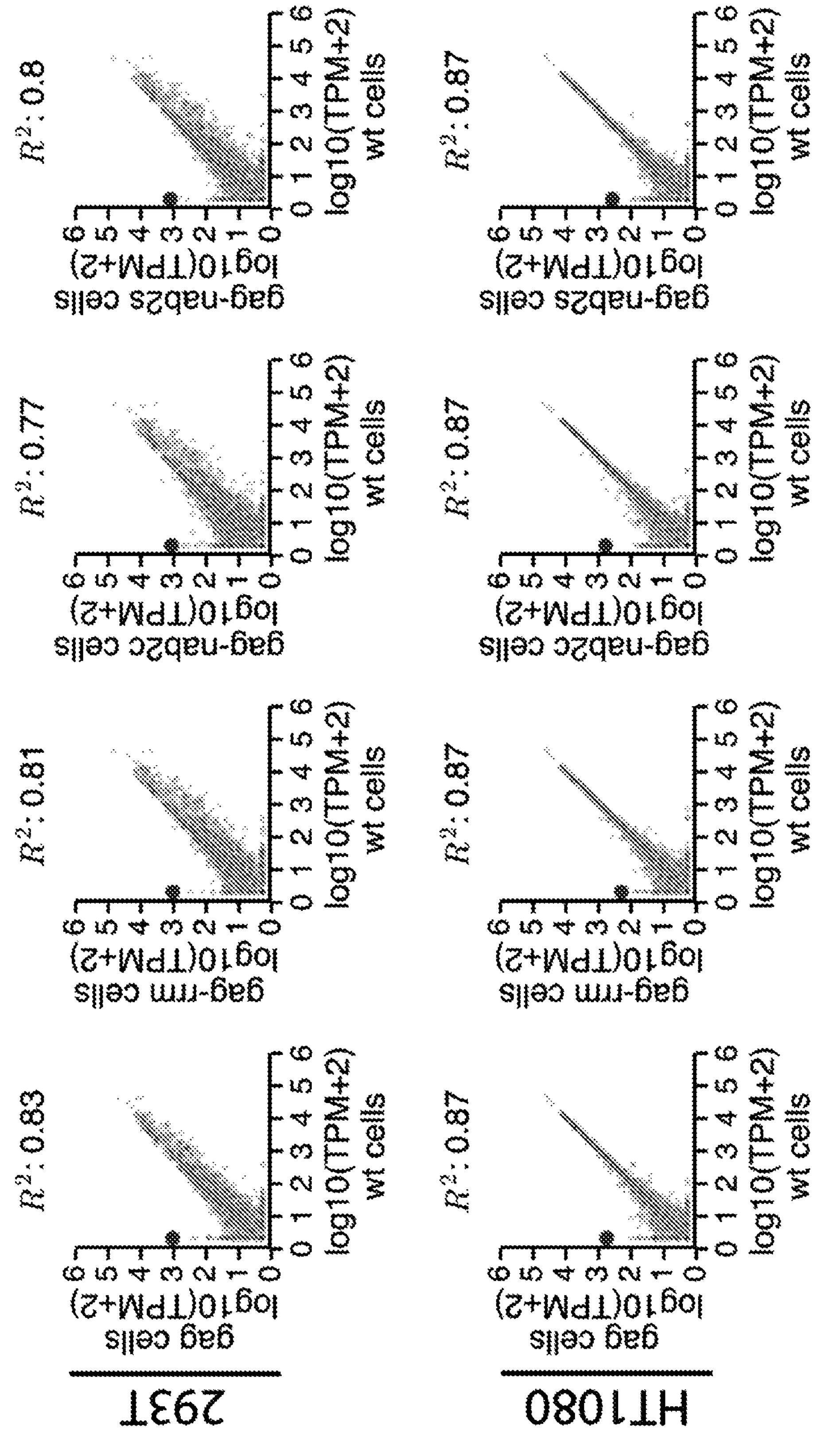
FIG. 21—Graphs showing that cells are not perturbed by RNA export process using small poly(A) binding domains fused to Gag.
Figure 22:
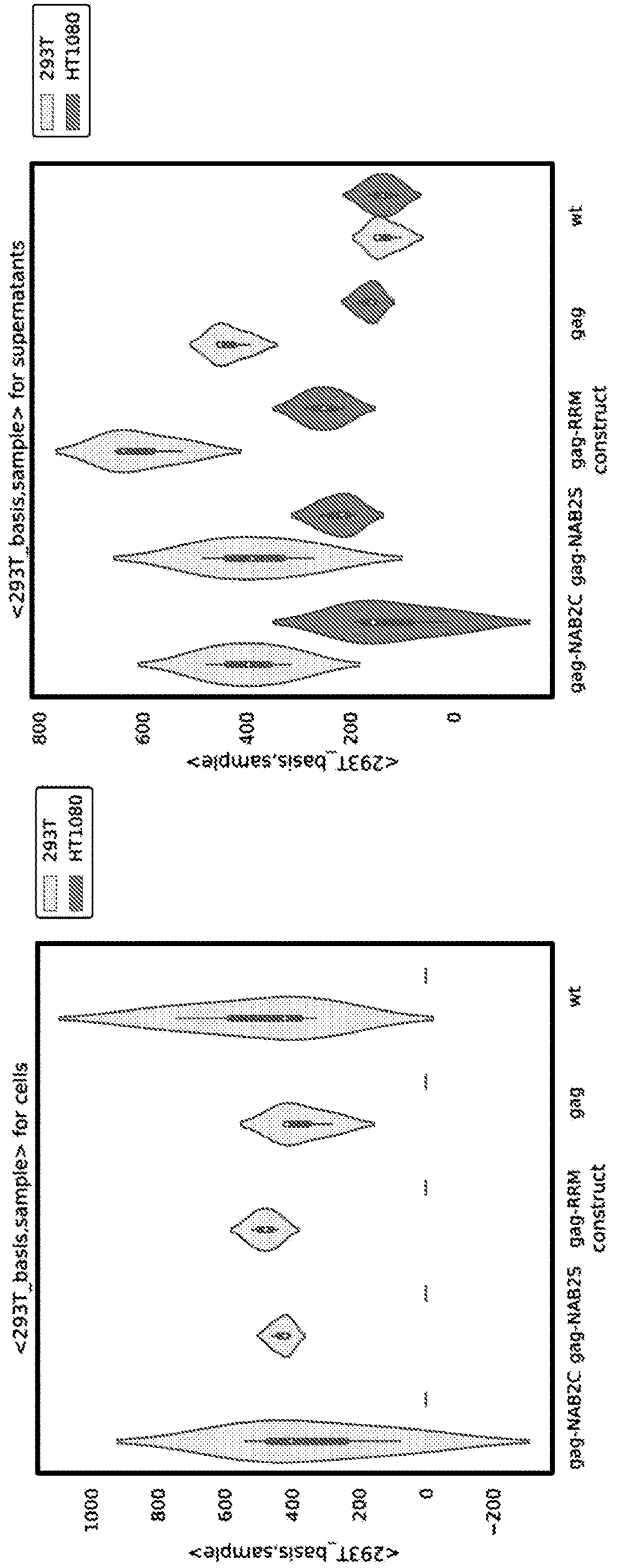
FIG. 22—Classification via projection in 293T cells.
Figure 23:
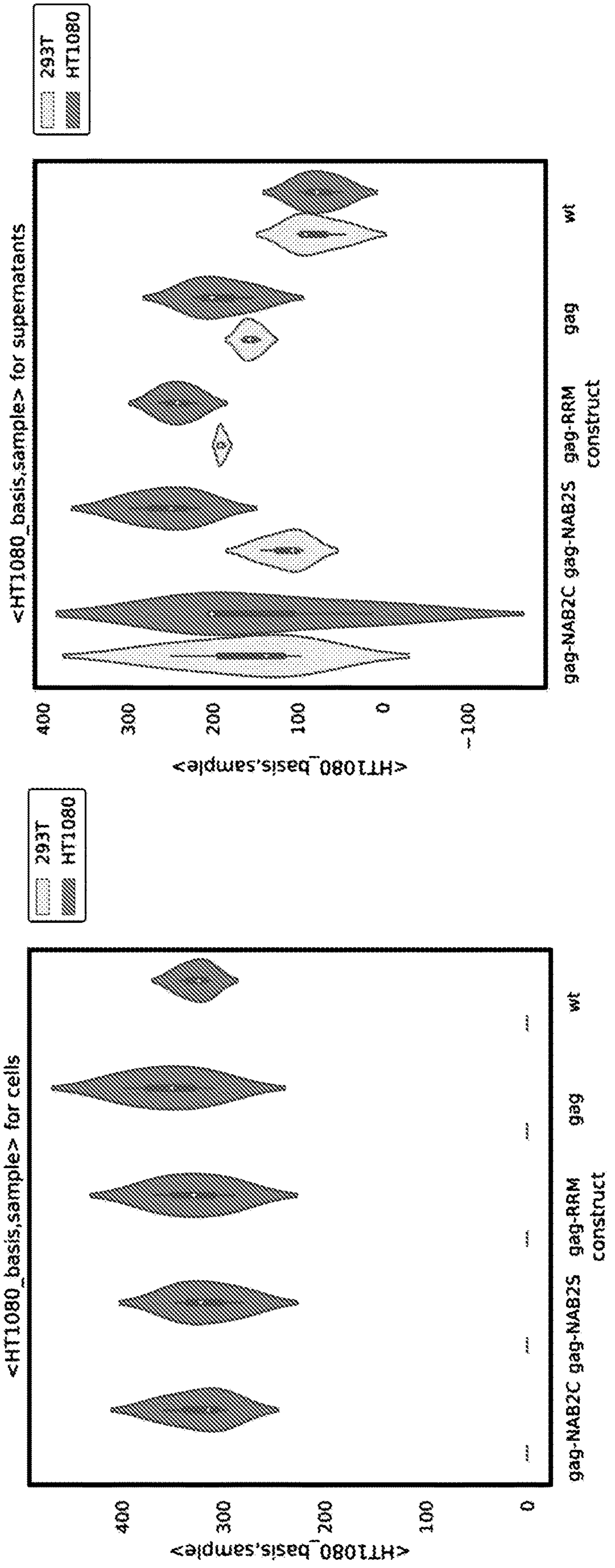
FIG. 23—Classification via projection in HT1080 cells.
Figure 24:
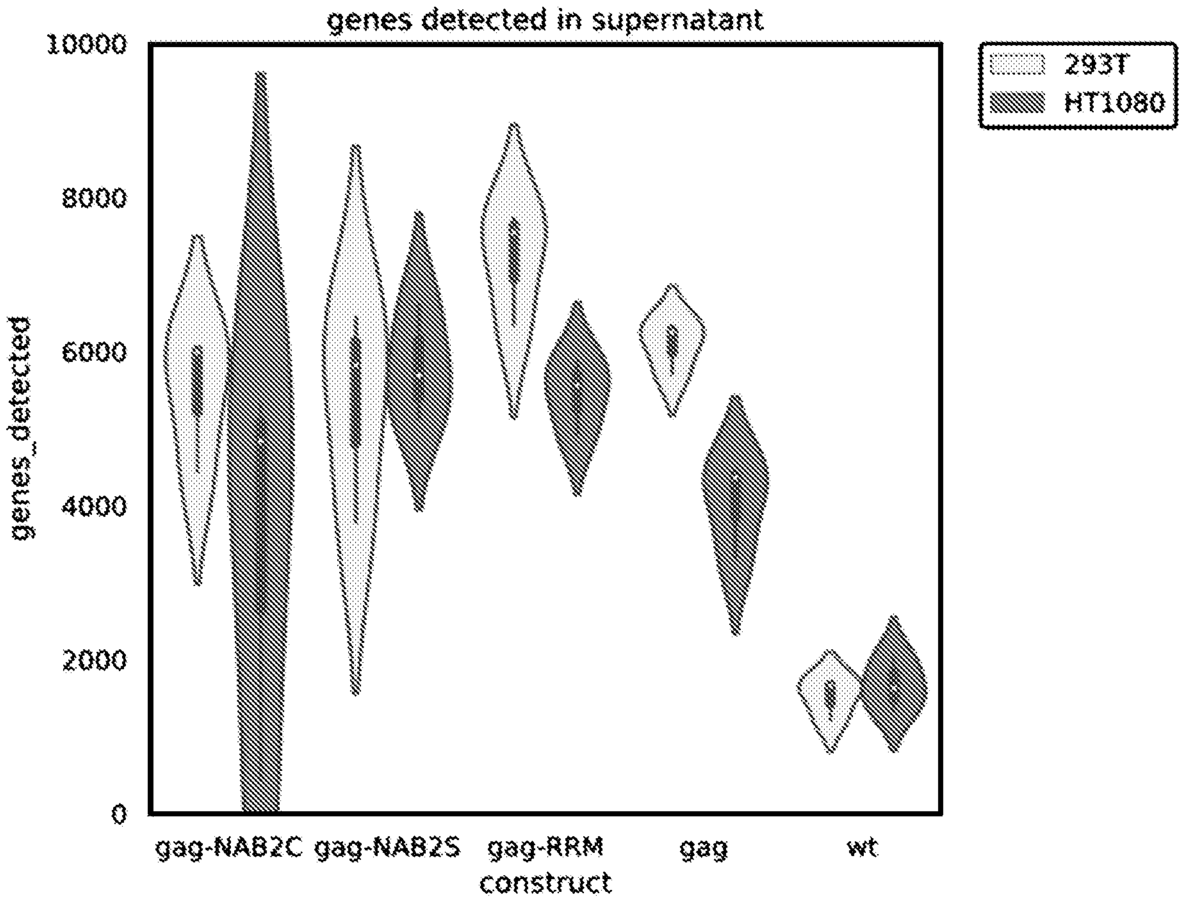
FIG. 24-Gag fusion export repertoire plotting genes detected in supernatant, including with gag-Nab2 C. thermophihurn (NAB2C) construct, gag-Nab2 *S. cerevisiae* (NAB2S) construct and gag-RRM1-2 construct.
Figure 25:
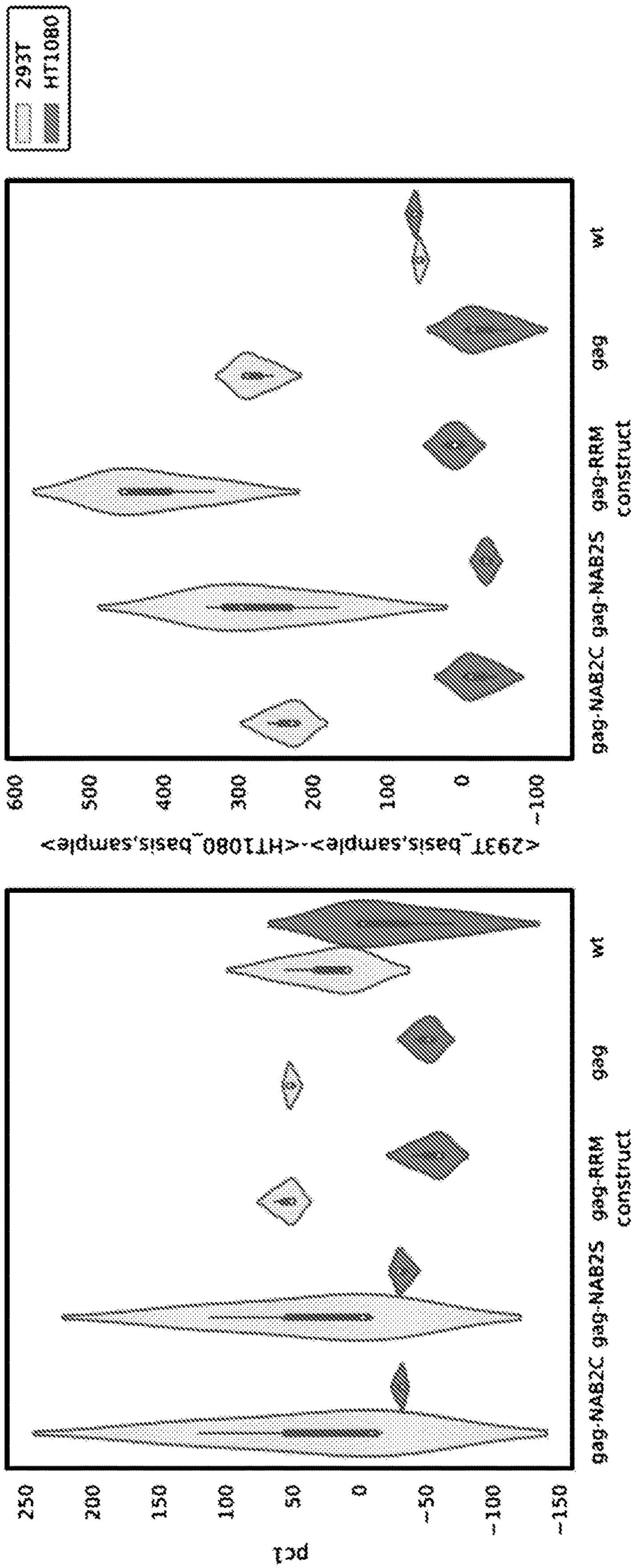
FIG. 25-Gag fusions with small poly(a) binding domains such as NAB2C, NAB2S and RRM1-2 allow cell type classification.

An overview of an exemplary cellular self-reporting process is provided in FIG. 17. Fusion of small poly(A) binding domains to Gag proteins as described herein can lead to an increase in exported RNA. This was monitored in supernatants of 293T or HT1080 cells (FIG. 19) as well as VLPs collected and purified from live cells (FIG. 20). RNAseq analysis revealed that cells are not perturbed by this process (FIG. 21). Results of analysis of different fusion constructs in 293T cells and HT1080 cells are also shown in FIGS. 22 and 23, respectively. Constructs involving small poly(A) binding domains generally facilitated export of more RNA per sample (FIG. 24) and these fusions allow for cell type classification, as illustrated in FIG. 25.

Example 6—VLPs Allow for Live-Cell RNA Measurement

Retrieving RNA information from living systems grants insight into biological state and response. However, there are no non-destructive methods to continuously retrieve and monitor transcriptome-wide RNA information from the same living samples. Applicants overcame this limitation by leveraging Gag polyprotein from murine leukemia virus (MLV), allowing RNA to be exported from living cells via virus-like particles (VLPs). With this approach, quantitative, transcriptome-wide RNA information can be collected with minimal perturbation from a variety of mammalian cells. Gag was rationally engineered to increase the repertoire of exported RNA, and also demonstrate multiplexed population readouts by utilizing affinity tagged envelope glycoproteins. Finally, brain transcriptomes of living, behaving mice will be measured by deploying cellular self-reporting in vivo.

High-throughput RNA measurement through RNA sequencing (RNA-seq) has proven to be a powerful information-rich method, lending insight into the biological states of cells, tissues and organs of several biological systems. However, traditionally, RNA-seq has been a destructive method, where biological samples are lysed for RNA extraction. This paradigm is limited, as transcriptional trajectories are unobservable for the same biological samples. sought to overcome This fundamental limitation by developing a non-destructive RNA-seq method capable of whole transcriptome readouts.

Previous non-destructive RNA measurements have been microscopy based, where RNA localization and approximate count can be observed via a variety of methods. However, these live-cell methods are unable to perform transcriptome-wide measurements, due to live-cell optical barcoding constraints, and are not suitable for in vivo measurements. More recently, molecular recording or molecular ticker-tape methods have allowed information to be stored in living systems, in order to be sequenced and extracted at one dedicated terminal end-point (n). While promising, these methods currently cannot record transcriptome-wide information, nor can they finely resolve the order of transcriptional events.

Figure 26F:
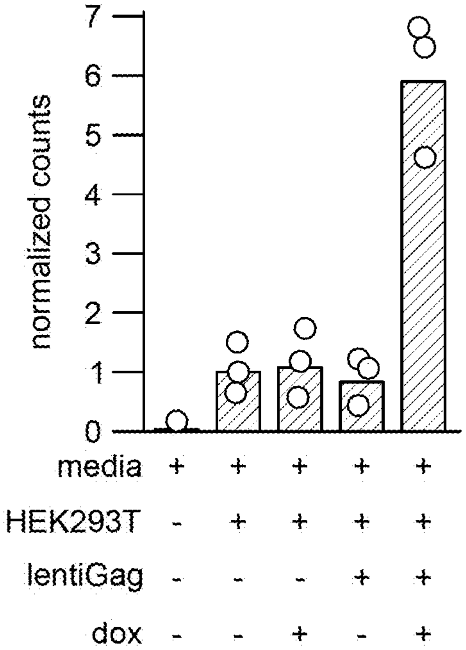
(FIG. 26F) RT-qPCR results from supernatants purified from wild-type and lentiGag+293T cell lines±doxycycline. GAPDH copy number was used as a proxy for exported RNA. Doxycycline induction led to VLP formation and RNA export.

It was previously found that retrovirus-based virus-like particles (VLPs) derived from transfecting HEK293T cells with Gag, the core structural polyprotein for retroviruses, package cellular RNAs non-selectively in the absence of cis-acting packaging signals. Applicants envisioned that this phenomenon could be leveraged to create a stable RNA export pathway, allowing live-cell transcriptome measurements from mammalian cells (FIG. 26A to 26D). To test this, a cell line was made by transducing HEK293T with replication-incompetent lentivirus packaging doxycycline-inducible murine leukemia virus (MLV) Gag fused to a P2A-linked GFP reporter to validate expression and translation (FIG. 26E). After induction with doxycycline, expression was confirmed via flow cytometry and purified supernatants via ultracentrifugation. RT-qPCR was then performed on the housekeeping gene GAPDH as a proxy measurement for the amount of exported RNA. Over a 48-hour period after doxycycline induction, there was a 5.9 +1.2 fold increase (mean±SD, n=3, p=0.0024) in exported GAPDH mRNA from Gag+dox-induced purified supernatant, relative to the uninduced wild type control (FIG. 26F), validating that Gag expression increases RNA export in living cells.

Figure 26G:
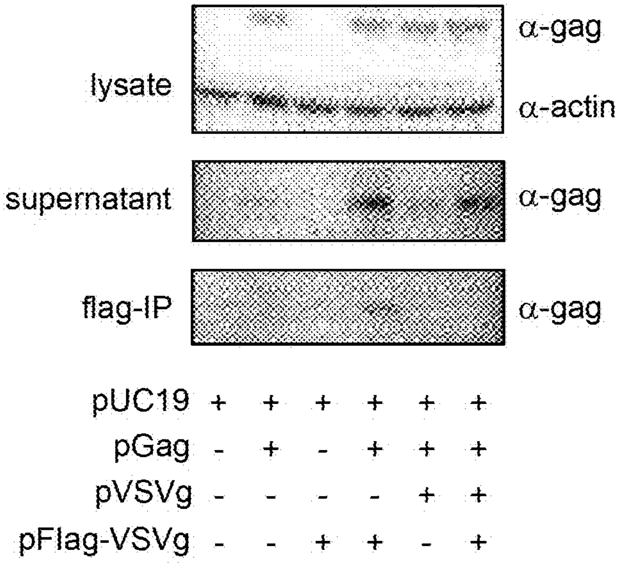
(FIG. 26G) Western blot on lysate, supernatant, and flag immunoprecipitation from 293T cell lines transfected with different constructs.
Figure 26H:
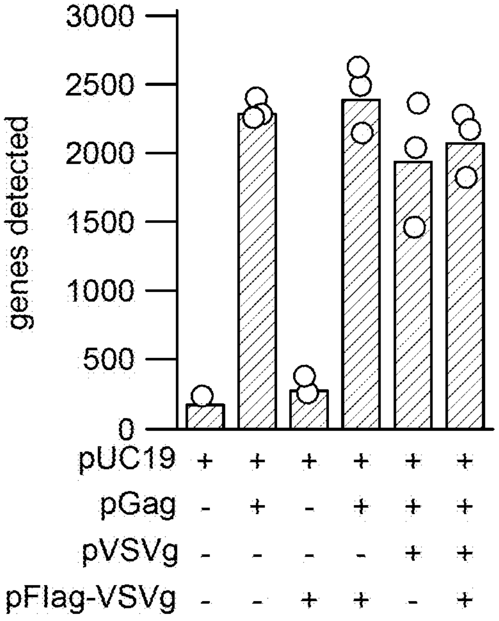
Figure 26I:
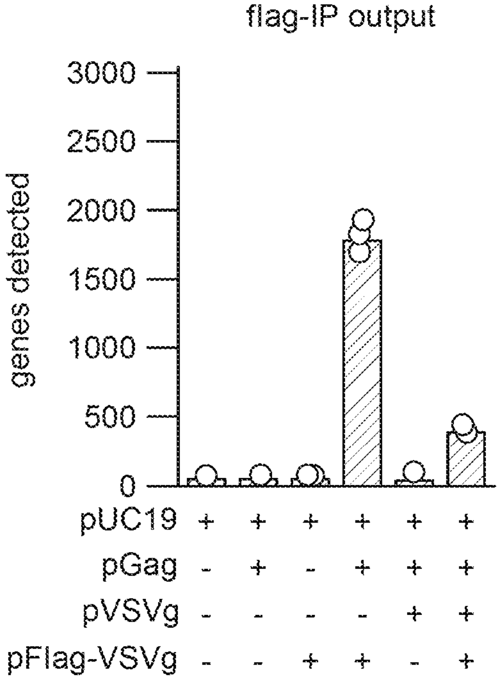
Figure 26J:
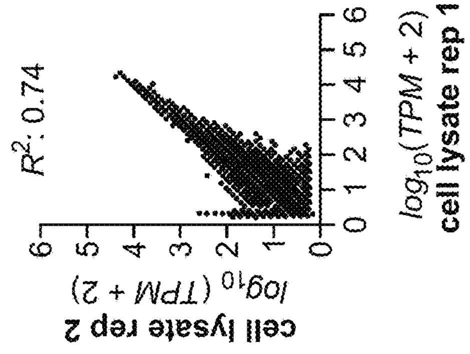
(FIG. 26J) RNA-seq replicate concordance of pGag+, pFlag-VSVg+293T cell lysates.
Figure 32:
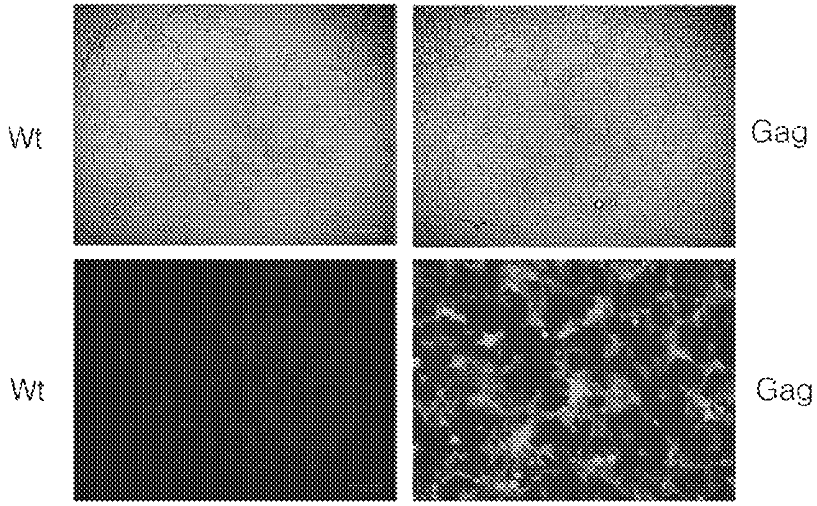
FIG. 32—Self-reporting cells display normal phenotypes and growth rates. 293T cells stably transduced with Gag have normal behavior, phenotypes and growth rates.
Figure 33:
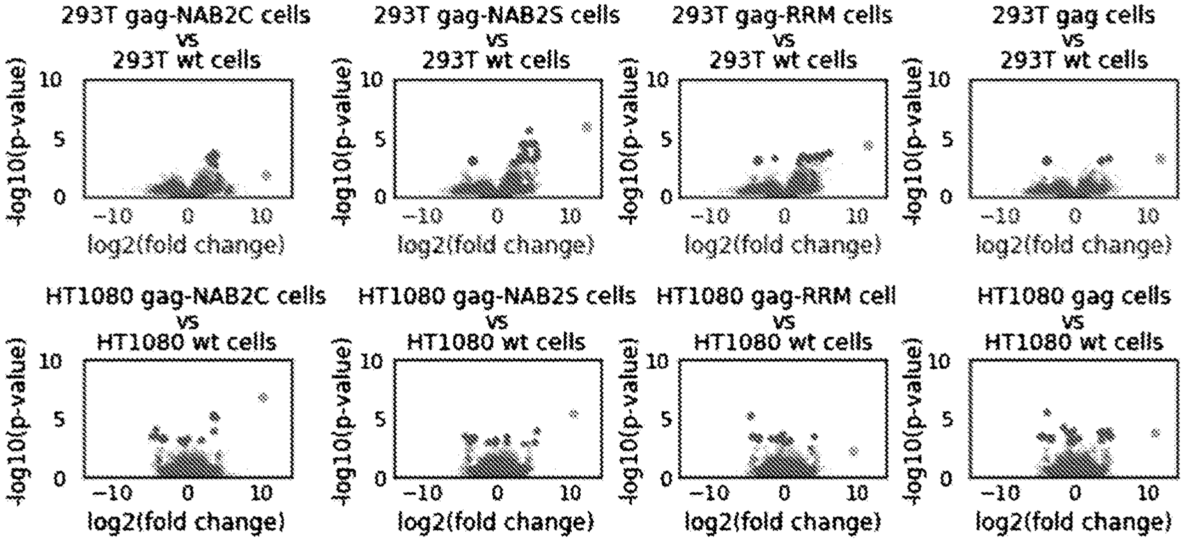
FIG. 33—Differential gene expression analysis for 293T and HT1080 cells. Self-reporting is minimally perturbative, with only a few significant differentially regulated genes. Gag (shown in orange) has the highest fold-change.
Figure 34:
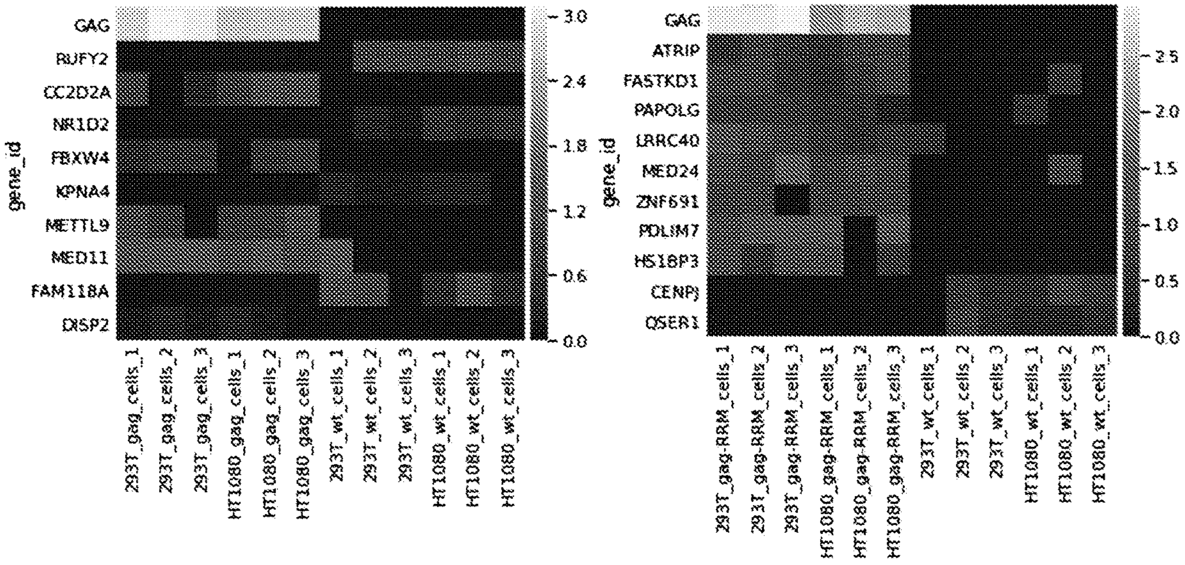
FIG. 34 Significant differentially regulated genes for Gag (left) and Gag-RRM (right).
Figure 35:
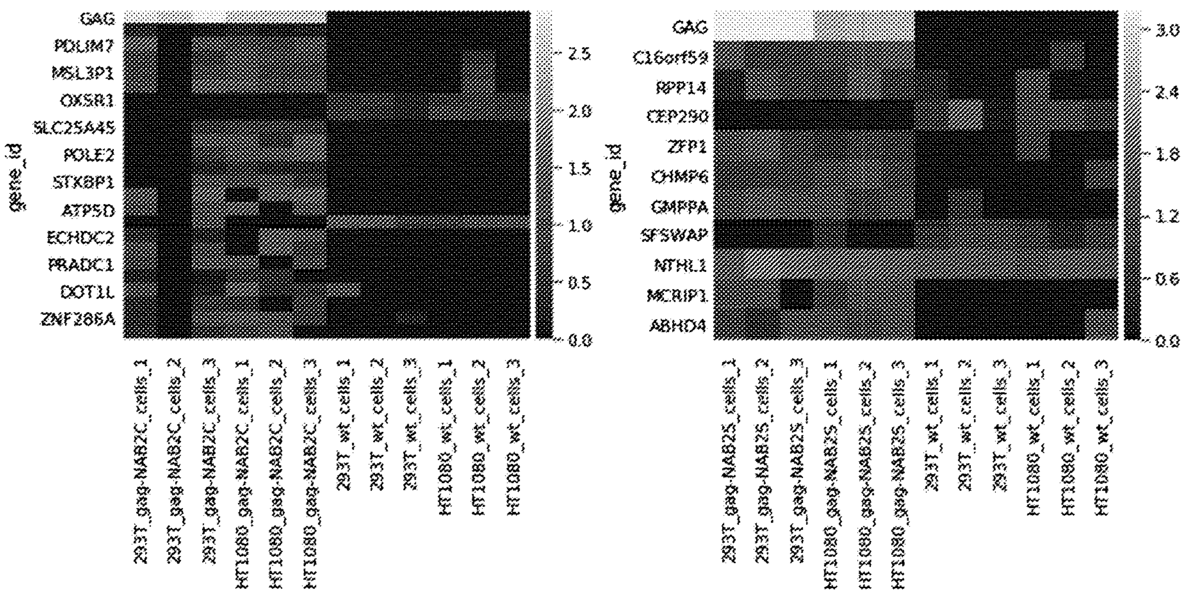
FIG. 35 Significant differentially regulated genes for Gag-NAB2C (left) and Gag-NAB2S (right).

To better characterize the RNA contents of VLPs, VLPs were enveloped with the affinity tagged envelope glycoprotein flag-VSVg and then performed a flag immunoprecipitation on supernatants. The immunoprecipitation was validated through western blots, and detecting Gag only when co-expressed with flag-VSVg demonstrated that the VLPs were properly enveloped with flag-VSVg, and that the VLPs remained intact throughout the purification (FIG. 26G). After performing RNA-seq on the supernatants, Applicants were able to detect-2000 genes on average from cells expressing Gag (FIG. 26G). When performing RNA-seq on supernatants after flag immunoprecipitation, high quality RNA-seq libraries were only able to be generated on supernatants from Gag+flag-VSVg+ cells (FIG. 26H), resulting in the detection of −1700 genes, thus confirming the specificity of the immunoprecipitation. These results, in conjunction with cells possessing normal morphology and growth rates (FIG. 32), gave confidence that measured RNA was indeed exported within VLPs induced by Gag expression.

Figure 26K:
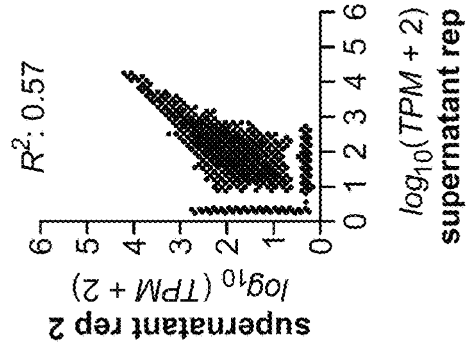
(FIG. 26K) RNA-seq replicate concordance of pGag+, pFlag-VSVg+293T supernatants.
Figure 26L:
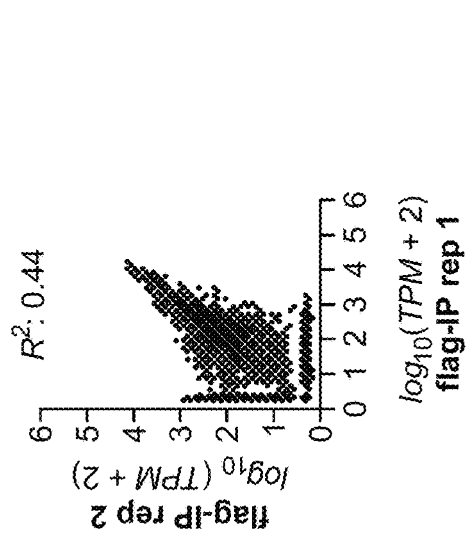
(FIG. 26L) RNA-seq replicate concordance of pGag+, pFlag-VSVg+293T supernatants that have undergone flag immunoprecipitation.
Figure 26M:
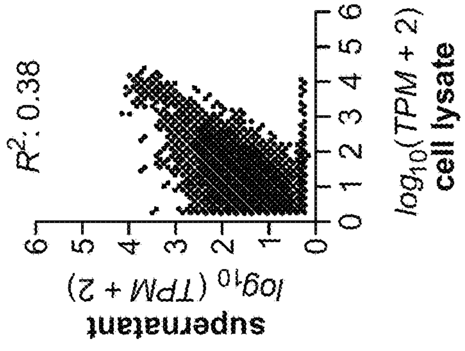
Figure 26N:
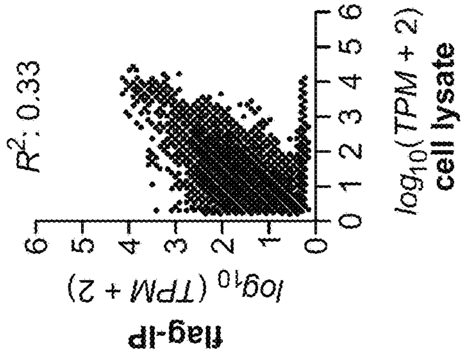
Figure 26O:
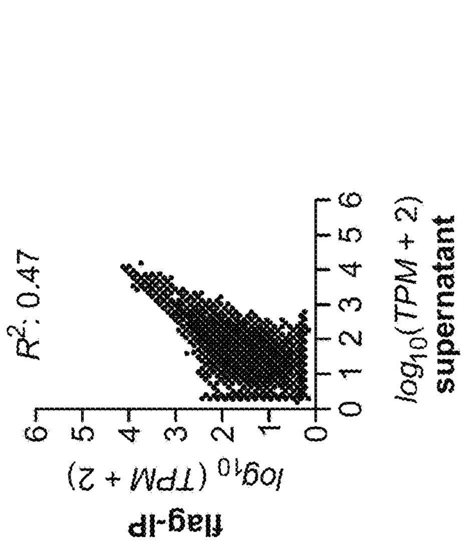
Figure 27A:
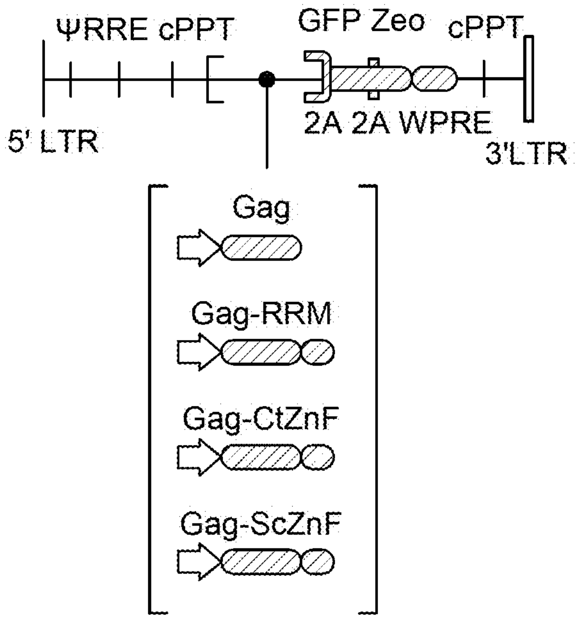
FIG. 27A-27K—(FIG. 27A) Schematic of lentivirus constructs.
Figure 27B:
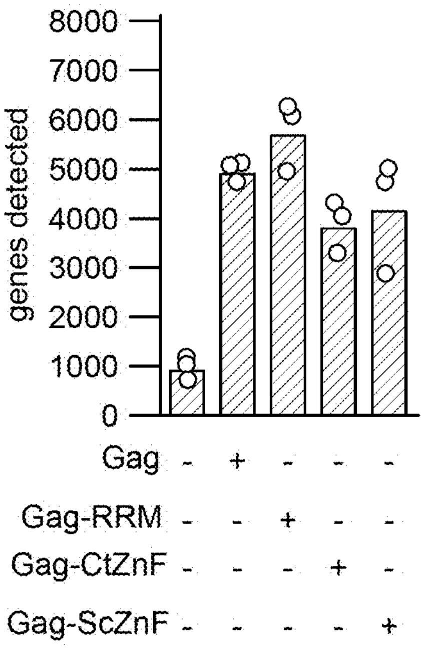
Figure 27C:
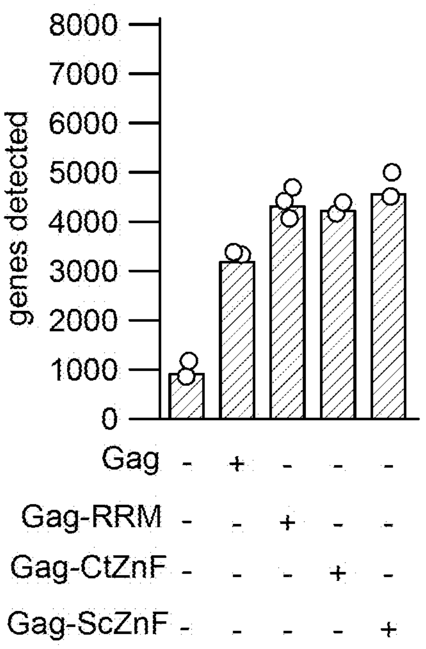

This RNA-seq data showed that VLPs could be used for quantitative RNA measurement (FIGS. 26K and 26L), and it was observed that exported RNA was representative of cellular lysate (FIGS. 26M and 26N) and that RNA measured in purified VLPs correlated with supernatant RNA (FIG. 26O). However, of interest was rationally engineering Gag to further increase the export repertoire. Gag has been reported to package viral genomic RNA through its basic nucleocapsid (NC) domain, which electrostatically interacts with negatively charged RNA and also recognizes cis-acting packaging signals. It was envisioned that poly(A)—binding domains would be attractive candidates for engineering Gag fusions for cellular self-reporting, in order to interact with polyadenylated tails of mammalian mRNA with high affinity. Tandem RNA recognition motifs RRM1-2 from human PABPC4 were selected as a candidate to engineer poly(A) interaction, as the tandem domains have been shown to interact with polyadenylated tails. In addition, zinc-finger domains from Nab2 orthologs in *Chaetomium thermophilum* (ZnF3-5) and *Saccharomyces cerevisiae* (ZnF5-7) were selected, which are also known to interact with polyadenylated tails. Lentivirus were generated packaging the designed fusion constructs (FIG. 27A) to produce single-copy integrated HEK293T and HT1080 cell lines with constitutive expression. After purifying VLPs from supernatant and preparing RNA-seq libraries, a X+Y fold increase (mean±SD, n=3, p=Z) was measured in detected genes from Gag+ cells relative to the wild type controls in 293T (FIG. 27B). Fusing poly(A)—binding domains to Gag resulted in higher genes detected in HT1080 cells (FIG. 27C), demonstrating that the exported RNA repertoire can indeed be enhanced by engineering the poly(A)—binding of Gag.

Figure 27D:
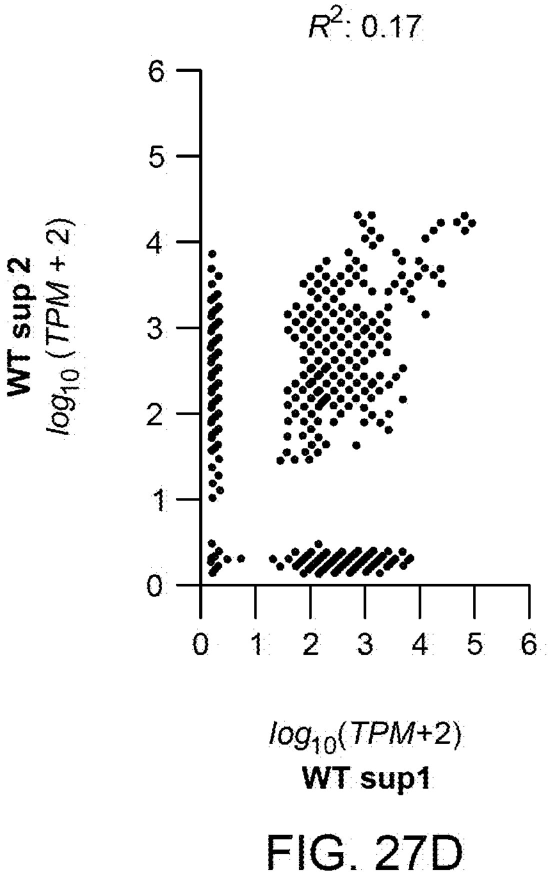
Figure 27E:
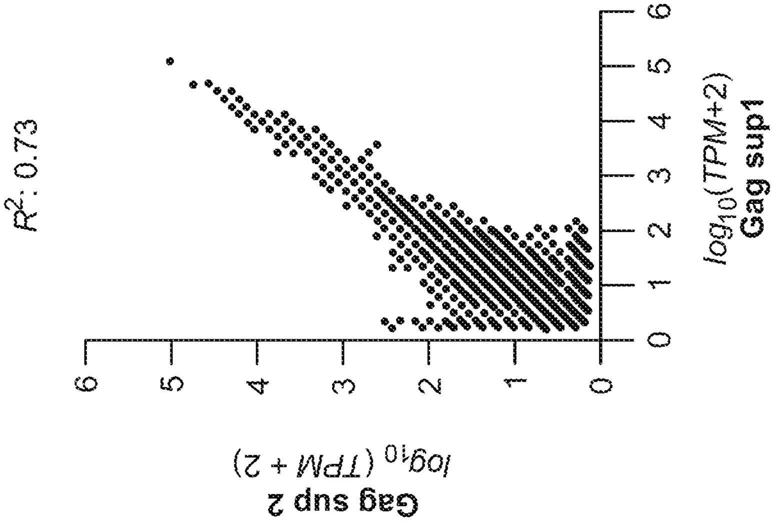
Figure 27F:
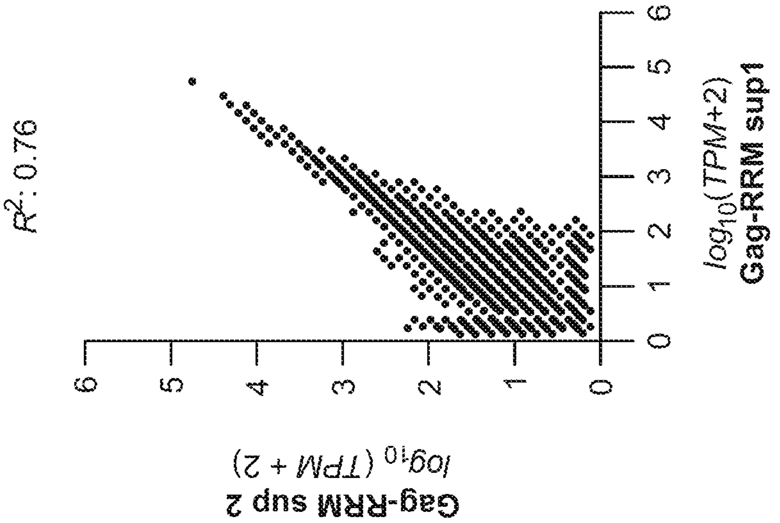
Figure 27G:
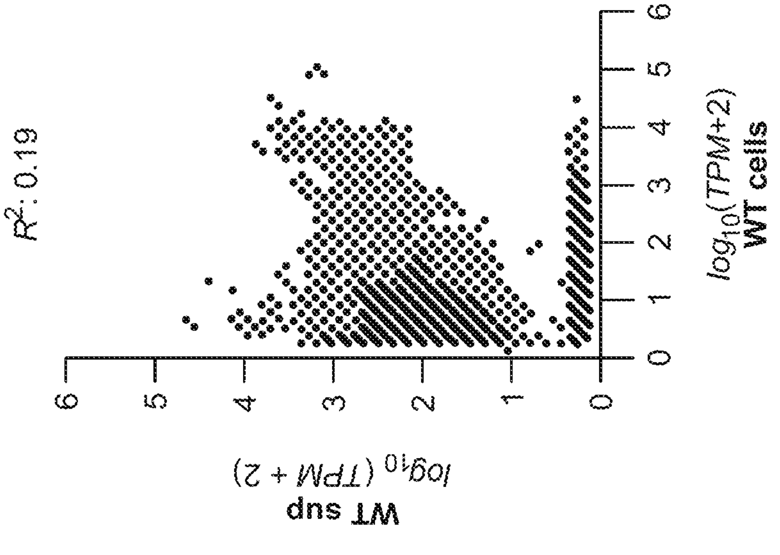
Figure 27H:
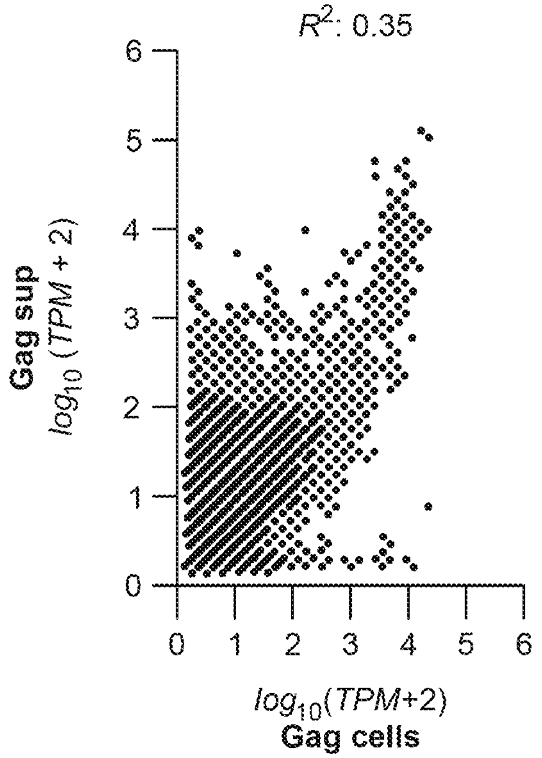
Figure 27I:
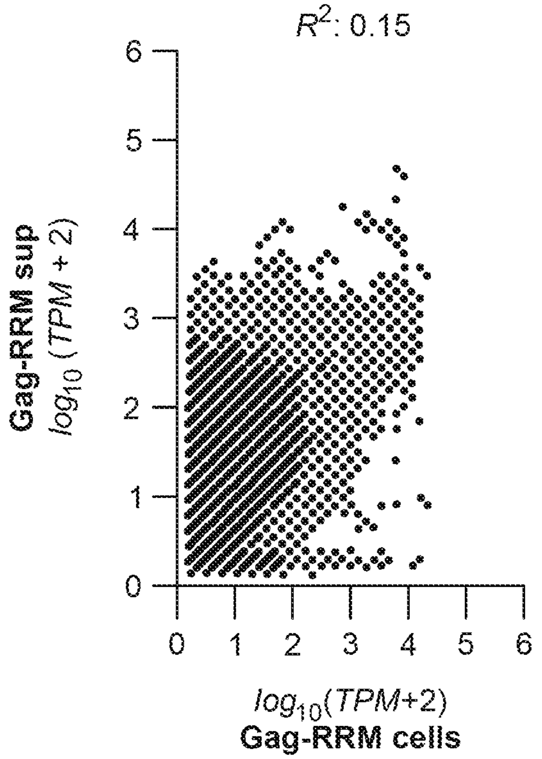
Figure 27J:
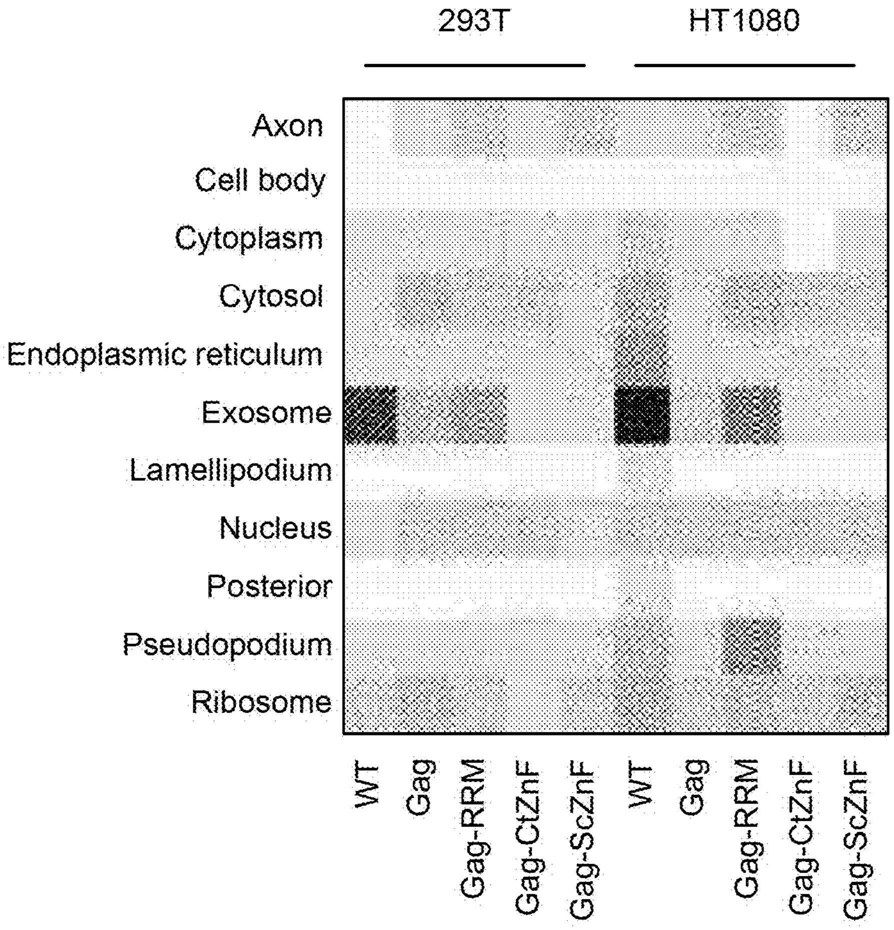
Figure 27K:
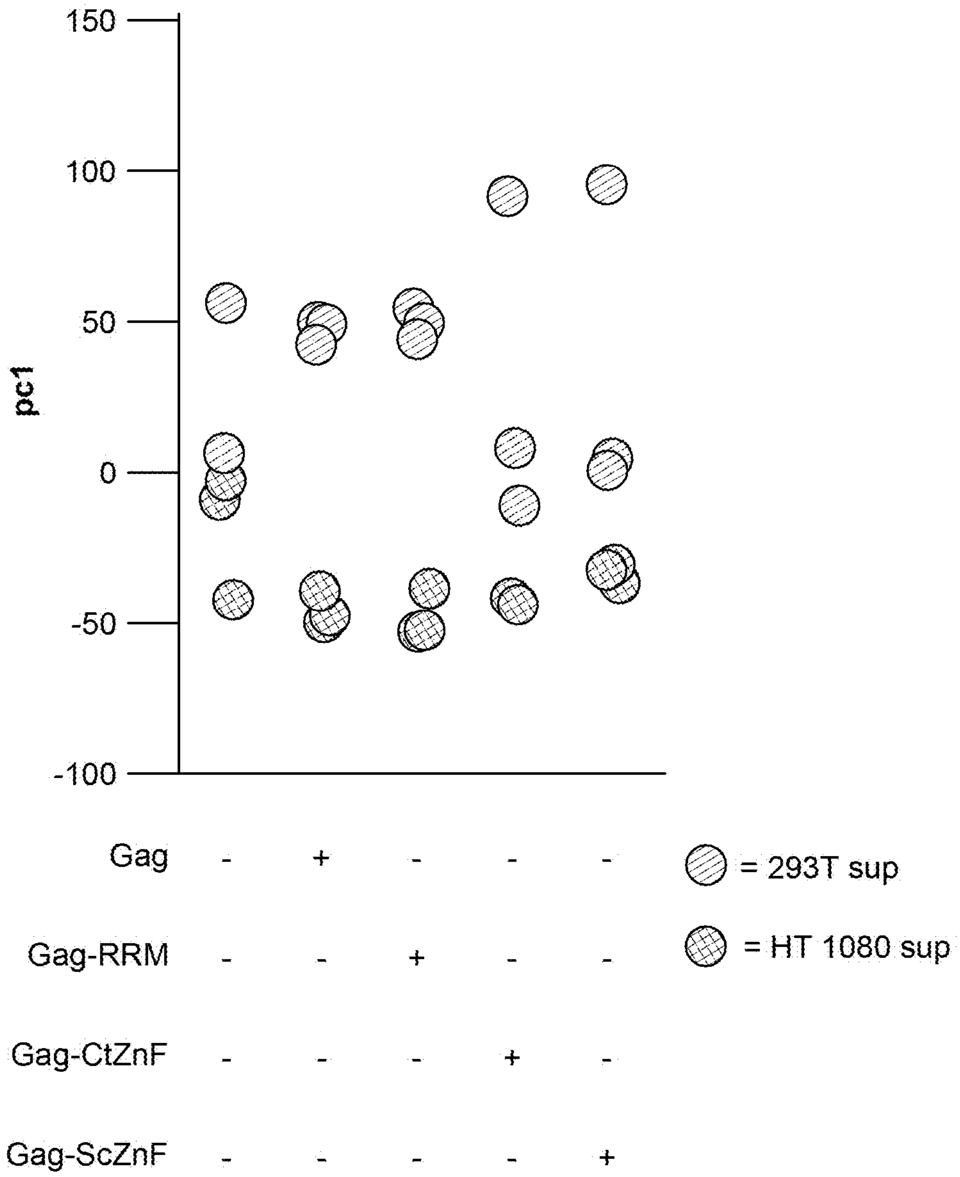
Figure 28:
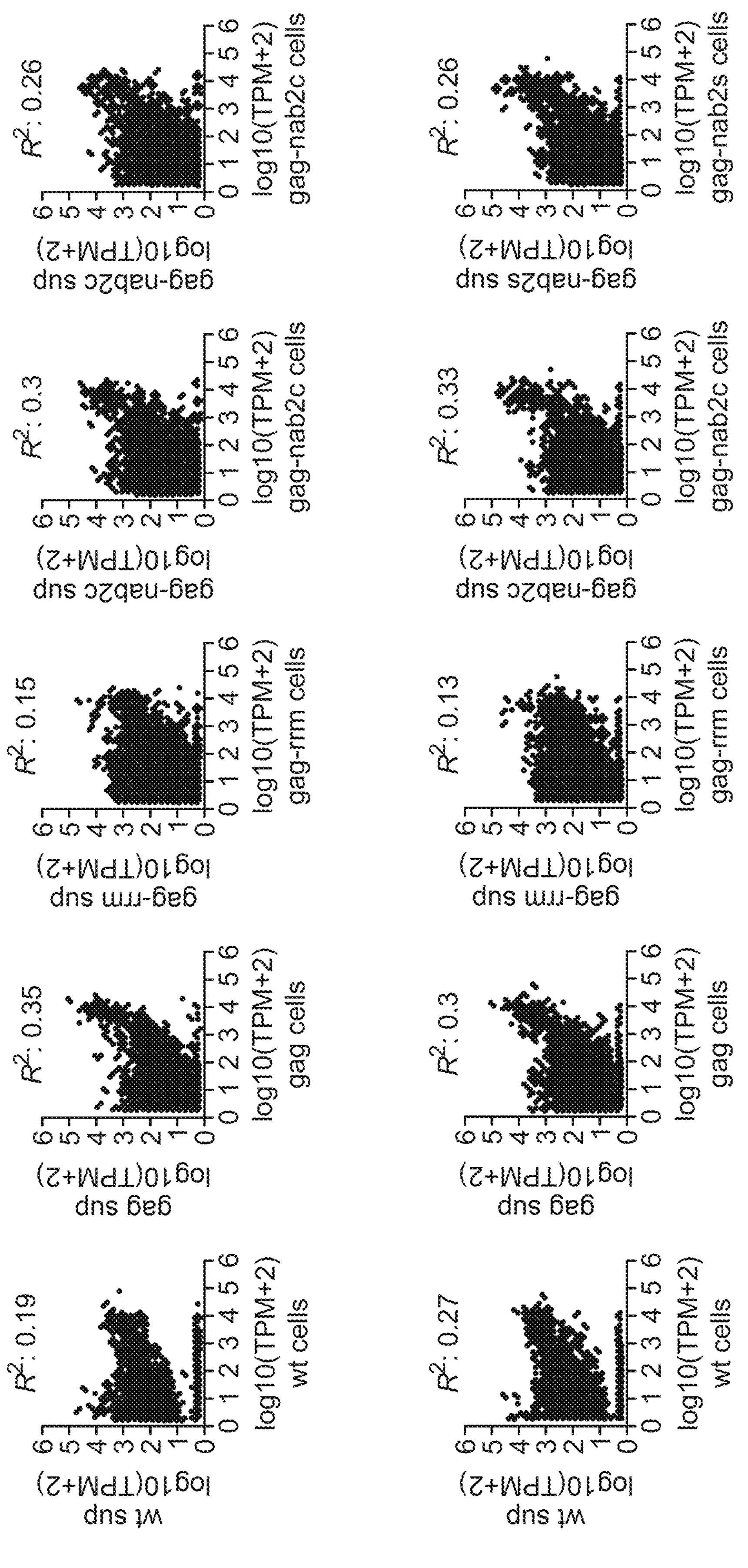
FIG. 28—RNA-seq representation plots between purified supernatants and corresponding lysates. 293T cells (top row) and HT1080 cells (bottom row).
Figure 29:
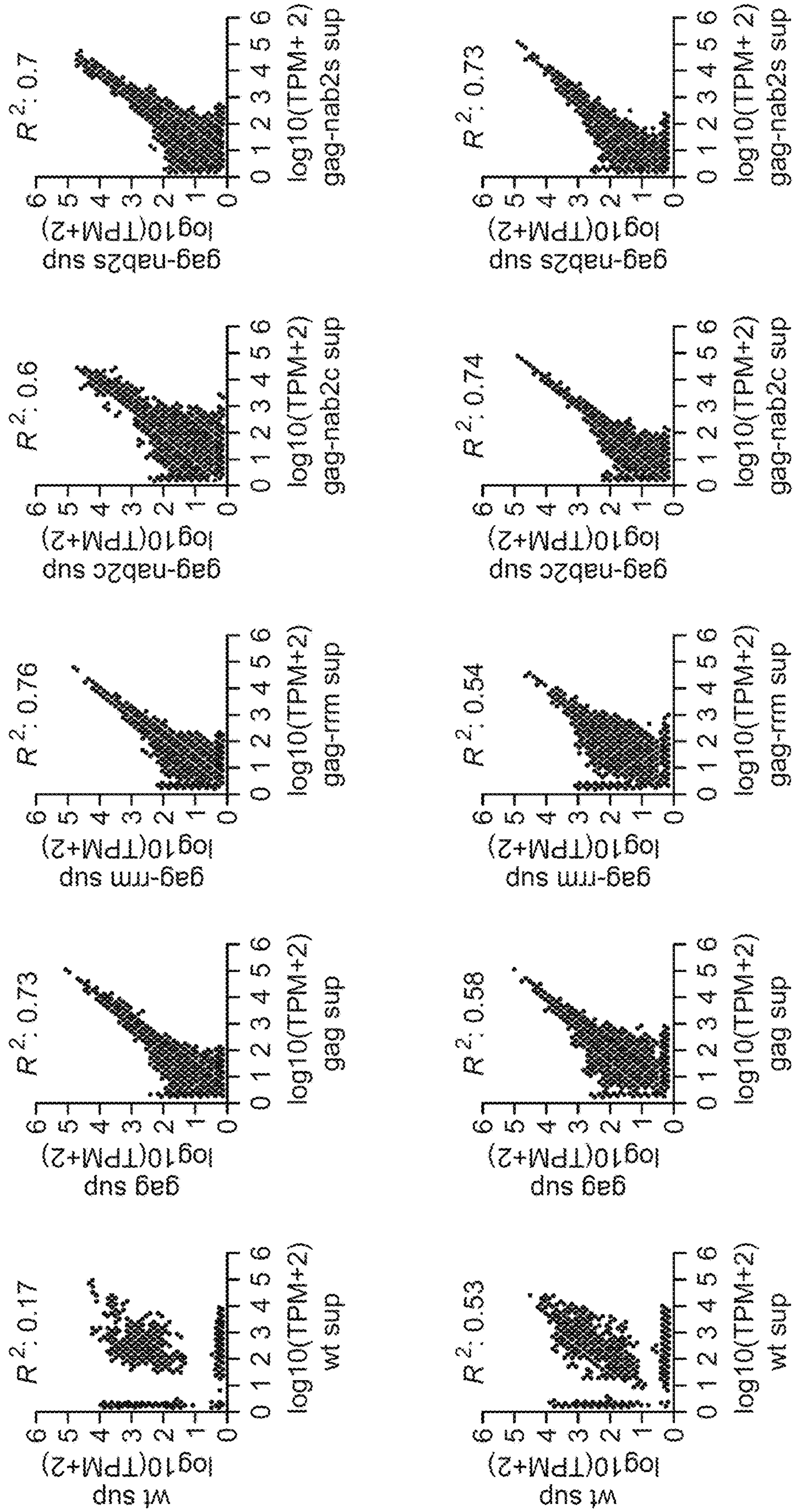
FIG. 29—RNA-seq data shows quantitative RNA export. Comparing biological replicates of 293T (top row) and HT1080 (bottom row), export constructs show quantitative RNA export for both cell lines.

All Gag constructs showed quantitative nature in 293T (FIG. 27D to 27F, FIG. 29), as well as in HT1080 (FIG. 29) when comparing biological replicates. Representation of exported RNA varied when comparing across constructs in 293T (FIG. 27G to 271) and HT1080 (FIG. 27D). This is likely due to packaging bias differences (FIG. 27J) as well as potential differences in VLP assembly properties that are currently unknown. Through unsupervised PCA, the exported RNA was analyzed to determine if supernatants carry sufficient RNA information to correctly classify into corresponding cell lines of origin. Indeed, when conducting PCA on each Gag construct subset, distinct cell line separation was seen with Gag and Gag-RRM constructs and minimal cell line separation with wild type cells (FIG. 27K).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method for continuous monitoring of live cells comprising:

(a) delivering into one or more cells a nucleic acid construct encoding a fusion protein and a construct RNA sequence, the fusion protein comprising a secretion-inducing domain and a construct RNA sequence capture domain, and the construct RNA sequence comprising a retrieval element, a barcode, and a cellular RNA capture element;

(b) expressing the nucleic acid construct in the one or more cells;

(c) capturing cellular RNA expressed in the one or more cells by binding the cellular RNA via the cellular RNA capture element of the construct RNA sequence;

(d) exporting the cellular RNA from the cell by binding the fusion protein construct RNA sequence capture domain to the retrieval element of the construct RNA such that the cellular RNA is exported from the cell in association with the secretion-inducing domain while maintaining cell viability, wherein the secretion-inducing domain self-assembles to form an export vesicle; and (e) isolating the exported vesicle containing captured cellular RNA transcripts at one or more time points.

2. The method of claim 1, further comprising:

generating an RNA-DNA duplex by reverse transcribing the captured cellular RNA using the construct RNA sequence as a primer for reverse transcription;

generating a DNA-DNA duplex by converting the construct RNA sequence to a corresponding DNA sequence with a second strand synthesis using a DNA primer such that the barcode is included in the DNA-DNA duplex;

generating a sequencing library from the generated DNA-DNA duplexes;

sequencing the sequencing library to identify the captured cellular RNA wherein the one or more cells from which the cellular RNA was isolated are identified from the barcode.

3. The method of claim 1, wherein the construct RNA sequence capture domain comprises about 20 amino acids to about 400 amino acids.

4. The method of claim 1, wherein the method for continuous monitoring is performed in vitro or is performed in vivo.

5. The method of claim 1, wherein the cells are eukaryotic cells.

6. The method of claim 1, wherein the barcode can be amplified by a cell and used to mark cellular components of the cell according to cell of origin.

7. The method of claim 1, wherein the nucleic acid construct further comprises a searchable filter sequence, wherein the filter sequence is set a fixed distance from the barcode and can be used to identify the barcode in downstream sequencing reads.

8. The method of claim 1, wherein the nucleic acid construct further comprises an adapter sequence, wherein the adapter sequence provides a complementary binding site for a reverse transcription primer.

9. The method of claim 6, further comprising a sequencing primer binding site complementary to one or more sequencing primers.

10. The method of claim 6, wherein the barcode is unique to an individual cell origin or cell lineage, and further comprising incorporating the barcode of the expressed nucleic acid construct to the captured cellular RNA to generate barcoded cellular RNA, thereby labeling components of a cell according to cell of origin or cell lineage.

11. The method of claim 10, wherein the barcode is attached to the cellular RNA by: use of the nucleic acid construct to prime first strand synthesis of the captured cellular RNA, ligation of the nucleic acid construct to the cellular RNA by RNA-RNA ligation, or further priming second strand synthesis.

12. The method of claim 10, further comprising amplifying the barcoded cellular RNA.

13. The method of claim 12, wherein the barcoded cellular RNA is amplified by RNA-dependent RNA synthesis facilitated by T7 RNA polymerase (RNAP).

14. A method for continuous monitoring of live cells comprising:

(a) delivering into one or more cells a nucleic acid construct encoding a fusion protein and a construct RNA sequence, the fusion protein comprising a secretion-inducing domain and a construct RNA sequence capture domain comprising about 20 amino acids to about 400 amino acids, and the construct RNA sequence comprising a retrieval element, a barcode, and a cellular RNA capture element;

(b) expressing the nucleic acid construct in the one or more cells;

(c) capturing cellular RNA expressed in the one or more cells by binding the cellular RNA via the cellular RNA capture element;

(d) exporting the cellular RNA from the cell by binding of the fusion protein construct such that the cellular RNA is exported from the cell in association with the secretion-inducing domain while maintaining cell viability, wherein the secretion-inducing domain self-assembles to form an export vesicle; and (e) isolating the exported vesicle containing captured cellular RNA transcripts at one or more time points.

15. The method of claim 14, wherein the secretion-inducing domain is a lentiviral capsid protein.

16. The method of claim 14, wherein the construct RNA sequence capture domain encodes a Poly(A) Binding Protein (PABP), Nab2 protein, or a fragment or variant thereof.

17. The method of claim 14, wherein the construct RNA sequence capture domain encodes a Poly(A) Binding Protein cytoplasmic 4 (PABPC4), a PABPC4 fragment, or a PABPC4 variant.

18. The method of claim 14, wherein the construct RNA sequence capture domain encodes *S. cerevisiae* Nab2 ZnF 5-7 or *C. thermophilum* Nab2 ZnF 3-5.

19. A method for continuous monitoring of live cells comprising:

(a) delivering into one or more cells a nucleic acid construct encoding a fusion protein and a construct RNA sequence, the fusion protein comprising a secretion-inducing domain comprising a lentivirus Gag protein and a construct RNA sequence capture domain comprising Poly(A) Binding Protein cytoplasmic 4 (PABPC4), and the construct RNA sequence comprising a retrieval element, a barcode, and a cellular RNA capture element;

(b) expressing the nucleic acid construct in the one or more cells;

(c) capturing cellular RNA expressed in the one or more cells by binding the cellular RNA via the cellular RNA capture element;

(d) exporting the cellular RNA from the cell by binding of the fusion protein construct such that the cellular RNA is exported from the cell in association with the secretion-inducing domain while maintaining cell viability, wherein the secretion-inducing domain self-assembles to form an export vesicle; and (e) isolating the exported vesicle containing captured cellular RNA transcripts at one or more time points.

* * * * *